United States Patent [19]

Ueda et al.

[11] Patent Number: 4,745,179

[45] Date of Patent: May 17, 1988

[54] [59]VALINE INSULIN-LIKE GROWTH FACTOR I AND PROCESS FOR PRODUCTION THEREOF

[75] Inventors: Ikuo Ueda, Toyonaka; Mineo Niwa, Mukoo; Yoshimasa Saito, Osaka; Susumu Sato; Hiroki Ono, both of Osaka; Tadashi Kitaguchi, Amagasaki, all of Japan

[73] Assignee: Fujisawa Pharmaceutical Co., Ltd., Osaka, Japan

[21] Appl. No.: 713,828

[22] Filed: Mar. 20, 1985

[30] Foreign Application Priority Data

Apr. 2, 1984 [GB] United Kingdom ................. 8408473
Jun. 1, 1984 [GB] United Kingdom ................. 8413989
Sep. 25, 1984 [GB] United Kingdom ................. 8424157

[51] Int. Cl.$^4$ .......................... C07K 13/00; C07K 7/10
[52] U.S. Cl. .................................. 530/350; 530/324; 530/345; 530/399; 530/303
[58] Field of Search .............. 530/324, 303, 350, 399, 530/345; 935/47, 48

[56] References Cited

U.S. PATENT DOCUMENTS 4,356,270 10/1982 Itakura .................................. 935/60

FOREIGN PATENT DOCUMENTS

| 0001929 | 5/1979 | European Pat. Off. . |
| 0035384 | 9/1981 | European Pat. Off. . |
| 0095361 | 11/1983 | European Pat. Off. . |
| 8304030 | 11/1983 | European Pat. Off. . |
| 0117063 | 8/1984 | European Pat. Off. . |
| 0135094 | 3/1985 | European Pat. Off. . |
| 84/03103 | 8/1984 | PCT Int'l Appl. . |

OTHER PUBLICATIONS

Chemical Abstracts, vol. 105, No. 185208b, Abstract of Niwa et al., Ann. N.Y. Acad. Sci., 469 (Biochem. Eng. 4), 31–52 (1986).
Rinderknecht et al, The Journal of Biological Chemistry, vol. 253, No. 8, pp. 2769–2776 (1978).
European Search Report, to Corresponding Application No. EP 85103741, dated Jul. 20, 1987.
The Embo Journal, vol. 3, No. 2, pp. 361–364 (1984); "Isolation of the Human Insulin–Like Growth Factor I Gene Using a Single Synthetic DNA Probe", Ullrich et al.
Biological Abstracts, RRM No. 26023523; Bioscience Information Service, "The Chemical Synthesis Molecular Cloning and Expression in Yeast of Genes Coding for Human Insulin–Like Growth Factors I and II", G. T. Mullenbach et al. (1983).
Proc. Natl. Akad. Sci. U.S.A., vol. 78, No. 8 (1981), pp. 4936–4940, Gentz et al, "Cloning and Analysis of Strong Promoters is Made Possible by the Downstream Placement of an RNA Termination Signal".
Gene, vol. 35 (1985), pp. 83–89, ref. No. 1269, Peters et al, "Expression of a Biologically Active Analogue of Somatomedin–C/Insulin–Like Growth Factor I".
Eur. Congr. Biotechnology, vol. 3, (1984–3rd), pp. 287–292, Elmblad et al, "Cloning and Expression of a Synthetic Gene for the Human Insulin Like Growth Factor-1 (IGF-1)".
Nature, vol. 295, (1982), pp. 503–508, Gray et al, "Expression of Human Immune Interferon cDNA in Escherichia coli and Monkey Cells".
Nature, vol. 306, Dec. 8, 1983, pp. 609–611; M. Jansen et al.: "Sequence of cDNA Encoding Huma Insulin--Like Growth Factor I Precursor".
Nuclein Acids Research, vol. 10, No. 21, 1982, pp. 6639–6657; J. D. Windass et al.: "The Construction of a Synthetic Escherichia coli trp Promotor . . . ".
Biological Abstracts, RRM No. 27044601; M. Peters et al.: "Clongin and Expression in Escherichia coli of a Gene for Human Insulin–Like . . . ".
Chemical Abstracts, vol. 100, No. 23, Jun. 1984, p. 139, A. Ulrich et al.: "Isolation of the Human Insulin–Like Growth Factor I Gene Using . . . ".
Biological Abstracts, RRM No. 46023523; G. T. Mullenbach et al.: "The Chemical Synthesis Molecular Cloning and Expression in Yeast of Genes . . . ".
Biological Abstracts, RRM No. 28052534; D. Reismann et al.: "Comparison of the Immunochemical Receptor Binding and Biological Properties . . . ".
Chemical Abstracts, vol. 102, No. 3, Jan. 21, 1985, p. 82; D. Schalch et al; "Insulin–Like Growth Factor I/-Somatomedin C (IGE-I/Sm C): Comparison . . . ".
Angewandte Cheie Int. Ed. Engl., vol. 22, 1983, pp. 842–858; F. Wengenmayer; "Synthesis of Peptide Hormones Using Recombinant DNA Techniques".
Am. J. Hum. Genet., vol. 31, 1979, pp. 531–538; A. D. Riggs et al.: "Synthetic DNA and Medicine".
Li et al, Proc. Natl. Acad. Sci. U.S.A., vol. 80, pp. 2216–2220 (1983).

Primary Examiner—John Kight
Assistant Examiner—Christina Chan
Attorney, Agent, or Firm—Oblon, Fisher, Spivak, McClelland & Maier

[57] ABSTRACT

The present invention relates to a [59]Valine insulin-like growth factor I ([59]Val.IGF-I), to a [59]Val-IGF-I fused to a protective peptide, to a gene coding for [59]Val-IGF-I, to a gene coding for fused [59]Val-IGF-I, to a plasmid containing the [59]Val-IGF-I gene, to a host organism containing a plasmid containing the [59]Val-IGF-I gene, to a host organism containing a plasmid containing the fused [59]Val-IGF-I gene, and to processes for the production of these.

3 Claims, No Drawings

$^{59}$VALINE INSULIN-LIKE GROWTH FACTOR I AND PROCESS FOR PRODUCTION THEREOF

BACKGROUND OF THE INVENTION

1. Field of the Invention

This invention relates to $^{59}$valine insulin-like growth factor I (hereinafter referred to as $^{59}$Val-IGF-I, to $^{59}$Val-IGF-I fused with a protective peptide (hereinafter referred to as fused $^{59}$Val-IGF-I), to a gene coding for $^{59}$Val-IGF-I, to a gene coding for fused $^{59}$Val-IGF-I, to a plasmid containing $^{59}$Val-IGF-I gene, to a plasmid containing fused $^{59}$Val-IGF-I gene, to a host organism containing plasmid containing $^{59}$Val-IGF-I gene, to a host organism containing plasmid containing fused $^{59}$Val-IGF-I gene, and to processes for the production thereof.

$^{59}$Val-IGF-I may have insulin-like potency and stimulation potency of sulfate-uptake by cartilage and may enhance protein and DNA synthesis in a cell.

Therefore, it may be useful in promoter of growth.

In addition, it may be useful in clinical treatment of diabetes.

SUMMARY OF THE INVENTION

It was perceived that the application of recombinant DNA and associated technologies would be the most effective way of producing large quantities of $^{59}$Val-IGF-I.

$^{59}$Val-IGF-I is new, and the amino acid sequence thereof can be presented as follows:

$$\underset{1}{Gly}-Pro-Glu-Thr-Leu-Cys-Gly-Ala-Glu-\underset{10}{Leu}-$$

$$-Val-Asp-Ala-Leu-Gln-Phe-Val-Cys-Gly-\underset{20}{Asp}-$$

$$-Arg-Gly-Phe-Tyr-Phe-Asn-Lys-Pro-Thr-\underset{30}{Gly}-$$

$$-Tyr-Gly-Ser-Ser-Ser-Arg-Arg-Ala-Pro-\underset{40}{Gln}-$$

$$-Thr-Gly-Ile-Val-Asp-Glu-Cys-Cys-Phe-\underset{50}{Arg}-$$

$$-Ser-Cys-Asp-Leu-Arg-Arg-Leu-Glu-Val-\underset{60}{Tyr}-$$

$$-Cys-Ala-Pro-Leu-Lys-Pro-Ala-Lys-Ser-\underset{70}{Ala}$$

DETAILED DESCRIPTION OF THE PREFERRED EMBODIMENTS

The inventors of this invention succeeded in producing a large amount of $^{59}$Val-IGF-I by using the following essential steps.

STEP 1

A process for the production of a gene coding for $^{59}$Val-IGF-I. This process is optionally followed by a process for the production of fuses $^{59}$Val-IGF-I gene, i.e. a gene coding for $^{59}$Val-IGF-I fused with a protective peptide which comprises linking a gene coding for a protective peptide with $^{59}$Val-IGF-I gene with or without a linker upstream of said $^{59}$Val-IGF-I gene.

A suitable "linker" may include a gene coding for several amino acids and having a suitable restriction enzyme recognition sites to link a protective peptide upstream of $^{59}$Val-IGF-I gene, and the "linker" per se constructs said protective peptide.

Most suitable "linkers" are exemplified hereinafter.

In addition, a terminator may be inserted downstream of and adjacent to said $^{59}$IGF-I gene.

A suitable "terminator" may include a gene coding for suitable restriction enzyme recognition sites.

Most suitable "terminations" are exemplified hereinafter.

Suitable "fused $^{59}$Val-IGF-I, i.e. $^{59}$Val-IGF-I fused with a protective peptide" are illustrated and exemplified hereinafter in the Examples.

STEP 2

A process for the production of an expression vector which comprises inserting a promoter gene and a gene coding for $^{59}$Val-IGF-I or a gene coding for fused $^{59}$Val-IGF-I into a plasmid.

A suitable "expression vector" may include one of the following plasmids: pSdV2trp, pSdV2-322trp, pLHSdVtrp, pSdV2-lac, pSdV2-NT49 and the like.

A most suitable "plasmid" may include pBR322 and the like.

STEP 3

A process for the production of a transformant which comprises transforming a host organism with said expression vector.

A suitable "host organism" may include Escherichia (hereinafter referred to as *E.*) *coli* (e.g. *E. coli* HB101, *E. coli* HI2019, *E. coli* MM294, etc.) and the like.

STEP 4

A process for the production of $^{59}$Val-IGF-I or fused $^{59}$Val-IGF-I which comprises culturing said transformant in a suitable medium.

STEP 5

A process for isolation of $^{59}$Val-IGF-I or fused Val-IGF-I from host organism cells.

STEP 6 (OPTIONAL)

A process for the production of $^{59}$Val-IGF-I which comprises subjecting said fused $^{59}$Val-IGF-I to a reaction removing the protective peptide.

The "protecive peptide" in the term "fused $^{59}$Val-IGF-I, i.e. $^{59}$Val-IGF-I fused with a protective peptide" is used for protecting $^{59}$Val-IGF-I from degradation by protease in the cells of a host organism, and is removed by elimination reaction of said fused $^{59}$Val-IGF-I.

Namely, said fused $^{59}$Val-IGF-I is an intermediate for preparing $^{59}$Val-IGF-I by elimination reaction. The protective peptide can be any eliminable protective peptide derived from natural or synthetic protein, natural or synthetic peptide, or a fragment thereof.

Suitable "fused $^{59}$Val-IGF-I" may include $^{59}$-Val-IGF-I fused with a protein peptide through methionine of the protein peptide.

Suitable agent used in this elimination reaction may include cyanogen bromide and the like.

In this step, when the protein peptide is fused with $^{59}$Val-IGF-I through methionine of the protein peptide, fused with $^{59}$Val-IGF-I can be converted to $^{59}$Val-IGF-I by elimination reaction with cyanogen bromide, in high yield.

The present elimination reaction can be conducted under mild conditions in a conventional solvent which does not adversely affect the reaction.

From the above amino acid sequence of [59]Val-IGF-I, a corresponding nucleotide sequence has been invented, subject to a number of specific non-obvious criteria. The [59]Val-IGF-I gene has been cloned by inserting it into a known plasmid, as a cloning vector. The [59]Val-IGF-I gene has been excised from the recombinant plasmid, and then inserted into a plasmid specifically designed to maximize expression of the [59]Val-IGF-I gene under the control of a promoter. A structural gene coding for a protective peptide is optionally inserted into the recombinant plasmid upstream of and adjacent to said [59]Val-IGF-I gene.

Although the present invention is illustrated in detail hereinafter, the present invention is not limited thereto.

[1]

PREPARATION AND CLONING OF A [59]Val-IGF-I GENE (1) Preparation of a [59]Val-IGF-I gene:

From the above amino acid sequence, because of the diversity of the genetic code, it is possible to predict numerous nucleotide sequences which would code for the [59]Val-IGF-I.

In the inventive determination of an optimum sequence from the large number of possibilities, several non-obvious criteria have been observed. Firstly, trinucleotide codons should be used which are acceptable in a host organism to be used. Secondly, it should be desirable to have different restriction enzyme recognition sites at the terminal of the molecule so as to allow insertion into a plasmid in a desired orientation. Moreover, it should be decided to select sites which will be allowed to use well known cloning vectors. Thirdly, the synthesis should not be unnecessarily complicated, and illegitimate cross-hybridization should be minimized in order to facilitate gene assembly, so that stable off-diagonal interactions might be avoided as far as possible.

The one of the preferred sequence selected for the coding for portion of the [59]Val-IGF-I gene can be shown as follows:

In the sequence in this specification A, G, C and T mean the formula:

respectively, and

5'-terminal A, G, C and T mean the formula:

```
                 1
           Gly   Pro   Glu   Thr   Leu   Cys   Gly   Ala
Coding:    5'-GGT—CCT— GAA—ACT—CTG—TGC—GGC—GCT—
Noncoding: 3'-CCA—GGA—CTT— TGA—GAC—ACG—CCG—CGA—

10                                                        20
Glu   Leu  Val   Asp   Ala   Leu   Gln   Phe   Val   Cys   Gly   Asp   Arg
GAA—CTG—GTT—GAC—GCT—CTG—CAA—TTT— GTA—TGT—GGT—GAT—CGT—
CTT— GAC—CAA—CTG—CGA—GAC—GTT—AAA—CAT—ACA—CCA—CTA—GCA—

30
Gly   Phe   Tyr   Phe   Asn   Lys   Pro   Thr   Gly   Tyr   Gly   Ser   Ser
GGT—TTC— TAC—TTC— AAC—AAA—CCG—ACC—GGC—TAT—GGC—TCC— AGC—
CCA—AAG—ATG—AAG—TTG—TTT— GGC—TGG—CCG—ATA—CCG—AGG—TCG—

40
Ser   Arg   Arg   Ala   Pro   Gln   Thr   Gly   Ile   Val   Asp   Glu   Cys
TCT— CGT—CGC—GCA—CCG—CAG—ACT—GGT—ATC—GTA—GAC—GAA—TGC—
AGA—GCA—GCG—CGT—GGC—GTC—TGA—CCA—TAG—CAT—CTG—CTT— ACG—

50                                                        60
Cys   Phe   Arg   Ser   Cys   Asp   Leu   Arg   Arg   Leu   Glu   Val   Tyr
TGT—TTT— CGT—TCT— TGC—GAT—CTC— CGC—CGT—CTG—GAA—GTT—TAC—
ACA—AAA—GCA—AGA—ACG—CTA—GAG—GCG—GCA—GAC—CTT— CAA—ATG—

70
Cys   Ala   Pro   Leu   Lys   Pro   Ala   Lys   Ser   Ala
TGT—GCT—CCA— CTG—AAG—CCA—GCA—AAA—TCC— GCG—3'
ACA—CGA—GGT—GAC—TTC— GGT—CGT—TTT— AGG—CGC—5'
```

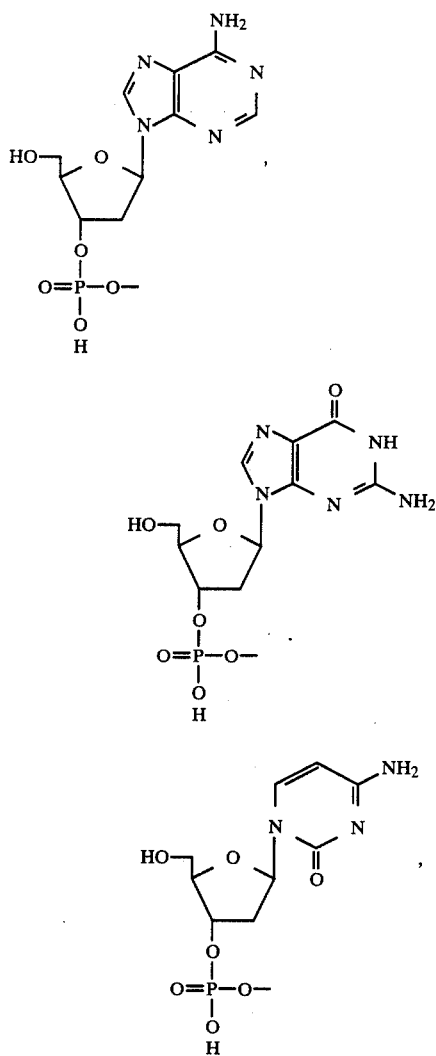

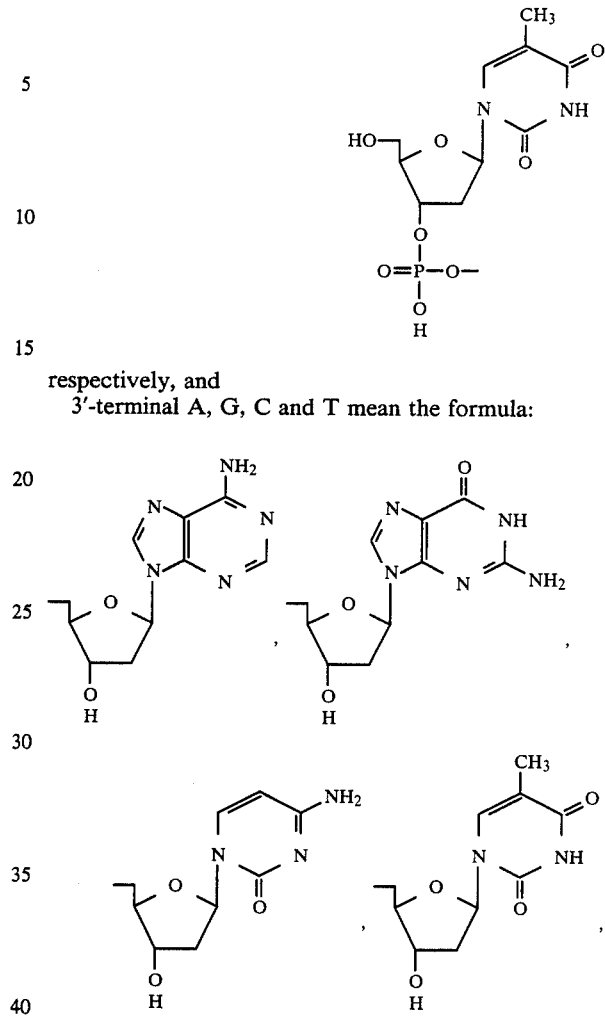

respectively, and

3'-terminal A, G, C and T mean the formula:

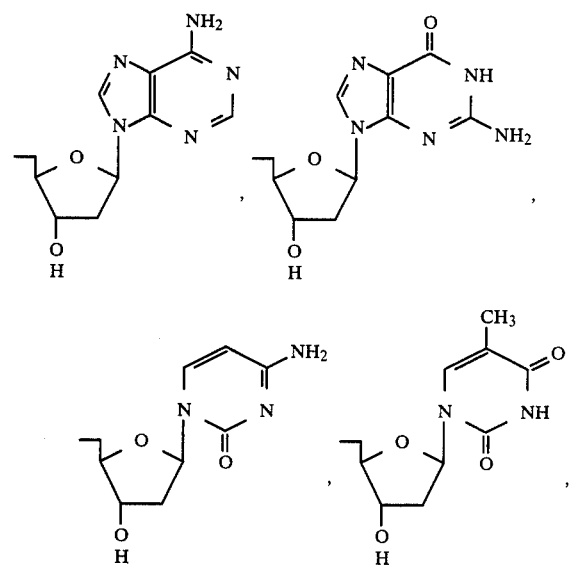

respectively.

Considering the above-mentioned criteria, particularly in consideration of the second criteria mentioned above, the following slightly longer sequence can be selected.

In fact, as a suitable embodiment of this invention, EcoRI and BamHI sites can be selected and introduced at the 5' and 3' ends, respectively.

Further, a methionine codon (ATG) was inserted upstream of and adjacent to the N-terminal amino acid codon of $^{59}$Val-IGF-I, and two stop codons (TGA and TAG) were inserted downstream of and adjacent to the C-terminal codon.

```
                        (AvaII)
         EcoRI    Met   Gly   Pro   Glu   Thr   Leu   Cys   Gly
Coding:     5'-AATTC— ATG—GGT—CCT— GAA—ACT—CTG— TGC— GGC—
Noncoding:     3'—G—TAC—CCA— GGA—CTT— TGA—GAC—ACG—CCG—

10
Ala   Glu   Leu   Val   Asp   Ala   Leu   Gln   Phe   Val   Cys   Gly   Asp   Arg         20
GCT—GAA—CTG—GTT—GAC—GCT—CTG—CAA—TTT— GTA—TGT—GGT—GAT—CGT—
CGA—CTT— GAC—CAA—CTG—CGA—GAC—GTT— AAA—CAT— ACA—CCA— CTA—GCA—

30
Gly   Phe   Tyr   Phe   Asn   Lys   Pro   Thr   Gly   Tyr   Gly   Ser   Ser   Ser
GGT—TTC— TAC— TTC— AAC—AAA—CCG— ACC—GGC—TAT— GGC—TCC— AGC—TCT—
CCA— AAG—ATG—AAG—TTG—TTT— GGC—TGG—CCG— ATA—CCG— AGG—TCG— AGA—
```

-continued

```
                         40
Arg  Arg  Ala  Pro  Gln  Thr  Gly  Ile  Val  Asp  Glu  Cys  Cys  Phe
CGT—CGC—GCA—CCG—CAG—ACT—GGT—ATC—GTA—GAC—GAA—TGC—TGT—TTT—
GCA—GCG—CGT—GGC—GTC—TGA—CCA—TAG—CAT—CTG—CTT—ACG—ACA—AAA—

50                                                60
Arg  Ser  Cys  Asp  Leu  Arg  Arg  Leu  Glu  Val  Tyr  Cys  Ala  Pro
CGT—TCT—TGC—GAT—CTC—CGC—CGT—CTG—GAA—GTT—TAC—TGT—GCT—CCA—
GCA—AGA—ACG—CTA—GAG—GCG—GCA—GAC—CTT—CAA—ATG—ACA—CGA—GGT—

70
Leu  Lys  Pro  Ala  Lys  Ser  Ala  stop  stop  BamHI
CTG—AAG—CCA—GCA—AAA—TCC—GCG—TGA—TAG—3'
GAC—TTC—GGT—CGT—TTT—AGG—CGC—ACT—ATC—CTAG—5'
```

The present invention also relates to a process for the production of such a gene characterized in that it comprises hybridization and ligation of a number of the corresponding oligonucleotide blocks.

(i) Synthesis of oligonucleotides:

It was in fact decided to synthesize a molecule having the above expanded sequence by making 30 synthetic oligonucleotides, which will be hybridized and ligated in pre-determined stage to give the double-stranded nucleotide sequence, mentioned above.

In the description of the synthesis of oligonucleotides in this specification, the following abbreviations are used.

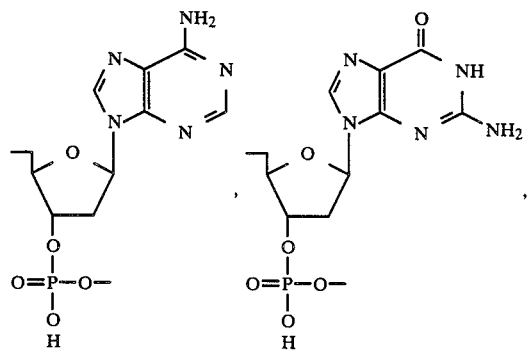

respectively, and
3'-terminal A, G, C and T mean the formula:

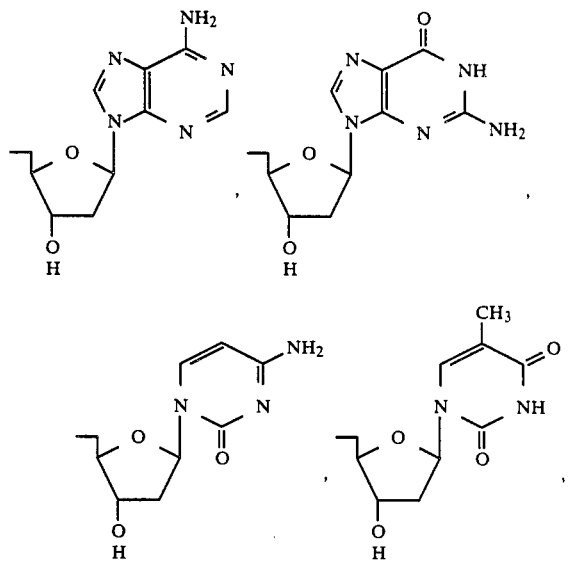

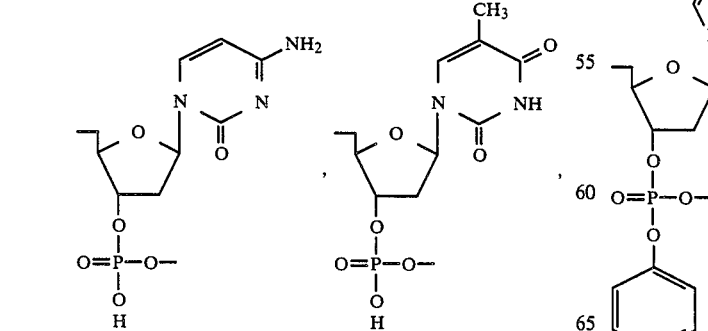

respectively, and $A^{Bz}$po, $G^{iB}$po, $C^{Bz}$po, Tpo and $^{Ac}$Upo mean the formula:

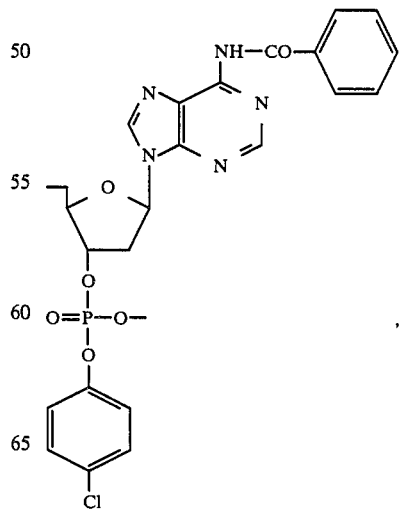

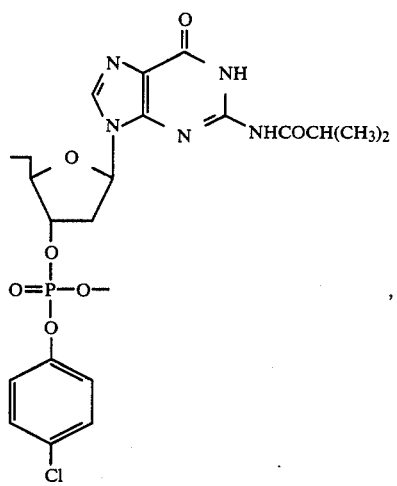

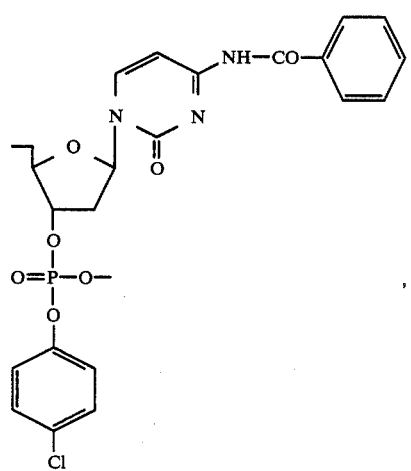

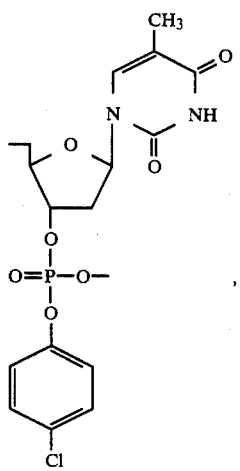

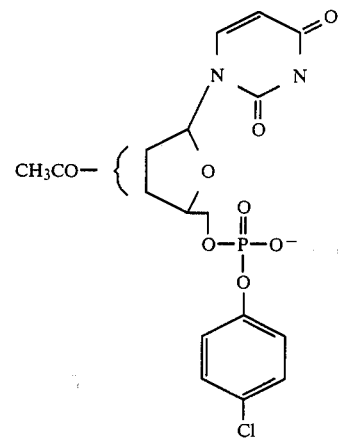

respectively, and

DMTr is dimethoxytrityl,

B is a base selected from adeninyl, guaninyl, cytosinyl and thyminyl (for convenience, protecting group are not shown), U is uracyl, Ac is acetyl, m is an integer of 1 or 2, and n is an integer of 1 to 12.

The oligonucleotides are as follows:

| | |
|---|---|
| (1) | HOApApTpTpCpApTpGpGpGpTOH (A1) |
| (2) | HOTpTpTpCpApGpGpApCpCpCpApTpGOH (A2) |
| (3) | HOCpCpTpGpApApApCpTpCpTpGpTpGOH (B1) |
| (4) | HOCpApGpCpGpCpCpGpCpApCpApGpApGOH (B2) |
| (5) | HOCpGpGpCpGpCpTpGpApApCpTpGpGpTOH (C1) |
| (6) | HOApGpApGpCpGpTpCpApApCpCpApGpTpTOH (C2) |
| (7) | HOTpGpApCpGpCpTpCpTpGpCpApApTpTpTOH (D1) |
| (8) | HOCpCpApCpApTpApCpApApApTpTpGpCOH (D2) |
| (9) | HOGpTpApTpGpTpGpGpTpGpApTpCpGpTOH (E1) |
| (10) | HOTpApGpApApApCpCpCpApCpGpApTpCpAOH (E2) |
| (11) | HOGpGpTpTpTpCpTpApCpTpTpCpApApCOH (F1) |
| (12) | HOGpGpTpCpGpGpTpTpTpGpTpTpGpApApGOH (F2) |
| (13) | HOApApApCpCpGpApCpCpGpGpCpTpApTpGOH (G1) |
| (14) | HOGpCpTpGpGpApGpCpCpApTpApGpCpCOH (G2) |
| (15) | HOGpCpTpCpCpApGpGpCpTpCpTpCpGpTpCOH (H1) |
| (16) | HOCpGpGpTpGpCpGpCpGpApCpGpApGpAOH (H2) |
| (17) | HOGpCpGpCpApCpCpGpCpApGpApCpTpGOH (I1) |
| (18) | HOCpTpApCpGpApTpApCpCpApGpTpCpTpGOH (I2) |
| (19) | HOGpTpApTpCpGpTpApGpApCpGpApApTpGOH (J1) |
| (20) | HOGpApApApApCpApGpCpApTpTpCpGpTOH (J2) |
| (21) | HOCpTpGpTpTpTpTpCpGpTpTpCpTpTpTpGOH (K1) |
| (22) | HOGpGpApGpApTpCpGpCpApApGpApApCOH (K2) |
| (23) | HOCpGpApTpCpTpCpCpGpCpCpGpTpCpTOH (L1) |
| (24) | HOTpApApApCpTpTpCpCpApGpApCpGpGpCOH (L2') |
| (25) | HOGpGpApApGpTpTpTpApCpTpGpTpGpCpTOH (M1') |
| (26) | HOTpTpCpApGpTpGpGpApGpCpApCpApGOH (M2) |
| (27) | HOCpCpApCpTpGpApApGpCpCpApGpCpAOH (N1) |
| (28) | HOGpCpGpGpApTpTpTpGpCpTpGpGpCOH (N2) |
| (29) | HOApApApTpCpCpGpCpGpTpGpApTpApGOH (O1) |
| (30) | HOGpApTpCpCpTpApTpCpApCOH (O2) |

The successive coupling reaction is shown in formula 1.

Mono(or di, or tri)mer (I) can be prepared by the Hirose's method [T. Hirose, PROTEIN, NUCLEIC ACID AND ENZYME ISSN, 25, 225(1980), published in Japan], and coupling can be carried out on cellulose by a phosphotriester method [R. Crea et al, Nucleic Acid Research 8, 2331(1980) and M. L. Duckworth et al, Nucleic Acid Research, 9, 1691(1981)].

Particularly, the synthetic methods will now be illustrated with reference to the synthesis of the hexadecanucleotide HOApApApCpCpGpApCpCpGpGpCpTpApTpGOH (G1) described in Example 1. The flow chart of the synthesis of the hexadecanucleotide G1 is shown in formula 2.

(ii) Hybridization and ligation of chemically synthesized oligonucleotide:

The oligonucleotides are hybridized and ligated in a series of steps, in order to minimize the possibilities for undesirable interactions as shown in formula 3. In formula 3, an oligonucleotide is illustrated with •—(• means 5'-phosphorylated end), and blocked oligonucleotides are illustrated, for example, •—▲—(▲means ligated position). Ligation is conducted in the presence of T4 DNA ligase.

Oligonucleotides A1, B1 and A2; C1, B2 and C2; D1, E1 and D2; F1, E2, and F2; G1, H1, and G2; I1, H2 and I2; J1, K1 and J2; L1, K2 and L2'; M1', N1 and M2 and O1 , N2 and O2 were hybridized and ligated to give Blocks 1 to 10, respectively. In this case Blocks 1 and 10 which were obtained from oligonucleotides A1, B1 and A2, and O1, N2 and O2, respectively, hybridized and ligated each other to form dimers. Blocks 2 and 3; 4 and 5, 6 and 7, 8 and 9 were hybridized and ligated to give Blocks 11, 12, 13 and 14, respectively. Blocks 11 and 12; 13 and 14 were hybridized and ligated to form Blocks 15 and 16, respectively. Blocks 1, 15, 16 and 10 were hybridized and ligated, and thus obtained ligated mixture was cleaved by EcoRI and BamHI to give an objective polynucleotide $^{59}$Val-IGF-I gene.

(2) Molecular cloning of the $^{59}$Val-IGF-I gene:

In order to clone the $^{59}$Val-IGF-I gene, it is inserted into an appropriate plasmid, cloning vector, having suitable enzyme recognition sites in which the $^{59}$Val-IGF-I gene can be inserted.

As a suitable embodiment of this invention $^{59}$Val-IGF-I gene synthesized for the expression in E. coli was inserted into a plasmid originated in E. coli (e.g. pBR322, pBR325, etc.) and cloning was conduced.

For example, in case using a plasmid pBR322 (commercially available) having EcoRI and BamHI sites, as shown in FIG. 4, the plasmid was cleaved by EcoRI and BamHI. In this case the plasmid has ampicillin resistance code (it is indicated by Amp) on the longer fragment when cleved by EcoRI and BamHI, and tetracycline resistance code (it is indicated by Tet) vanishes in consequence of the cleavage of BamHI site. The longer fragment of EcoRI, BamHI-cleaved plasmid pBR322 was purified by electroelution, hybridized and ligated with a large excess of the $^{59}$Val-IGF-I gene using T4 DNA ligase. Thus obtained mixture was transformed into E. coli HB101 (ATCC 33694). The plasmid was isolated from one of the obtained several ampicillin resistant and tetracyline sensitive transformants and confirmed to contain $^{59}$Val-IGF-I gene by digestion with restriction enzyme and electrophoresis. This process is shown in FIG. 4. The thus obtained plasmid is named plasmid pSdV2.

(3) Sequence of $^{59}$Val-IGF-I gene is plasmid pSdV2: The Maxam-Gilbert method can be used.

For the sequencing of $^{59}$Val-IGF-I gene, plasmid pSdV2 was digested with EcoRI and then treated with AMV reverse transcriptase in the presence of $\alpha$-$^{32}$P-ATP. The linear plasmid labeled with $^{32}$P was digested with BamHI to give two fragments (224 bp, 4.0 kbp). The smaller fragment (224 bp) was analysed by the usual Maxam-Gilbert method [A. Maxan and W. Gilbert, Proc. Natl. Acad. Sci. USA 74, 560 (1977)]. On the other hand, plasmid pSdV2 was digested with BamHI firstly, and then labeled with $^{32}$P as described above. The linear plasmid was digested with EcoRI to give two fragments (224 bp, 4.0 kbp). The smaller fragment (224 bp) was analysed by the Maxam-Gilbert method. The results of sequencing from both side of $^{59}$Val-IGF-I gene were agreed with the designed $^{59}$Val-IGF-I gene.

[2]

PREPARATION AND CLONING OF A RPOMOTER GENE

To obtain fused $^{59}$Val-IGF-I fron a host organism, a promoter gene was designed.

A promoter gene obtained by such a criteria is inserted into a plasmid in a style that the promoter gene is located upstream of and adjacent to a gene coding for $^{59}$Val-IGF-I or fused $^{59}$Val-IGF-I.

As a suitable embodiment of this invention a synthetic trp promoter I gene or synthetic trp promoter II gene were prepared.

(1) Preparation and cloning of a synthetic trp promoter I gene:

It was in fact decided to synthesize a molecule 107 bp by making 14 synthetic oligonucleotide blocks, which will be assembled by single-strand overlaps to give the complete double stranded nucleotide sequence.

```
                     EcoRI*
5'-AATTTGCCGACATCATAACGGTTCTGGCAAATATTCTGAAATGAGC-
3'-     ACGGCTGTAGTATTGCCAAGACCGTTTATAAGACTTTACTCG-

TGTTGACAATTAATCATCGAACTAGTTAACTAGTACGCAAGTTCACGTAAA-
ACAACTGTTAATTAGTAGCTTGATCAATTGATCATGCGTTCAAGTGCATTT-

EcoRI
                     AAGGGTATCG-3'
                     TTCCCATAGCTTAA-5'
```

(i) Synthesis of oligonucleotides:
The oligonucleotide blocks are as follows:

| | |
|---|---|
| (1) | HOApApTpTpTpGpCpCpGpApCpAOH (A) |
| (2) | HOCpGpTpTpApTpGpApTpGpTpCpGpGpCpAOH (B) |
| (3) | HOTpCpApTpApApCpGpGpTpTpCpTpGpGpCOH (C) |
| (4) | HOGpApApTpApTpTpTpGpCpCpApGpApApCOH (D) |
| (5) | HOApApApTpApTpTpCpTpGpApApApTpGpAOH (E) |
| (6) | HOTpCpApApCpApGpCpTpCpApTpTpTpCpAOH (F) |
| (7) | HOGpCpTpGpTpTpGpApCpApApTpTpApApTOH (G) |
| (8) | HOGpTpTpCpGpApTpGpApTpTpApApTpTpGOH (H) |
| (9) | HOCpApTpCpGpApApCpTpApGpTpTpApApCOH (I) |
| (10) | HOGpCpGpTpApCpTpApGpTpTpApApCpTpAOH (J) |
| (11) | HOTpApGpTpApCpGpCpApApGpTpTpCpApCOH (K) |
| (12) | HOCpTpTpTpTpApCpGpTpGpApApCpTpTOH (L) |
| (13). | HOGpTpApApApApApGpGpGpTpApTpCpGOH (M) |
| (14) | HOApApTpTpCpGpApTpApCpCOH (N) |

The synthetic method will now be illustrated with reference to the synthesis of hexadecanucleotide HOApApApCpCpGpApCpCpGpGpCpTpApT-pGOH (G1) mentioned above.

(ii) Ligation of chemically synthesized oligonucleotide:

The oligonucleotides were hybridized and ligated according to a similar manner to that of a $^{59}$Val-IGF-I gene as shown in formula 5.

(iii) Molecular cloning of the synthetic trp promotor I gene:

In order to clone the synthetic trp promotor I gene, the synthetic trp promotor gene is inserted to an appropriate plasmid having suitable enzyme recognition sites in to which the synthetic trp promoter I gene can be inserted. As a suitable embodiment of this invention, cloning was conducted by using a plasmid pBR325 (commercially available) as shown in formula 6. The plasmid pBR325 was cleaved with EcoRI, and the synthetic trp promoter I gene was inserted thereto. Thus obtained plasmid is named plasmid pST-1. The plasmid pST-1 was tranformed into *E. coli* HB101.

(2) Preparation of synthetic trp promoter II gene:

To insert the synthetic trp promoter I described above in a correct direction into a plasmid, following type of a synthetic promoter, synthetic trp promoter II, having a certain length of base pair chain following EcoRI of synthetic trp promoter I and BamHI site at 3'-end was prepared.

It was in fact decided to synthesize a molecule having 163 bp by making 22 synthetic oligonucleotide blocks, which will be assemble by single-strand overlaps to give the complete double-stranded nucleotide sequence.

-continued

| | |
|---|---|
| (2) | HOGpGpTpTpGpTpApApGpApApCpTpTpCpTOH (SB) |
| (3) | HOTpTpTpGpGpApApGpApCpTpTpTOH (SC) |
| (4) | HOCpApCpTpTpCpGpTpGpTpTpGpApTpApGOH (SD) |
| (5) | HOTpTpApCpApApCpCpApGpCpCpApTpGOH (SE) |
| (6) | HOCpCpApApApApGpApApGpTpTpCOH (SF) |
| (7) | HOCpGpApApGpTpGpApApApGpTpCpTpTOH (SG) |
| (8) | HOGpApTpCpCpTpApTpCpApApCpAOH (SH) |

The synthetic method will now be illustrated with reference to the synthesis of hexadecanucleotide HOApApApCpCpGpApCpCpGpGpCpTpGOH (G1) mentioned above.

(ii) Hybridization and ligation of chemically synthesized oligonucleotides:

The oligonucleotide A to N and SA to SH were hybridized and ligated according to a similar manner to that of a $^{59}$Val-IGF-I gene as shown in formula 7.

(3) Molecular cloning of synthetic trp promoter II gene:

The synthetic trp promoter II gene was inserted into a plasmid. As a suitable embodiment of this invention, the synthetic trp promoter II was inserted into a plasmid pBR322 by cleaving the sites with EcoRI and BamHI as shown in formula 8. Thus obtained plasmid is named as plasmid pTrpEB7.

[3]

PREPARATION AND CLONING OF PROTEIN PEPTIDE LH GENE

As a suitable example of a protective peptide which can be fused with $^{59}$Val-IGF-I, protein peptide LH has been prepared.

```
    EcoRI*
5'-AATTTGCCGACATCATAACGGTTCTGGCAAATATTCTGAAATGAGC-
3'-     ACGGCTGTAGTATTGCCAAGACCGTTTATAAGACTTTACTCG-

TGTTGACAATTAATCATCGAACTAGTTAACTAGRACGCAAGTTCACGTAAA-
ACAACTGTTAATTAGTAGCTTGATCAATTGATCATGCGTTCAAGTGCATTT-

EcoRI
AAGGGTATCGAATTCATGGCTGGTTGTAAGAACTTCTTTTGGAAGACTTTC-
TTCCCATAGCTTAAGTACCGACCAACATTCTTGAAGAAAACCTTCTGAAAG-

BamHI
ACTTCGTGTTGATAG-3'
TGAAGCACAACTATCCTAG-5'
```

(i) Synthesis of oligonucleotides:
Eight oligonucleotide was further synthesized.

(1) HOApApTpTpCpApTpGpGpCpTOH (SA)

(1) Preparation of protein peptide LH gene:

It was in fact decided to synthesize a molecule 233 bp by making 32 synthetic oligonucleotide blocks, which will be assemble by single-strand overlaps to give the complete double stranded nucleotide sequence.

```
                        1
         EcoRI  Met  Cys  Tyr  Cys  Gln  Asp  Pro  Tyr
Coding:    5'-AATTC—ATG—TGT—TAC—TGC—CAG—GAC—CCA—TAT—
Noncoding: 3'-       G—TAC—ACA—ATG—ACG—GTC—CTG—GGT—ATA—

10                                               20
Val  Lys  Glu  Ala  Glu  Asn  Leu  Lys  Lys  Tyr  Phe  Asn  Ala  Gly
GTA—AAA—GAA—GCA—GAA—AAC—CTT—AAG—AAA—TAC—TTT—AAT—GCA—GGT—
CAT—TTT—CTT—CGT—CTT—TTG—GAA—TTC—TTT—ATG—AAA—TTA—CGT—CCA—

30
His  Ser  Asp  Val  Ala  Asp  Asn  Gly  Thr  Leu  Phe  Leu  Gly  Ile
CAT—TCA—GAT—TGA—GCG—GAT—AAT—GGA—ACT—CTT—TTC—TTA—GGC—ATT—
```

-continued
GTA—AGT—CTA—CAT—CGC—CTA—TTA—CCT—TGA—GAA—AAG—AAT—CCG—TAA—

```
                                 40
Leu   Lys   Asn   Trp   Lys   Glu   Glu   Ser   Asp   Arg   Lys   Ile   Met   Gln
TTG—AAG—AAT—TGG—AAA—GAG—GAG—AGT—GAC—AGA—AAA—ATA—ATG—CAG—
AAC—TTC—TTA—ACC—TTT—CTC—CTC—TCA—CTG—TCT—TTT—TAT—TAC—GTC—

50                                                  HindIII    60
Ser   Gln   Ile   Val   Ser   Phe   Tyr   Phe   Lys   Leu   Phe   Lys   Asn   Phe
AGC—CAA—ATT—GTC—TCC—TTT—TAC—TTC—AAG—CTT—TTC—AAA—AAC—TTT—
TCG—GTT—TAA—CAG—AGG—AAA—ATG—AAG—TTC—GAA—AAG—TTT—TTG—AAA—

70
Lys   Asp   Asp   Gln   Ser   Ile   Gln   Lys   Ser   Val   Stop   Stop   BamHI
AAG—GAT—GAC—CAG—AGC—ATC—CAA—AAG—AGT—GTG—TAA—TGA—TAG
TTC—CTA—CTG—GTC—TCG—TAG—GTT—TTC—TCA—CAC—ATT—ACT—ATCCTAG
```

(i) Synthesis of oligonucleotides:
The oligonucleotide blocks are as follows:

| | |
|---|---|
| (1) | HOApApTpTpCpApTpGpTpGpTpTOH (a1) |
| (2) | HOApCpTpGpCpCpApGpGpApCpCpApTOH (a2) |
| (3) | HOApTpGpTpApApApApGpApApGpCpApGOH (a3) |
| (4) | HOTpGpGpCpApGpTpApApCpApCpApTpGOH (a4) |
| (5) | HOTpTpTpApCpApTpApTpGpGpGpTpCpCOH (a5) |
| (6) | HOApApGpTpTpTpTpCpTpGpCpTpTpCpTOH (a6) |
| (7) | HOApApApApCpCpTpTpApApGpApApApTpAOH (b1) |
| (8) | HOCpTpTpApApTpGpCpApGpGpTpCpAOH (b2) |
| (9) | HOTpTpCpApGpTpGpTpApGpCpGpGpAOH (b3) |
| (10) | HOApTpTpApApApGpTpApTpTpTpCpTpTOH (b4) |
| (11) | HOApTpCpTpGpApApTpGpApCpCpTpGpCOH (b5) |
| (12) | HOTpTpCpCpApTpTpApTpCpCpGpCpTpApCOH (b6) |
| (13) | HOTpApApTpGpGpApApCpTpCpTpTpTpTpCOH (c1) |
| (14) | HOTpTpApGpGpCpApTpTpTpGpApApGOH (c2) |
| (15) | HOApApTpTpGpGpApApApGpApGpGpApGOH (c3) |
| (16) | HOTpGpGpCpCpTpApApGpApApApApGpApGOH (c4) |
| (17) | HOTpCpCpApApTpTpCpTpTpCpApApApAOH (c5) |
| (18) | HOCpTpGpTpCpApCpTpCpTpCpCpTpCpTpTOH (c6) |
| (19) | HOApGpTpGpApCpApGpApApApApApTpAOH (d1) |
| (20) | HOApTpGpCpApGpApGpCpCpApApApTpTOH (d2) |
| (21) | HOGpTpCpTpCpCpTpTpTpTpApCpTpTOH (d3) |
| (22) | HOCpTpCpTpGpCpApTpTpApTpTpTpTOH (d4) |
| (23) | HOApGpGpApGpApCpApApTpTpTpGpGOH (d5) |
| (24) | HOApApApGpCpTpTpGpApApGpTpApApAOH (d6) |
| (25) | HOCpApApGpCpTpTpTpTpCpApApApApAOH (e1) |
| (26) | HOCpTpTpApApGpGpApTpGpApCpCpAOH (e2) |
| (27) | HOGpApGpCpApTpCpCpApApApApGpApGOH (e3) |
| (28) | HOCpCpTpTpApApApApGpTpTpTpTpGpAOH (e4) |
| (29) | HOGpGpApTpGpCpTpCpTpGpGpTpCpApTOH (e5) |
| (30) | HOTpGpTpGpTpApApTpGpApTpApGOH (11) |
| (31) | HOTpApCpApCpApCpTpCpTpTpTpTOH (12) |
| (32) | HOGpApTpCpCpTpApTpCpApTOH (13) |

(ii) Hybridization and ligation of chemically synthesized oligonucleotides:

The oligonucleotides a1 to 13 were hybridized and ligated according to a similar manner to that of $^{59}$Val-IGF-I gene as shown in formula 9.

(2) Molecular cloning of protein peptide LH gene:

Protein peptide LH gene was inserted into a plasmid. As a suitable embodiment of this invention, protein peptide LH gene was inserted into a plasmid pBR322 by cleaving the sites with EcoRI and BamHI as shown in formula 10. The thus obtained plasmid is named plasmid pLH107.

[4]

CONSTRUCTION OF EXPRESSION VECTOR OF $^{59}$Val-IGF-I $^{59}$Val-IGF-I gene is inserted to a plasmid containing a promoter gene, and $^{59}$Val-IGF-I gene is transformed into a host organism.

As a suitable embodiment of this invention, the following recombinant plasmids were established to express $^{59}$Val-IGF-I gene in E. coli.

(1) Construction of recombinant plasmid pSdV2trp:

Trp promoter plasmid pST-1 prepared above was digested with EcoRI and $^{59}$Val-IGF-I gene was inserted to the resulted large fragment. Thus obtained recombinant plasmid was named a plasmid pSdV2trp which was transformed into E. coli, for example E. coli HB101. This process is shown in formula 11.

(2) Construction of recombinant plasmid pSdV2-322trp:

Trp promoter plasmid pTrpEB7 was digested with EcoRI and BamHI, the resulted large fragment (4.1 kbp) was separated by agarose gel electrophoresis. On the other hand, the $^{59}$Val-IGF-I gene was isolated from plasmid pSdV2, and ligated with the above promoter vector (4.1 kbp). The mixtures was transformed into E. coli HB101. The plasmid was isolated from one of the obtained ampicillin resistant and tetracycline sensitive transformants, and confirmed to contain $^{59}$Val-IGF-I gene by digestion with restriction enzyme and electrophoresis. The thus obtained plasmid is named plasmid pSdV2-322trp and the E. coli containing the plasmid is named as E. coli F-2. This process is shown in formula 12.

[5]

SEQUENCING OF $^{59}$Val-IGF-I GENE AND A PROMOTER GENE

The Maxam Gilbert method can be used.

(1) Sequence of $^{59}$Val-IGF-I gene and synthetic trp promoter I gene in plasmid pSdV2trp:

Sequence of $^{59}$Val-IGF-I and the synthetic trp promoter I in plasmid pSdV2trp was determined in a similar manner to that of plasmid pSdV2-322trp described below.

(2) Sequence of $^{59}$Val-IGF-I gene and synthetic trp promoter I gene in plasmid pSdV2-322trp:

For sequencing of $^{59}$Val-IGF-I and the synthetic trp promoter I gene, plasmid pSdV2-322trp was digested with EcoRI and treated with BAP (bacteria alkaline phosphatase), and then treated with T4 polynucleotide kinase in the presence of $\gamma$-$^{32}$P-ATP. The labeled DNA was digested with HinfI to give two fragments (110 bp and 480 bp). These fragments were analyzed by the Maxam-Gilbert method. (A. Mazam and W. Gilbert, Proc. Natl. Acad. Sci. USA 74, 560 (1977)). The resulting sequence coincided with the designed sequence of 59Val-IGF-I gene and the synthetic promoter I gene.

[6]

CONSTRUCTION OF EXPRESSION VECTOR OF FUSED 59Val-IGF-I

A gene coding for fused 59Val-IGF-I which comprises linking a gene coding for a protective peptide with 59Val-IGF-I gene with or without a linker upstream of the 59Val-IGF-I gene was prepared.

In this process, a protein peptide having methionine as the last amino acid is fused with 59Val-IGF-I.

Thus obtained fused 59Val-IGF-I is as follows.

59Val-IGF-I fused with the protein peptide through methionine of the protein peptide.

The present invention also relates to expression vectors of a gene coding such as fused 59Val-IGF-I.

(1) Construction of expression vector of protein peptide LH gene:

As a suitable embodiment of this invention, the following types of expression vector of a gene coding for 59Val-IGF-I fused with protein peptide LH were prepared.

The present invention also relates to a process for the invention of such a gene which is constructed by linking a gene coding for a protective peptide with the 59Val-IGF-I gene upstream of said 59Val-IGF-I gene with or without a linker.

Protein peptide LH gene is inserted into a plasmid containing a promoter gene, and protein peptide LH gene is transformed into a host organism.

As a suitable embodiment of this invention, the following recombinant plasmid was established to express protein peptide LH gene in *E. coli*.

Trp promoter II plasmid pTrpEB7 was digested with EcoRI and BamHI, the resulting large fragment (4.1 kbp) was separated by agarose gel electrophoresis. On the other hand, protein peptide LH gene was isolated from plasmid pLH107, and ligated with the above promoter vector (4.1 kbp). The mixture was transformed into *E. coli* HB101. The plasmid was isolated from one of the obtained ampicillin resistant and tetracycline sensitive transformants, and confirmed to contain protein peptide LH gene by digestion with restriction enzyme and electrophoresis. The thus obtained plasmid is named plasmid pLHtrp. This process is shown in formula 13.

A plasmid pLHtrp prepared above was digested with HindIII and BamHI, the resultant large fragment was separated by preparative agarose gel electrophoresis. On the other hand, 59Val-IGF-I gene was isolated from plasmid pSdV2 prepared above with EcoRI and BamHI digestion and oligonucleotides m1 and m2 were ligated upstream of and adjacent to it as a linker. Thus obtained 59Val-IGF-I gene with linker was ligated with the above large fragment of plasmid pLHtrp. The mixture was transformed into *E. coli* HB101. The plasmid was isolated from one of the obtained ampicillin resistant and tetracycline sensitive transformants, and confirmed to contain a gene coding for 59Val-IGF-I fused with protein peptide LH by digestion with restriction enzyme and electrophoresis. The thus obtained plasmid is named plasmid pLHSdVtrp. This process is shown in formula 14.

Thus obtained gene coding for 59Val-IGF-I fused with protein peptide LH is as follows:

```
                 1
         EcoRI   Met   Cys   Tyr   Cys   Gln   Asp   Pro   Tyr
Coding:    5'-AATTC—ATG—TGT—TAC—TGC—CAG—GAC—CCA—TAT—
Noncoding:      3'-G—TAC—ACA—ATG—ACG—GTC—CTG—GGT—ATA—

10                                              20
Val   Lys   Glu   Ala   Glu   Asn   Leu   Lys   Lys   Tyr   Phe   Asn   Ala   Gly
GTA—AAA—GAA—GCA—GAA—AAC—CTT—AAG—AAA—TAC—TTT—AAT—GCA—GGT—
CAT—TTT—CTT—CGT—CTT—TTG—GAA—TTC—TTT—ATG—AAA—TTA—CGT—CCA—

30
His   Ser   Asp   Val   Ala   Asp   Asn   Gly   Thr   Leu   Phe   Leu   Gly   Ile
CAT—TCA—GAT—GTA—GCG—GAT—AAT—GGA—ACT—CTT—TTC—TTA—GGC—ATT—
GTA—AGT—CTA—CAT—CGC—CTA—TTA—CCT—TGA—GAA—AAG—AAT—CCG—TAA—

40
Leu   Lys   Asn   Trp   Lys   Glu   Glu   Ser   Asp   Arg   Lys   Ile   Met   Gln
TTG—AAG—AAT—TGG—AAA—GAG—GAG—AGT—GAC—AGA—AAA—ATA—ATG—CAG—
AAC—TTC—TTA—ACC—TTT—CTC—CTC—TCA—CTG—TCT—TTT—TAT—TAC—GTC—

50                                          HindIII    60
Ser   Gln   Ile   Val   Ser   Phe   Tyr   Phe   Lys   Leu   Glu   Val   Lys   His
AGC—CAA—ATT—GTC—TCC—TTT—TAC—TTC—AAG—CTT—GAA—GTA—AAA—CAT—
TCG—GTT—TAA—CAG—AGG—AAA—ATG—AAG—TTC—GAA—CTT—CAT—TTT—GTA—

70
Glu   Phe   Met   Gly   Pro   Glu   Thr   Leu   Cys   Gly   Ala   Glu   Leu   Val
GAA—TTC—ATG—GGT—CCT—GAA—ACT—CTG—TGC—GGC—GCT—GAA—CTG—GTT—
CTT—AAG—TAC—CCA—GGA—CTT—TGA—GAC—ACG—CCG—CGA—CTT—GAC—CAA—
```

```
            80                                           90
Asp  Ala  Leu  Gln  Phe  Val  Cys  Gly  Asp  Arg  Gly  Phe  Tyr  Phe
GAC—GCT—CTG—CAA—TTT—GTA—TGT—GGT—GAT—CGT—GGT—TTC—TAC—TTC—
CTG—CGA—GAC—GTT—AAA—CAT—ACA—CCA—CTA—GCA—CCA—AAG—ATG—AAG—

100
Asn  Lys  Pro  Thr  Gly  Tyr  Gly  Ser  Ser  Ser  Arg  Arg  Ala  Pro
AAC—AAA—CCG—ACC—GGC—TAT—GGC—TCC—AGC—TCT—CGT—CGC—GCA—CCG—
TTG—TTT—GGC—TGG—CCG—ATA—CCG—AGG—TCG—AGA—GCA—GCG—CGT—GGC—

110
Gln  Thr  Gly  Ile  Val  Asp  Glu  Cys  Cys  Phe  Arg  Ser  Cys  Asp
CAG—ACT—GGT—ATC—GTA—GAC—GAA—TGC—TGT—TTT—CGT—TCT—TGC—GAT—
GTC—TGA—CCA—TAG—CAT—CTG—CTT—ACG—ACA—AAA—GCA—AGA—ACG—CTA—

120                                                   130
Leu  Arg  Arg  Leu  Glu  Val  Tyr  Cys  Ala  Pro  Leu  Lys  Pro  Ala
CTC—CGC—CGT—CTG—GAA—GTT—TAC—TGT—GCT—CCA—CTG—AAG—CCA—GCA—
GAG—GCG—GCA—GAC—CTT—CAA—ATG—ACA—CGA—GGT—GAC—TTC—GGT—CGT—

Lys  Ser  Ala  Stop  stop  BamHI
AAA—TCC—GCG—TGA—TAG—3'
TTT—AGG—CGC—ACT—ATC—CTAG—5', and
``` a gene coding for $^{59}$Val—IGF—I fused with protein peptide LH is as follows:

```
             1
           Cys  Tyr  Cys  Gln  Asp  Pro  Tyr
Coding:    TGT—TAC—TGC—CAG—GAC—CCA—TAT—
Noncoding: ACA—ATG—ACG—GTC—CTG—GGT—ATA—

10                                        20
Val  Lys  Glu  Ala  Glu  Asn  Leu  Lys  Lys  Tyr  Phe  Asn  Ala  Gly
GTA—AAA—GAA—GCA—GAA—AAC—CTT—AAG—AAA—TAC—TTT—AAT—GCA—GGT—
CAT—TTT—CTT—CGT—CTT—TTG—GAA—TTC—TTT—ATG—AAA—TTA—CGT—CCA—

30
His  Ser  Asp  Val  Ala  Asp  Asn  Gly  Thr  Leu  Phe  Leu  Gly  Ile
CAT—TCA—GAT—GTA—GCG—GAT—AAT—GGA—ACT—CTT—TTC—TTA—GGC—ATT—
GTA—AGT—CTA—CAT—CGC—CTA—TTA—CCT—TGA—GAA—AAG—AAT—CCG—TAA—

40
Leu  Lys  Asn  Trp  Lys  Glu  Glu  Ser  Asp  Arg  Lys  Ile  Met  Gln
TTG—AAG—AAT—TGG—AAA—GAG—GAG—AGT—GAC—AGA—AAA—ATA—ATG—CAG—
AAC—TTC—TTA—ACC—TTT—CTC—CTC—TCA—CTG—TCT—TTT—TAT—TAC—GTC—

50                                    HindIII   60
Ser  Gln  Ile  Val  Ser  Phe  Tyr  Phe  Lys  Leu  Glu  Val  Lys  His—
AGC—CAA—ATT—GTC—TCC—TTT—TAC—TTC—AAG—CTT—GAA—GTA—AAA—CAT—
TCG—GTT—TAA—CAG—AGG—AAA—ATG—AAG—TTC—GAA—CTT—CAT—TTT—GTA—

70
Glu  Phe  Met  Gly  Pro  Glu  Thr  Leu  Cys  Gly  Ala  Glu  Leu  Val
GAA—TTC—ATG—GGT—CCT—GAA—ACT—CTG—TGC—GGC—GCT—GAA—CTG—GTT—
CTT—AAG—TAC—CCA—GGA—CTT—TGA—GAC—ACG—CCG—CGA—CTT—GAC—CAA—
```

-continued

```
                80                                                         90
Asp  Ala  Leu  Gln  Phe  Val  Cys  Gly  Asp  Arg  Gly  Phe  Tyr  Phe
GAC—GCT—CTG—CAA—TTT—GTA—TGT—GGT—GAT—CGT—GGT—TTC—TAC—TTC—
CTG—CGA—GAC—GTT—AAA—CAT—ACA—CCA—CTA—GCA—CCA—AAG—ATG—AAG—

100
Asn  Lys  Pro  Thr  Gly  Tyr  Gly  Ser  Ser  Ser  Arg  Arg  Ala  Pro
AAC—AAA—CCG—ACC—GGC—TAT—GGC—TCC—AGC—TCT—CGT—CGC—GCA—CCG—
TTG—TTT—GGC—TGG—CCG—ATA—CCG—AGG—TCG—AGA—GCA—GCG—CGT—GGC—

110
Gln  Thr  Gly  Ile  Val  Asp  Glu  Cys  Cys  Phe  Arg  Ser  Cys  Asp
CAG—ACT—GGT—ATC—GTA—GAC—GAA—TGC—TGT—TTT—CGT—TCT—TGC—GAT—
GTC—TGA—CCA—TAG—CAT—CTG—CTT—ACG—ACA—AAA—GCA—AGA—ACG—CTA—

120                                                   130
Leu  Arg  Arg  Leu  Glu  Val  Tyr  Cys  Ala  Pro  Leu  Lys  Pro  Ala
CTC—CGC—CGT—CTG—GAA—GTT—TAC—TGT—GCT—CCA—CTG—AAG—CCA—GCA—
GAG—GCG—GCA—GAC—CTT—CAA—ATG—ACA—CGA—GGT—GAC—TTC—GGT—CGT—

Lys  Ser  Ala
AAA—TCC—GCG—3′
TTT—AGG—CGC—5′
```

(2) Construction of expression vector of a gene coding for $^{59}$Val-IGF-I fused with protein peptide LH having terminator downstream of and adjacent to $^{59}$Val-IGF-I gene:

A terminator may be inserted downstream of and adjacent to said $^{59}$Val-IGF-I gene.

Suitable "terminator" may include a gene coding for suitable restriction enzyme recognition sites.

(a) Synthesis of oligonucleotides:

Fourteen oligonucleotides were further synthesized:

(1) HOGpApTpCpCpTpCpGpApGpApTpCpApAOH (A′)
(2) HOGpCpCpTpTpTpApApTpTpCpApTpCpTpCpGpApGOH (B′)
(3) HOTpTpApApApGpGpCpTpCpCpTpTpTpTpGpGpAOH (C′)
(4) HOApApApApApGpGpCpTpCpCpApApApApGpGpAOH (D′)
(5) HOGpCpCpTpTpTpTpTpTpTpTpTpTpGOH (E′)
(6) HOTpCpGpApCpApApApApAOH (F′)
(7) HOGpApTpCpCpTpCpGpApGpCpTOH (G′)
(8) HOGpTpTpTpApApTpCpApGpCpTpCpGpApGOH (H′)
(9) HOGpApTpTpApApApCpCpGpApApTpCpApAOH (I′)
(10) HOGpCpCpTpTpTpApApTpTpGpApTpTpCpGOH (J′)
(11) HOGpCpCpTpTpTpTpTpTpTpTpTpTOH (K′)
(12) HOTpCpTpCpCpApApApApAOH (L′)
(13) HOGpGpApGpApCpApApCpGOH (M′)
(14) HOTpCpGpApCpGpTpTpGOH (N′)

(b) Ligation of chemically synthesized oligonucleotides:

(i) Terminator S (terS):

The oligonucleotides A′ to F′ were hybridized and ligated according to a similar manner to that of $^{59}$Val-IGF-I to give terminator S as shown in formula 15.

(ii) Terminator L (terL):

The ologonucleotides C′, D′, and G′ to N′ were hybridized and ligated according to a similar manner to that of $^{59}$Val-IGF-I to give terminator L as shown in formula 16.

(c) Molecular cloning of terminator S and terminator L:

Terminator S and terminator L were inserted into the plasmid pLHSdVtrp downstream of and adjacent to $^{59}$Val-IGF-I gene, respectively. These processes are shown in formula 17 and 18.

(3) Construction of expression vector of $^{59}$Val-IGF-I fused with $\beta$-galactosidase:

(a) Construction of recombinant plasmid pSdV2-lac:

Plasmid pSdV2-lac was constructed by the method described in Example 22.

(b) Construction of recombinant plasmid pSdV2-NT49:

Plasmid pSdV2-NT49 was constructed by the method described in Example 24.

(c) A gene coding for $^{59}$Val-IGF-I fused with $\beta$-galactosidase:

A gene coding for $^{59}$Val-IGF-I fused with $\beta$-galactosidase is as follows:

```
1                                                 10
Thr  Met  Ile  Thr  Asp  Ser  Leu  Ala  Val  Val  Leu  Gln  Arg  Arg
ACC—ATG—ATT—ACG—GAT—TCA—CTG—GCC—GTC—GTT—TTA—CAA—CGT—CGT—
TGG—TAC—TAA—TGC—CTA—AGT—GAC—CGG—CAG—CAA—AAT—GTT—GCA—GCA—
```

-continued

```
                        20
Asp  Trp  Glu  Asn  Pro  Gly  Val  Thr  Gln  Leu  Asn  Arg  Leu  Ala
GAC—TGG—GAA—AAC—CCT— GGC—GTT—ACC—CAA—CTT— AAT—CGC—CTT— GCA—
CTG—ACC—CTT— TTG—GGA—CCG—CAA—TGG—GTT—GAA—TTA—GCG—GAA—CGT—

30                                          40
Ala  His  Pro  Pro  Phe  Ala  Ser  Trp  Arg  Asn  Ser  Glu  Glu  Ala
GCA—CAT—CCC— CCT— TTC— GCC—AGC—TGG—CGT—AAT—AGC—GAA—GAG—GCC—
CGT—GTA—GGG—GGA—AAG—CGG—TCG—ACC—GCA—TTA—TCG—CTT— CTC— CGG—

50
Arg  Thr  Asp  Arg  Pro  Ser  Gln  Gln  Leu  Arg  Ser  Leu  Asn  Gly
CGC—ACC—GAT—CGC—CCT— TCC— CAA—CAG—TTG—CGC—AGC—CTG—AAT—GGC—
GCG—TGG—CTA—GCG—GGA—AGG—GTT—GTC—AAC—GCG—TCG—GAC—TTA—CCG—

60                                              70
Glu  Trp  Arg  Phe  Ala  Trp  Phe  Pro  Ala  Pro  Glu  Ala  Val  Pro
GAA—TGG—CGC—TTT— GCC—TGG—TTT— CCG—GCA—CCA—GAA—GCG—GTG—CCG—
CTT— ACC—GCG—AAA—CGG—ACC—AAA—GGC—CGT—GGT—CTT— CGC—CAC—GGC—

80
Glu  Ser  Trp  Leu  Glu  Cys  Asp  Leu  Pro  Glu  Ala  Asp  Thr  Val
GAA—AGC—TGG—CTG—GAG—TGC—GAT—CTT— CCT— GAG—GCC—GAT—ACT—GTC—
CTT— TCG—ACC—GAC—CTC— ACG—CTA—GAA—GGA—CTC— CGG—CTA—TGA—CAG—

90
Val  Val  Pro  Ser  Asn  Trp  Gln  Met  His  Gly  Tyr  Asp  Ala  Pro
GTC—GCT—CCC— TCA—AAC—TGG—CAG—ATG—CAC—GGT—TAC—GAT—GCG—CCC—
CAG—CGA—GGG—AGT—TTG—ACC—GTC—TAC—GTG—CCA—ATG—CTA—CGC—GGG—

100                                          110
Ile  Tyr  Thr  Asn  Val  Thr  Tyr  Pro  Ile  Thr  Val  Asn  Pro  Pro
ATC—TAC—ACC—AAC—GTA—ACC—TAT—CCC— ATT—ACG—GTC—AAT—CCG—CCG—
TAG—ATG—TGG—TTG—CAT—TGG—ATA—GGG—TAA—TGC—CAG—TTA—GGC—GGC—

120
Phe  Val  Pro  Thr  Glu  Asn  Pro  Thr  Gly  Cys  Tyr  Ser  Leu  Thr
TTT— GTT—CCC— ACG—GAG—AAT—CCG—ACG—GGT—TGT—TAC—TCG—CTC— ACA—
AAA—CAA—GGG—TGC—CTC— TTA—GGC—TGC—CCA—ACA—ATG—AGC—GAG—TGT—

130                                              140
Phe  Asn  Val  Asp  Glu  Ser  Trp  Leu  Gln  Glu  Gly  Gln  Thr  Arg
TTT— AAT—GTT—GAT—GAA—AGC—TGG—CTA—CAG—GAA—GGC—CAG—ACG—CGA—
AAA—TTA—CAA—CTA—CTT— TCG—ACC—GAT—GTC—CTT— CCG—GTC—TGC—GCT—

150
Ile  Ile  Phe  Asp  Gly  Val  Asn  Ser  Ala  Phe  His  Leu  Trp  Cys
ATT—ATT—TTT— GAT—GGC—GTT—AAC—TCG—GCG—TTT— CAT—CTG—TGG—TGC—
TAA—TAA—AAA—CTA—CCG—CAA—TTG—AGC—CGC—AAA—GTA—GAC—ACC—ACG—

160
Asn  Gly  Arg  Trp  Val  Gly  Tyr  Gly  Gln  Asp  Ser  Arg  Leu  Pro
AAC—GGG—CGC—TGG—GTC—GGT—TAC—GGC—CAG—GAC—AGT—CGT—TTG—CCG—
TTG—CCC— GCG—ACC—CAG—CCA—ATG—CCG—GTC—CTG—TCA—GCA—AAC—GGC—

170                                          180
Ser  Glu  Phe  Asp  Leu  Ser  Ala  Phe  Leu  Arg  Ala  Gly  Glu  Asn
TCT— GAA—TTT— GAC—CTG—AGC—GCA—TTT— TTA—CGC—GCC—GGA—GAA—AAC—
AGA—CTT— AAA—CTG—GAC—TCG—CGT—AAA—AAT—GCG—CGG—CCT— CTT— TTG—
```

```
                                        190
Arg  Leu  Ala  Val  Met  Val  Leu  Arg  Trp  Ser  Asp  Gly  Ser  Tyr
CGC—CTC— GCG—GTG—ATG—GTG—CTG—CGT—TGG—AGT—GAC—GGC—AGT—TAT—
GCG—GAG—CGC—CAC—TAC—CAC—GAC—GCA—ACC—TCA—CTG—CCG—TCA—ATA—

200                                         210
Leu  Glu  Asp  Gln  Asp  Met  Trp  Arg  Met  Ser  Gly  Ile  Phe  Arg
CTG—GAA—GAT—CAG—GAT—ATG—TGG—CGG—ATG—AGC—GGC—ATT—TTC— CGT—
GAC—CTT— CTA—GTC—CTA—TAC—ACC—GCC—TAC—TCG—CCG—TAA—AAG—GCA—

220
Asp  Val  Ser  Leu  Leu  His  Lys  Pro  Thr  Thr  Gln  Ile  Ser  Asp
GAC—GTC—TCG—TTG—CTG—CAT—AAA—CCG—ACT—ACA—CAA—ATC—AGC—GAT—
CTG—CAG—AGC—AAC—GAC—GTA—TTT— GGC—TGA—TGT—GTT—TAC—TCG—CTA—

230
Phe  His  Val  Ala  Thr  Arg  Phe  Asn  Asp  Asp  Phe  Ser  Arg  Ala
TTC— CAT—GTT—GCC—ACT—CGC—TTT— AAT—GAT—GAT—TTC— AGC—CGC—GCT—
AAG—GTA—CAA—CGG—TGA—GCG—AAA—TTA—CTA—CTA—AAG—TCG—GCG—CGA—

240                                         250
Val  Leu  Glu  Ala  Glu  Val  Gln  Met  Cys  Gly  Glu  Leu  Arg  Asp
GTA—CTG—GAG—GCT—GAA—GTT—CAG—ATG—TGC—GGC—GAG—TTG—CGT—GAC—
CAT—GAC—CTC— CGA—CTT— CAA—GTC—TAC—ACG—CCG—CTC— AAC—GCA—CTG—

260
Tyr  Leu  Arg  Val  Thr  Val  Ser  Leu  Trp  Gln  Gly  Glu  Thr  Gln
TAC—CTA—CGG—GTA—ACA—GTT—TCT— TTA—TGG—CAG—GGT—GAA—ACG—CAG—
ATG—GAT—GCC—CAT—TGT—CAA—AGA—AAT—ACC—GTC—CCA—CTT— TGC—GTC—

270                                              280
Val  Ala  Ser  Gly  Thr  Ala  Pro  Phe  Gly  Gly  Glu  Ile  Ile  Asp
GTC—GCC—AGC—GGC—ACC—GCG—CCT— TTC— GGC—GGT—GAA—ATT—ATC—GAT—
CAG—CGG—TCG—CCG—TGG—CGC—GGA—AAG—CCG—CCA—CTT— TAA—TAG—CTA—

290
Glu  Arg  Gly  Gly  Tyr  Ala  Asp  Arg  Val  Thr  Leu  Arg  Leu  Asn
GAG—CGT—GGT—GGT—TAT—GCC—GAT—CGC—GTC—ACA—CTA—CGT—,CTG—AAC—
CTC— GCA—CCA—CCA—ATA—CGG—CTA—GCG—CAG—TGT—GAT—GCA—GAC—TTG—

300
Val  Glu  Asn  Pro  Lys  Leu  Trp  Ser  Ala  Glu  Ile  Pro  Asn  Leu
GTC—GAA—AAC—CCG—AAA—CTG—TGG—AGC—GCC—GAA—ATC—CCG—AAT—CTC—
CAG—CTT— TTG—GGC—TTT— GAC—ACC—TCG—CGG—CTT— TAG—GGC—TTA—GAG—

310                                         320
Tyr  Arg  Ala  Val  Val  Glu  Leu  His  Thr  Ala  Asp  Gly  Thr  Leu
TAT—CGT—GCG—GTG—GTT—GAA—CTG—CAC—ACC—GCC—GAC—GGC—ACG—CTG—
ATA—GCA—CGC—CAC—CAA—CTT— GAC—GTG—TGG—CGG—CTG—CCG—TGC—GAC—

330
Ile  Glu  Ala  Glu  Ala  Cys  Asp  Val  Gly  Phe  Arg  Glu  Val  Arg
ATT—GAA—GCA—GAA—GCC—TGC—GAT—GTC—GGT—TTC— CGC—GAG—GTG—CGC—
TAA—CTT— CGT—CTT— CGG—ACG—CTA—CAG—CCA—AAG—GCG—CTC— CAC—GCC—
```

-continued

```
                        340                                                         350
Ile   Glu   Asn   Gly   Leu   Leu   Leu   Leu   Asn   Gly   Lys   Pro   Leu   Leu
ATT—GAA—AAT—GGT—CTG—CTG—CTG—CTG—AAC—GGC—AAG—CCG—TTG—CTG—
TAA—CTT—TTA—CCA—GAC—GAC—GAC—GAC—TTG—CCG—TTC—GGC—AAC—GAC—

360
Ile   Arg   Gly   Val   Asn   Arg   His   Glu   His   His   Pro   Leu   His   Gly
ATT—CGA—GGC—GTT—AAC—CGT—CAC—GAG—CAT—CAT—CCT—CTG—CAT—GGT—
TAA—GCT—CCG—CAA—TTG—GCA—GTG—CTC—GTA—GTA—GGA—GAC—GTA—CCA—

370
Gln   Val   Met   Asp   Glu   Gln   Thr   Met   Val   Gln   Asp   Ile   Leu   Leu
CAG—GTC—ATG—GAT—GAG—CAG—ACG—ATG—GTG—CAG—GAT—ATC—CTG—CTG—
GTC—CAG—TAC—CTA—CTC—GTC—TGC—TAC—CAC—GTC—CTA—TAG—GAC—GAC—

380                                                         390
Met   Lys   Gln   Asn   Asn   Phe   Asn   Ala   Val   Arg   Cys   Ser   His   Tyr
ATG—AAG—CAG—AAC—AAC—TTT—AAC—GCC—GTG—CGC—TGT—TCG—CAT—TAT—
TAC—TTC—GTC—TTG—TTG—AAA—TTG—CGG—CAC—GCG—ACA—AGC—GTA—ATA—

400
Pro   Asn   His   Pro   Leu   Trp   Tyr   Thr   Leu   Cys   Asp   Arg   Tyr   Gly
CCG—AAC—CAT—CCG—CTG—TGG—TAC—ACG—CTG—TGC—GAC—CGC—TAC—GGC—
GGC—TTG—GTA—GGC—GAC—ACC—ATG—TGC—GAC—ACG—CTG—GCG—ATG—CCG—

410                                                   420
Leu   Tyr   Val   Val   Asp   Glu   Ala   Asn   Ile   Glu   Thr   His   Gly   Met
CTG—TAT—GTG—GTG—GAT—GAA—GCC—AAT—ATT—GAA—ACC—CAC—GGC—ATG—
GAC—ATA—CAC—CAC—CTA—CTT—CGG—TTA—TAA—CTT—TGG—GTG—CCG—TAC—

430
Val   Pro   Met   Asn   Arg   Leu   Thr   Asp   Asp   Pro   Arg   Trp   Leu   Pro
GTG—CCA—ATG—AAT—CGT—CTG—ACC—GAT—GAT—CCG—CGC—TGG—CTA—CCG—
CAC—GGT—TAC—TTA—GCA—GAC—TGG—CTA—CTA—GGC—GCG—ACC—GAT—GGC—

440
Ala   Met   Ser   Glu   Arg   Val   Thr   Arg   Met   Val   Gln   Arg   Asp   Arg
GCG—ATG—AGC—GAA—CGC—GTA—ACG—CGA—ATG—GTG—CAG—CGC—GAT—CGT—
CGC—TAC—TCG—CTT—GCG—CAT—TGC—GCT—TAC—CAC—GTC—GCG—CTA—GCA—

450                                                   460
Asn   His   Pro   Ser   Val   Ile   Ile   Trp   Ser   Leu   Gly   Asn   Glu   Ser
AAT—CAC—CCG—AGT—GTG—ATC—ATC—TGG—TCG—CTG—GGG—AAT—GAA—TCA—
TTA—GTG—GGC—TCA—CAC—TAG—TAG—ACC—AGC—GAC—CCC—TTA—CTT—AGT—

470
Gly   His   Gly   Ala   Asn   His   Asp   Ala   Leu   Tyr   Arg   Trp   Ile   Lys
GGC—CAC—GGC—GCT—AAT—CAC—GAC—GCG—CTG—TAT—CGC—TGG—ATC—AAA—
CCG—GTG—CCG—CGA—TTA—GTG—CTG—CGC—GAC—ATA—GCG—ACC—TAG—TTT—

480                                                   490
Ser   Val   Asp   Pro   Ser   Arg   Pro   Val   Gln   Tyr   Glu   Gly   Gly   Gly
TCT—GTC—GAT—CCT—TCC—CGC—CCG—GTG—CAG—TAT—GAA—GGC—GGC—GGA—
AGA—CAG—CTA—GGA—AGG—GCG—GGC—CAC—GTC—ATA—CTT—CCG—CCG—CCT—

500
Ala   Asp   Thr   Thr   Ala   Thr   Asp   Ile   Ile   Cys   Pro   Met   Tyr   Ala
GCC—GAC—ACC—ACG—GCC—ACC—GAT—ATT—ATT—TGC—CCG—ATG—TAC—GCG—
CGG—CTG—TGG—TGC—CGG—TGG—CTA—TAA—TAA—ACG—GGC—TAC—ATG—CGC—
```

```
                                    510
Arg  Val  Asp  Glu  Asp  Gln  Pro  Phe  Pro  Ala  Val  Pro  Lys  Trp
CGC—GTG—GAT—GAA—GAC—CAG—CCC—TTC—CCG—GCT—GTG—CCG—AAA—TGG—
GCG—CAC—CTA—CTT—CTG—GTC—GGG—AAG—GGC—CGA—CAC—GGC—TTT—ACC—

520                                                  530
Ser  Ile  Lys  Lys  Trp  Leu  Ser  Leu  Pro  Gly  Glu  Thr  Arg  Pro
TCC—ATC—AAA—AAA—TGG—CTT—TCG—CTA—CCT—GGA—GAG—ACG—CGC—CCG—
AGG—TAG—TTT—TTT—ACC—GAA—AGC—GAT—GGA—CCT—CTC—TGC—GCG—GGC—

540
Leu  Ile  Leu  Cys  Glu  Tyr  Ala  His  Ala  Met  Gly  Asn  Ser  Leu
CTG—ATC—CTT—TGC—GAA—TAC—GCC—CAC—GCG—ATG—GGT—AAC—AGT—CTT—
GAC—TAG—GAA—ACG—CTT—ATG—CGG—GTG—CGC—TAC—CCA—TTG—TCA—GAA—

550                                       560
Gly—Gly—Phe—Ala—Lys—Tyr—Trp—Gln—Ala—Phe—Arg—Gln—Tyr—Pro—
GGC—GGT—TTC—GCT—AAA—TAC—TGG—CAG—GCG—TTT—CGT—CAG—TAT—CCC—
CCG—CCA—AAG—CGA—TTT—ATG—ACC—GTC—CGC—AAA—GCA—GTC—ATA—GGG—

570
Arg  Leu  Gln  Gly  Gly  Phe  Val  Trp  Asp  Trp  Val  Asp  Gln  Ser
CGT—TTA—CAG—GGC—GGC—TTC—GTC—TGG—GAC—TGG—GTG—GAT—CAG—TCG—
GCA—AAT—GTC—CCG—CCG—AAG—CAG—ACC—CTG—ACC—CAC—CTA—GTC—AGC—

580
Leu  Ile  Lys  Tyr  Asp  Glu  Asn  Gly  Asn  Pro  Trp  Ser  Ala  Tyr
CTG—ATT—AAA—TAT—GAT—GAA—AAC—GGC—AAC—CCG—TGG—TCG—GCT—TAC—
GAC—TAA—TTT—ATA—CTA—CTT—TTG—CCG—TTG—GGC—ACC—AGC—CGA—ATG—

590                                                  600
Gly  Gly  Asp  Phe  Gly  Asp  Thr  Pro  Asn  Asp  Arg  Gln  Phe  Cys
GGC—GGT—GAT—TTT—GGC—GAT—ACG—CCG—AAC—GAT—CGC—CAG—TTC—TGT—
CCG—CCA—CTA—AAA—CCG—CTA—TGC—GGC—TTG—CTA—GCG—GTC—AAG—ACA—

610
Met  Asn  Gly  Leu  Val  Phe  Ala  Asp  Arg  Thr  Pro  His  Pro  Ala
ATG—AAC—GGT—CTG—GTC—TTT—GCC—GAC—CGC—ACG—CCG—CAT—CCA—GCG—
TAC—TTG—CCA—GAC—CAG—AAA—CGG—CTG—GCG—TGC—GGC—GTA—GGT—CGC—

620                                            630
Leu  Thr  Glu  Ala  Lys  His  Gln  Gln  Gln  Phe  Phe  Gln  Phe  Arg
CTG—ACG—GAA—GCA—AAA—CAC—CAG—CAG—CAG—TTT—TTC—CAG—TTC—CGT—
GAC—TGC—CTT—CGT—TTT—GTG—GTC—GTC—GTC—AAA—AAG—GTC—AAG—GCA—

640
Leu  Ser  Gly  Gln  Thr  Ile  Glu  Val  Thr  Ser  Glu  Tyr  Leu  Phe
TTA—TCC—GGG—CAA—ACC—ATC—GAA—GTG—ACC—AGC—GAA—TAC—CTG—TTC—
AAT—AGG—CCC—GTT—TGG—TAG—CTT—CAC—TGG—TCG—CTT—ATG—GAC—AAG—

650
Arg  His  Ser  Asp  Asn  Glu  Leu  Leu  His  Trp  Met  Val  Ala  Leu
CGT—CAT—AGC—GAT—AAC—GAG—CTC—CTG—CAC—TGG—ATG—GTG—GCG—CTG—
GCA—GTA—TCG—CTA—TTG—CTC—GAG—GAC—GTG—ACC—TAC—CAC—CGC—GAC—
```

```
            660                                                    670
Asp   Gly   Lys   Pro   Leu   Ala   Ser   Gly   Glu   Val   Pro   Leu   Asp   Val
GAT—GGT—AAG—CCG—CTG—GCA—AGC—GGT—GAA—GTG—CCT— CTG—GAT—GTC—
CTA—CCA—TTC— GGC—GAC—CGT—TCG—CCA—CTT— CAC—GGA—GAC—CTA—CAG—

680
Ala   Pro   Gln   Gly   Lys   Gln   Leu   Ile   Glu   Leu   Pro   Glu   Leu   Pro
GCT—CCA—CAA—GGT—AAA—CAG—TTG—ATT—GAA—CTG—CCT— GAA—CTA—CCG—
CGA—GGT—GTT—CCA—TTT— GTC—AAC—TAA—CTT— GAC—GGA—CTT— GAT—GGC—

690                                                    700
Gln   Pro   Glu   Ser   Ala   Gly   Gln   Leu   Trp   Leu   Thr   Val   Arg   Val
CAG—CCG—GAG—AGC—GCC—GGG—CAA—CTC— TGG—CTC— ACA—GTA—CGC—GTA—
GTC—GGC—CTC— TCG—CGG—CCC— GTT—GAG—ACC—GAG—TGT—CAT—GCG—CAT—

710
Val   Gln   Pro   Asn   Ala   Thr   Ala   Trp   Ser   Glu   Ala   Gly   His   Ile
GTG—CAA—CCG—AAC—GCG—ACC—GCA—TGG—TCA—GAA—GCC—GGG—CAC—ATC—
CAG—GTT—GGC—TTG—CGC—TGG—CGT—ACC—AGT—CTT— CGG—CCC— GTG—TAG—

720
Ser   Ala   Trp   Gln   Gln   Trp   Arg   Leu   Ala   Glu   Asn   Leu   Ser   Val
AGC—GCC—TGG—CAG—CAG—TGG—CGT—CTG—GCG—GAA—AAC—CTC— AGT—GTG—
TCG—CGG—ACC—GTC—GTC—ACC—GCA—GAC—CGC—CTT— TTG—GAG—TCA—CAC—

730                                            740
Thr   Leu   Pro   Ala   Ala   Ser   His   Ala   Ile   Pro   His   Leu   Thr   Thr
ACG—CTC— CCC— GCC   GCG—TCC— CAC—GCC—ATC—CCG—CAT—CTG—ACC—ACC—
TGC—GAG—GGG—CGG—CGC—AGG—GTG—CGG—TAG—GGC—GTA—GAC—TGG—TGG—

750
Ser   Glu   Met   Asp   Phe   Cys   Ile   Glu   Leu   Gly   Asn   Lys   Arg   Trp
AGC—GAA—ATG—GAT—TTT— TGC—ATC— GAG—CTG—GGT—AAT—AAG—CGT—TGG—
TCG—CTT— TAC—CTA—AAA—ACG—TAG —CTC— GAC—CCA—TTA—TTC— GCA—ACC—

760                                                    770
Gln   Phe   Asn   Arg   Gln   Ser   Gly   Phe   Leu   Ser   Gln   Met   Trp   Ile
CAA—TTT— AAC—CGC—CAG—TCA—GGC—TTT— CTT— TCA—CAG—ATG—TGG—ATT—
GTT—AAA—TTG—GCG—GTC—AGT—CCG—AAA—GAA—AGT—GTC—TAC—ACC—TAA—

780
Gly   Asp   Lys   Lys   Gln   Leu   Leu   Thr   Pro   Leu   Arg   Asp   Gln   Phe
GGC—GAT—AAA—AAA—CAA—CTG—CTG—ACG—CCG—CTG—CGC—GAT—CAG—TTC—
CCG—CTA—TTT— TTT— GTT—GAC—GAC—TGC—GGC—GAC—GCG—CTA—GTC—AAG—

790
Thr   Arg   Ala   Pro   Leu   Asp   Asn   Asp   Ile   Gly   Val   Ser   Glu   Ala
ACC—CGT—GCA—CCG—CTG—GAT—AAC—GAC—ATT—GGC—GTA—AGT—GAA—GCG—
TGG—GCA—CGT—GGC—GAC—CTA—TTG—CTG—TAA—CCG—CAT—TCA—CTT— CGC—

800                                            810
Thr   Arg   Ile   Asp   Pro   Asn   Ala   Trp   Val   Glu   Arg   Trp   Lys   Ala
ACC—CGC—ATT—GAC—CCT— AAC—GCC—TGG—GTC—GAA—CGC—TGG—AAG—GCG—
TGG—GCG—TAA—CTG—GGA—TTG—CGG—ACC—CAG—CTT— GCG—ACC—TTC— CGC—

820
Ala   Gly   His   Tyr   Gln   Ala   Glu   Ala   Ala   Leu   Leu   Gln   Cys   Thr
GCG—GGC—CAT—TAC—CAG—GCC—GAA—GCA—GCG—TTG—TTG—CAG—TGC—ACG—
CGC—CCG—GTA—ATG—GTC—CGG—CTT— CGT—CGC—AAC—AAC—GTC—ACG—TGC—
```

```
                                              830                                                            840
Ala   Asp   Thr   Leu   Ala   Asp   Ala   Val   Leu   Ile   Thr   Thr   Ala   His
GCA—GAT—ACA—CTT—GCT—GAT—GCG—GTG—CTG—ATT—ACG—ACC—GCT—CAC—
CGT—CTA—TGT—GAA—CGA—CTA—CGC—CAC—GAC—TAA—TGC—TGG—CGA—GTG—

850
Ala   Trp   Gln   His   Gln   Gly   Lys   Thr   Leu   Phe   Ile   Ser   Arg   Lys
GCG—TGG—CAG—CAT—CAG—GGG—AAA—ACC—TTA—TTT—ATC—AGC—CGG—AAA—
CGC—ACC—GTC—GTA—GTC—CCC—TTT—TGG—AAT—AAA—TAG—TCG—GCC—TTT—

860
Thr   Tyr   Arg   Ile   Asp   Gly   Ser   Gly   Gln   Met   Ala   Ile   Thr   Val
ACC—TAC—CGG—ATT—GAT—GGT—AGT—GGT—CAA—ATG—GCG—ATT—ACC—GTT—
TGG—ATG—GCC—TAA—CTA—CCA—TCA—CCA—GTT—TAC—CGC—TAA—TGG—CAA—

870                                                      880
Asp   Val   Glu   Val   Ala   Ser   Asp   Thr   Pro   His   Pro   Ala   Arg   Ile
GAT—GTT—GAA—GTG—GCG—AGC—GAT—ACA—CCG—CAT—CCG—GCG—CGG—ATT—
CTA—CAA—CTT—CAC—CGC—TCG—CTA—TGT—GGC—GTA—GGC—CGC—GCC—TAA—

890
Gly   Leu   Asn   Cys   Gln   Leu   Ala   Gln   Val   Ala   Glu   Arg   Val   Asn
GGC—CTG—AAC—TGC—CAG—CTG—GCG—CAG—GTA—GCA—GAG—CGG—GTA—AAC—
CCG—GAC—TTG—ACG—GTC—GAC—CGC—GTC—CAT—CGT—CTC—GCC—CAT—TTG—

900                                                      910
Trp   Leu   Gly   Leu   Gly   Pro   Gln   Glu   Asn   Tyr   Pro   Asp   Arg   Leu
TGG—CTC—GGA—TTA—GGG—CCG—CAA—GAA—AAC—TAT—CCC—GAC—CGC—CTT—
ACC—GAG—CCT—AAT—CCC—GGC—GTT—CTT—TTG—ATA—GGG—CTG—GCG—GAA—

920
Thr   Ala   Ala   Cys   Phe   Asp   Arg   Trp   Asp   Leu   Pro   Leu   Ser   Asp
ACT—GCC—GCC—TGT—TTT—GAC—CGC—TGG—GAT—CTG—CCA—TTG—TCA—GAC—
TGA—CGG—CGG—ACA—AAA—CTG—GCG—ACC—CTA—GAC—GGT—AAC—AGT—CTG—

930
Met   Tyr   Thr   Pro   Tyr   Val   Phe   Pro   Ser   Glu   Asn   Gly   Leu   Arg
ATG—TAT—ACC—CCG—TAC—GTC—TTC—CCG—AGC—GAA—AAC—GGT—CTG—CGC—
TAC—ATA—TGG—GGC—ATG—CAG—AAG—GGC—TCG—CTT—TTG—CCA—GAC—GCG—

940                                                      950
Cys   Gly   Thr   Arg   Glu   Leu   Asn   Tyr   Gly   Pro   His   Gln   Trp   Arg
TGC—GGG—ACG—CGC—GAA—TTG—AAT—TAT—GGC—CCA—CAC—CAG—TGG—CGC—
ACG—CCC—TGC—GCG—CTT—AAC—TTA—ATA—CCG—GGT—GTG—GTC—ACC—GCG—

960
Gly   Asp   Phe   Gln   Phe   Asn   Ile   Ser   Arg   Tyr   Ser   Gln   Gln   Gln
GGC—GAC—TTC—CAG—TTC—AAC—ATC—AGC—CGC—TAC—AGT—CAA—CAG—CAA—
CCG—CTG—AAG—GTC—AAG—TTG—TAG—TCG—GCG—ATG—TCA—GTT—GTC—GTT—

970                                                      980
Leu   Met   Glu   Thr   Ser   His   Arg   His   Leu   Leu   His   Ala   Glu   Glu
CTG—ATG—GAA—ACC—AGC—CAT—CGC—CAT—CTG—CTG—CAC   GCG—GAA—GAA—
GAC—TAC—CTT—TGG—TCG—GTA—GCG—GTA—GAC—GAC—GTG—CGC—CTT—CTT—
```

-continued

```
                                           990
Gly  Thr  Trp  Leu  Asn  Ile  Asp  Gly  Phe  His  Met  Gly  Ile  Gly
GGC—ACA—TGG—CTG—AAT—ATC—GAC—GGT—TTC— CAT—ATG—GGG—ATT—GGT—
CCG—TGT—ACC—GAC—TTA—TAG—CTG—CCA—AAG—GTA—TAC—CCC— TAA—CCA—

1000
Gly  Asp  Asp  Ser  Trp  Ser  Pro  Ser  Val  Ser  Ala  Glu  Phe  Met
GGC—GAC—GAC—TCC— TGG—AGC—CCG—TCA—GTA—TCG—GCG—GAA—TTC— ATG—
CCG—CTG—CTG—AGG—ACC—TCG—GGC—AGT—CAT—AGC—CGC—CTT— AAG—GAC—

1010                                    1020
Gly  Pro  Glu  Thr  Leu  Cys  Gly  Ala  Glu  Leu  Val  Asp  Ala  Leu
GGT—CCT— GAA—ACT—CTG—TGC—GGC—GCT—GAA—CTG—GTT—GAC—GCT—CTG—
CCA—GGA—CTT— TGA—GAC—ACG—CCG—CGA—CTT— GAC—CAA—CTG—CGA—GAC—

1030
Gln  Phe  Val  Cys  Gly  Asp  Arg  Gly  Phe  Tyr  Phe  Asn  Lys  Pro
CAA—TTT— GTA—TGT—GGT—GAT—CGT—GGT—TTC— TAC—TTC— AAC—AAA—CCG—
GTT—AAA—CAT—ACA—CCA—CTA—GCA—CCA—AAG—ATG—AAG—TTG—TTT— GGC—

1040                                         1050
Thr  Gly  Tyr  Gly  Ser  Ser  Ser  Arg  Arg  Ala  Pro  Gln  Thr  Gly
ACC—GGC—TAT—GGC—TCC— AGC—TCT— CGT—CGC—GCA—CCG—CAG—ACT—GGT—
TGG—CCG—ATA—CCG—AGG—TCG—AGA—GCA—GCG—CGT—GGC—GTC—TGA—CCA—

1060
Ile  Val  Asp  Glu  Cys  Cys  Phe  Arg  Ser  Cys  Asp  Leu  Arg  Arg
ATC—GTA—GAC—GAA—TGC—TGT—TTT— CGT—TCT— TGC—GAT—CTC— CGC—CGT—
TAG—CAT—CTG—CTT— ACG—ACA—AAA—GCA—AGA—ACG—CTA—GAG—GCG—GCA—

1070
Leu  Glu  Val  Tyr  Cys  Ala  Pro  Leu  Lys  Pro  Ala  Lys  Ser  Ala
CTG—GAA—GTT—TAC—TGT—GCT—CCA—CTG—AAG—CCA—GCA—AAA—TCC  GCG—3'
GAC—CTT— CAA—ATG—ACA—CGA—GGT—GAC—TTC— GGT—CGT—TTT— AGG—CGC—5'
```

[7]

EXPRESSION OF THE $^{59}$Val-IGF-I GENE IN A HOST ORGANISM

For expression of the $^{59}$Val-IGF-I gene, thus obtained plasmid having a promoter gene and $^{59}$Val-IGF-I gene is transformed into a host organism, and then the host organism having the plasmid is the cultured in nutrient medium containing sources of assimilable carbon and nitrogen under aerobic conditions (e.g. shaking culture, submerged culture, etc.).

The preferred sources of carbon in the nutrient medium are carbohydrates such as glucose, fructose, sucrose, glycerin, starch and the like. Other sources which may be included are xylose, galactose, maltose, dextrin, lactose and the like.

The preferred sources of nitrogen are yeast extract, peptone, gluten meal, cottonseed flour, soybean meal, corn steep liquor, dried yeast, wheat germ, etc., as well as inorganic and organic nitrogen compounds such as ammonium nitrate, ammonium sulfate, ammonium phosphate, etc.), urea, amino acid and the like.

The carbon and nitrogen sources, though advantageously employed in combination, need not be used in their pure form, because less pure materials which contain traces of growth factors and considerable quantities of mineral nutrients, are also suitable for use. When desired, there may be added to the medium mineral salts such as calcium carbonate, sodium or potassium phosphate, sodium or potassium chloride, magnesium salts, copper salts and the like.

Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the medium. Agitation may be effected by passing sterile air through the fermentation mixture.

The fermentation is usually conducted at a temperature between about 20° C. and 42° C., preferably 35°–38° C., for a period of several hours to 50 hours.

Thus produced $^{59}$Val-IGF-I or fused $^{59}$Val-IGF-I can be recovered from the cultured medium by conventional means which are commonly used for the recovery of other known biologically active substances. In general, $^{59}$Val-IGF-I or fused $^{59}$Val-IGF-I produced are found in the cells of host organisms, and accordingly $^{59}$Val-IGF-I or fused $^{59}$Val-IGF-I can be separated from the cells, which is obtained by filtering or centrifuging the cultured broth, by a conventional method such as concentration under reduced pressure, lysis such as sonication, HPLC, lyophilization, pH adjustment, treatment with resin (e.g. anion or cation exchange resin, non-ionic adsorption resin), treatment with a conventional absorbent (e.g. activated carbon, silicic acid, silica gel, cellulose, almina), gel filtration, crystallization, and the like.

(1) Expression of the $^{59}$Val-IGF-I gene in *E. coli* using plasmid pSdV2trp

An overnight culture of *E. coli* HB101 containing pSdV2trp in L broth was diluted in M9 medium lacking tryptophan, and the cells were incubated at 37° C. for 3 hours under the condition of β-indoleacrylic acid induction. Detection of $^{59}$Val-IGF-I production was carried out using a radioimmunossay (hereinafter referred to RIA) with the antibody of $^{59}$Val-IGF-I fragment (26-46) according to N. Yanaihara's method [N. Yanahaihara et al, Peptide Hormones in Pancreas 3, 28(1983)].

(2) Expression of the $^{59}$Val-IGF-I gene in *E. coli* using plasmid pSdV2-322trp An overnight culture of *E. coli* HB101 containing plasmid pSdV2-322 trp in L broth was diluted in M9 medium lacking tryptophan, and the cells were incubated at 37° C. for 3 hours under the condition of β-indoleacrylic acid induction. Detection of $^{59}$Val-IGF-I production was carried out using RIA with the antibody of $^{59}$Val-IGF-I fragment (26-46) according to N. Yanaihara's method.

[8]

EXPRESSION OF A GENE CODING FOR FUSED $^{59}$Val-IGF-I IN A HOST ORGANISM (1) Expression of a gene coding for $^{59}$Val-IGF-I gene fused with protein peptide LH in a host organism:

For the expression of a gene coding for $^{59}$Val-IGF-I fused with protein peptide LH, thus obtained plasmid having a promoter gene and a gene coding for $^{59}$Val-IGF-I fused with protein peptide LH is transformed into a host organism, and then the host organism having the plasmid is cultured in a suitable medium. $^{59}$Val-IGF-I fused with protein peptide LH is isolated from the resulting culture broth.

(i) Expression of a gene coding for $^{59}$Val-IGF-I fused with protein peptide LH in *E. coli* using plasmid pLHSdVtrp:

An overnight culture of *E. coli* HB101 containing pLHSdVtrp, pLHSdVtrpS or pLHSdVtrpL in L broth was diluted in M9 medium lacking tryptophan, and the cells were incubated at 37° C. for 3 hours under the condition of β-indoleacrylic acid induction. Detection of the fused $^{59}$Val-IGF-I production was carried out using a radioimmunoassay (hereinafter referred to as RIA) with the antibody of $^{59}$Val-IGF-I fragment (26-46) according to N. Yanihara's method [N. Yanaihara et al, Peptide Hormones in Pancreas 3, 28(1983)].

(ii) Isolation of $^{59}$Val-IGF-I fused with protein peptide LH:

The culture fluid was centrifuged to give a wet cell paste, and the cells were lysed by sonication. The pellet was collected by centrifugation and then dissolved in 8M urea solution containing 0.1 M dithiothreitol (hereinafter referred to as DTT). After centrifugation the solution was purified by S 300 column chromatography. Active fractions detected by RIA were collected and dialysed to give protein which contains a desired component. The fused $^{59}$Val-IGF-I was detected a normal position (15500) on polyacrylamide gel electrophoresis.

Thus obtained $^{59}$Val-IGF-I fused with protein peptide LH is as follows:

```
         1                                                    10
         Cys—Tyr—Cys—Gln—Asp—Pro—Tyr—Val—Lys—Glu—Ala—Glu—Asn—Leu—

20
         Lys—Lys—Tyr—Phe—Asn—Ala—Gly—His—Ser—Asp—Val—Ala—Asp—Asn—

30                                  40
         Gly—Thr—Leu—Phe—Leu—Gly—Ile—Leu—Lys—Asn—Trp—Lys—Glu—Glu—

50
         Ser—Asp—Arg—Lys—Ile—Met—Gln—Ser—Gln—Ile—Val—Ser—Phe—Tyr—

60                                        70
         Phe—Lys—Leu—Glu—Val—Lys—His—Glu—Phe—Met—Gly—Pro—Glu—Thr—

80
         Leu—Cys—Gly—Ala—Glu—Leu—Val—Asp—Ala—Leu—Gln—Phe—Val—Cys—

90
         Gly—Asp—Arg—Gly—Phe—Tyr—Phe—Asn—Lys—Pro—Thr—Gly—Tyr—Gly—

100                                        110
         Ser—Ser—Ser—Arg—Arg—Ala—Pro—Gln—Thr—Gly—Ile—Val—Asp—Glu—

120
         Cys—Cys—Phe—Arg—Ser—Cys—Asp—Leu—Arg—Arg—Leu—Glu—Val—Tyr—

130
         Cys—Ala—Pro—Leu—Lys—Pro—Ala—Lys—Ser—Ala
```

(2) Expression of a gene coding for $^{59}$Val-IGF-I fused with β-galctosidase in a host organism:

$^{59}$Val-IGF-I fused with β-galactosidase was obtained using a host organism containing pSdV2-lac or a host organism containing pSdV2-NT49 and pNT204 according to a similar manner to that of $^{59}$Val-IGF-I fused with protein peptide LH.

Thus obtained fused $^{59}$Val-IGF-I is as follows:

```
         1                                              10
         Thr—Met—Ile—Thr—Asp—Ser—Leu—Ala—Val—Val—Leu—Gln—Arg—Arg—
```

-continued

20
Asp—Trp—Glu—Asn—Pro—Gly—Val—Thr—Gln—Leu—Asn—Arg—Leu—Ala—

30              40
Ala—His—Pro—Pro—Phe—Ala—Ser—Trp—Arg—Asn—Ser—Glu—Glu—Ala—

50
Arg—Thr—Asp—Arg—Pro—Ser—Gln—Gln—Leu—Arg—Ser—Leu—Asn—Gly—

60                        70
Glu—Trp—Arg—Phe—Ala—Trp—Phe—Pro—Ala—Pro—Glu—Ala—Val—Pro—

80
Glu—Ser—Trp—Leu—Glu—Cys—Asp—Leu—Pro—Glu—Ala—Asp—Thr—Val—

90
Val—Val—Pro—Ser—Asn—Trp—Gln—Met—His—Gly—Tyr—Asp—Ala—Pro—

100              110
Ile—Tyr—Thr—Asn—Val—Thr—Tyr—Pro—Ile—Thr—Val—Asn—Pro—Pro—

120
Phe—Val—Pro—Thr—Glu—Asn—Pro—Thr—Gly—Cys—Tyr—Ser—Leu—Thr—

130              140
Phe—Asn—Val—Asp—Glu—Ser—Trp—Leu—Gln—Glu—Gly—Gln—Thr—Arg—

150
Ile—Ile—Phe—Asp—Gly—Val—Asn—Ser—Ala—Phe—His—Leu—Trp—Cys—

160
Asn—Gly—Arg—Trp—Val—Gly—Tyr—Gly—Gln—Asp—Ser—Arg—Leu—Pro—

170              180
Ser—Glu—Phe—Asp—Leu—Ser—Ala—Phe—Leu—Arg—Ala—Gly—Glu—Asn—

190
Arg—Leu—Ala—Val—Met—Val—Leu—Arg—Trp—Ser—Asp—Gly—Ser—Try—

200              210
Leu—Glu—Asp—Gln—Asp—Met—Trp—Arg—Met—Ser—Gly—Ile—Phe—Arg—

220
Asp—Val—Ser—Leu—Leu—His—Lys—Pro—Thr—Thr—Gln—Ile—Ser—Asp—

230
Phe—His—Val—Ala—Thr—Arg—Phe—Asn—Asp—Asp—Phe—Ser—Arg—Ala—

240              250
Val—Leu—Glu—Ala—Glu—Val—Gln—Met—Cys—Gly—Glu—Leu—Arg—Asp—

260
Tyr—Leu—Arg—Val—Thr—Val—Ser—Leu—Trp—Gln—Gly—Glu—Thr—Gln—

270              280
Val—Ala—Ser—Gly—Thr—Ala—Pro—Phe—Gly—Gly—Glu—Ile—Ile—Asp—

290
Glu—Arg—Gly—Gly—Tyr—Ala—Asp—Arg—Val—Thr—Leu—Arg—Leu—Asn—

300
Val—Glu—Asn—Pro—Lys—Leu—Trp—Ser—Ala—Glu—Ile—Pro—Asn—Leu—

310              320
Tyr—Arg—Ala—Val—Val—Glu—Leu—His—Thr—Ala—Asp—Gly—Thr—Leu—

330
Ile—Glu—Ala—Glu—Ala—Cys—Asp—Val—Gly—Phe—Arg—Glu—Val—Arg—

340              350
Ile—Glu—Asn—Gly—Leu—Leu—Leu—Leu—Asn—Gly—Lys—Pro—Leu—Leu—

Ile—Arg—Gly—Val—Asn—Arg—His—Glu—His—His—Pro—Leu—His—Gly—

370
Gln—Val—Met—Asp—Glu—Gln—Thr—Met—Val—Gln—Asp—Ile—Leu—Leu—

380              390
Met—Lys—Gln—Asn—Asn—Phe—Asn—Ala—Val—Arg—Cys—Ser—His—Tyr—

```
                              400
Pro—Asn—His—Pro—Leu—Trp—Tyr—Thr—Leu—Cys—Asp—Arg—Tyr—Gly—
         410                                  420
Leu—Tyr—Val—Val—Asp—Glu—Ala—Asn—Ile—Glu—Thr—His—Gly—Met—
                              430
Val—Pro—Met—Asn—Arg—Leu—Thr—Asp—Asp—Pro—Arg—Trp—Leu—Pro—
                    440
Ala—Met—Ser—Glu—Arg—Val—Thr—Arg—Met—Val—Gln—Arg—Asp—Arg—
    450                                      460
Asn—His—Pro—Ser—Val—Ile—Ile—Trp—Ser—Leu—Gly—Asn—Glu—Ser—
                         470
Gly—His—Gly—Ala—Asn—His—Asp—Ala—Leu—Tyr—Arg—Trp—Ile—Lys—
               480                              490
Ser—Val—Asp—Pro—Ser—Arg—Pro—Val—Gln—Tyr—Glu—Gly—Gly—Gly—
                              500
Ala—Asp—Thr—Thr—Ala—Thr—Asp—Ile—Ile—Cys—Pro—Met—Tyr—Ala—
                         510
Arg—Val—Asp—Glu—Asp—Gln—Pro—Phe—Pro—Ala—Val—Pro—Lys—Trp—
    520                              530
Ser—Ile—Lys—Lys—Trp—Leu—Ser—Leu—Pro—Gly—Glu—Thr—Arg—Pro—
                         540
Leu—Ile—Leu—Cys—Glu—Tyr—Ala—His—Ala—Met—Gly—Asn—Ser—Leu—
                    550                              560
Gly—Gly—Phe—Ala—Lys—Tyr—Trp—Gln—Ala—Phe—Arg—Gln—Tyr—Pro—
                              570
Arg—Leu—Gln—Gly—Gly—Phe—Val—Trp—Asp—Trp—Val—Asp—Gln—Ser—
                         580
Leu—Ile—Lys—Tyr—Asp—Glu—Asn—Gly—Asn—Pro—Trp—Ser—Ala—Tyr—
    590                                      600
Gly—Gly—Asp—Phe—Gly—Asp—Thr—Pro—Asn—Asp—Arg—Gln—Phe—Cys—
                              610
Met—Asn—Glu—Leu—Val—Phe—Ala—Asp—Arg—Thr—Pro—His—Pro—Ala—
               620                              630
Leu—Thr—Glu—Ala—Lys—His—Gln—Gln—Gln—Phe—Phe—Gln—Phe—Arg—
                              640
Leu—Ser—Gly—Gln—Thr—Ile—Glu—Val—Thr—Ser—Glu—Tyr—Leu—Phe—
                    650
Arg—His—Ser—Asp—Asn—Glu—Leu—Leu—His—Trp—Met—Val—Ala—Leu—
    660                              670
Asp—Gly—Lys—Pro—Leu—Ala—Ser—Gly—Glu—Val—Pro—Leu—Asp—Val—
                         680
Ala—Pro—Gln—Gly—Lys—Gln—Leu—Ile—Glu—Leu—Pro—Glu—Leu—Pro—
         690                                  700
Gln—Pro—Glu—Ser—Ala—Gly—Gln—Leu—Trp—Leu—Thr—Val—Arg—Val—
                              710
Val—Gln—Pro—Asn—Ala—Thr—Ala—Trp—Ser—Glu—Ala—Gly—His—Ile—
                    720
Ser—Ala—Trp—Gln—Gln—Trp—Arg—Leu—Ala—Glu—Asn—Leu—Ser—Val—
    730                              740
Thr—Leu—Pro—Ala—Ala—Ser—His—Ala—Ile—Pro—His—Leu—Thr—Thr—
                         750
Ser—Glu—Met—Asp—Phe—Cys—Ile—Glu—Leu—Gly—Asn—Lys—Arg—Trp—
         760                                  770
Gln—Phe—Asn—Arg—Gln—Ser—Gly—Phe—Leu—Ser—Gln—Met—Trp—Ile—
```

-continued

780
Gly—Asp—Lys—Lys—Gln—Leu—Leu—Thr—Pro—Leu—Arg—Asp—Gln—Phe—

790
Thr—Arg—Ala—Pro—Leu—Asp—Asn—Asp—Ile—Gly—Val—Ser—Glu—Ala—

800                                                810
Thr—Arg—Ile—Asp—Pro—Asn—Ala—Trp—Val—Glu—Arg—Trp—Lys—Ala—

820
Ala—Gly—His—Tyr—Gln—Ala—Glu—Ala—Ala—Leu—Leu—Gln—Cys—Thr—

830                                                840
Ala—Asp—Thr—Leu—Ala—Asp—Ala—Val—Leu—Ile—Thr—Thr—Ala—His—

850
Ala—Trp—Gln—His—Gln—Gly—Lys—Thr—Leu—Phe—Ile—Ser—Arg—Lys—

860
Thr—Tyr—Arg—Ile—Asp—Gly—Ser—Gly—Gln—Met—Ala—Ile—Thr—Val—

870                                                880
Asp—Val—Glu—Val—Ala—Ser—Asp—Thr—Pro—His—Pro—Ala—Arg—Ile—

890
Gly—Leu—Asn—Cys—Gln—Leu—Ala—Gln—Val—Ala—Glu—Arg—Val—Asn—

900                                                910
Trp—Leu—Gly—Leu—Gly—Pro—Gln—Glu—Asn—Tyr—Pro—Asp—Arg—Leu—

920
Thr—Ala—Ala—Cys—Phe—Asp—Arg—Trp—Asp—Leu—Pro—Leu—Ser—Asp—

930
Met—Tyr—Thr—Pro—Tyr—Val—Phe—Pro—Ser—Glu—Asn—Gly—Leu—Arg—

940                                                950
Cys—Gly—Thr—Arg—Glu—Leu—Asn—Tyr—Gly—Pro—His—Gln—Trp—Arg—

960
Gly—Asp—Phe—Gln—Phe—Asn—Ile—Ser—Arg—Tyr—Ser—Gln—Gln—Gln—

970                                                980
Leu—Met—Glu—Thr—Ser—His—Arg—His—Leu—Leu—His—Ala—Glu—Glu—

990
Gly—Thr—Trp—Leu—Asn—Ile—Asp—Gly—Phe—His—Met—Gly—Ile—Gly—

1000
Gly—Asp—Asp—Ser—Trp—Ser—Pro—Ser—Val—Ser—Ala—Glu—Phe—Met—

1010                                               1020
Gly—Pro—Glu—Thr—Leu—Cys—Gly—Ala—Glu—Leu—Val—Asp—Ala—Leu—

1030
Gln—Phe—Val—Cys—Gly—Asp—Arg—Gly—Phe—Tyr—Phe—Asn—Lys—Pro—

1040                                               1050
Thr—Gly—Tyr—Gly—Ser—Ser—Ser—Arg—Arg—Ala—Pro—Gln—Thr—Gly—

1060
Ile—Val—Asp—Glu—Cys—Cys—Phe—Arg—Ser—Cys—Asp—Leu—Arg—Arg—

1070
Leu—Glu—Val—Tyr—Cys—Ala—Pro—Leu—Lys—Pro—Ala—Lys—Ser—Ala

[9]

CONVERSION OF FUSED $^{59}$Val-IGF-I to $^{59}$Val-IGF-I and isolation of $^{59}$Val-IGF-I Thus obtained fused $^{59}$Val-IGF-I can be converted to $^{59}$Val-IGF-I by elimination reaction of the protective peptide.

This elimination reaction can be conducted in accordance with a conventional method used in the field of peptide chemistry. Suitable elimination reaction can be selected according to the type of fused $^{59}$Val-IGF-I.

Suitable agent used in this elimination reaction may include cyanogen bromide.

(1) Elimination of the protein peptide from $^{59}$Val-IGF-I fused with the protein peptide through methionine of the protein peptide:

$^{59}$Val-IGF-I fused with a protein peptide through methionine of the protein peptide can be converted to $^{59}$Val-IGF-I by elimination reaction with cyanogen bromide.

This reaction is usually carried out under mild conditions in a conventional solvent which does not adversely affect the reaction.

The reaction temperature is not critical and the reaction is usually carried out from cooling to warming.

The fused $^{59}$Val-IGF-I was treated with cyanogen bromide in 60% formic acid at 25° C. for 3 hours. After lyophilization the residue was dissolved in an 8 M urea solution containing 50 mM 2-mercaptoethanol and dialyzed to give a crude mixture of reduced $^{59}$Val-IGF-I. The mixture was purified by cationic ion exchange chromatography (CM52), and active fractions detected by RIA were collected and dialysed. The dialysed fraction was applied on high performance liquid chromatography to give a pure reduced $^{59}$Val-IGF-I. The reduced $^{59}$Val-IGF-I was converted to oxidized $^{59}$Val-IGF-I by a usual manner of refolding. The purified $^{59}$Val-IGF-I showed a single band on polyacrylamide gel electrophoresis (PAGE), and the $^{59}$Val-IGF-I was supperimposed with authentic $^{59}$Val-IGF-I (gift of Dr. Humbel) on HPLC. The amino acid sequence of $^{59}$Val-IGF-I was determined by the conbination of Edman's method and carboxypeptidase method. The $^{59}$Val-IGF-I showed biological activity in [$^3$H]-thymidine incorporation assay of mouse BALB/c 3T3 cells.

[10]

RADIOIMMUNOASSAY OF $^{59}$Val-IGF-I

RIA of $^{59}$Val-IGF-I was followed the method established by N. Yanaihara [N. Yanaihara et al: Peptide Hormones in Pancreas 3, 28(1983)]. With 0.1 ml of the above sample or standard sample (IGF-I fragment (26–46)) sample buffer [0.5% BSA in 0.01M PBS, 0.025M EDTA (pH 7.4) (0.4 ml)], rabbit antiserum (0.1 ml) of $^{59}$Val-IGF-I (26–46) and $^{125}$I-IGF-I (26–46) (0.1 ml) were mixed. The mixture was allowed to stand for 48 hours at 4° C., and then added with rabbit serum (0.1 ml), rabbit γ-globulin antiserum (0.1 ml) and 5% PEG6000 (0.9 ml). After standing for additional 2 hours at 4° C. the pellet was collected by centrifugation (3 krpm, 4° C., 30 minutes), and measured radio activity by γ-counter. The content of $^{59}$Val-IGF-I was calculated from this radio activity.

[11]

BIOLOGICAL ASSAY OF $^{59}$Val-IGF-I

Mouse BALB/c 3T3 embryofibroblasts (clone A31) were trypsinized and resuspended at a concentration of $10^5$ cells/ml in Dulbecco-Vogt Modified Eagle's medium containing 10% New Born Calf Serum and 25 MM N-(2-hydroxyethyl)piperazine-N'-2-ethanesulfonic acid (HEPES). Aliquots of 100 μl were plated into 0.3 cm$^2$ wells (96 well-microtiter plate, Costor). Three to four days after the cells reached confluence (5–7 days after intial plating) the spent mediumn was removed and the culture was washed three times and then 0.2 μCi/well [$^3$H]thymidine (0.67 Ci/mmole) plus test samples were added. After incubation of 24 hours, the medium was removed and cells were washed with PBS and trypsinized for determination of radioactivity. Cells were trapped in glass filters by use of semi automatic multiple cell harvester (LAVO MASH, LABO SCIENCE). Incorporated [$^3$H]thymidine was counted in 8 ml of Aquazol 2 (New England Nuclear) using a Packeard Tri-Carb Liquid Scintillation Counter.

The following examples are given for the purpose of illustrating the present invention.

EXAMPLE 1

Synthesis of HOApApApCpCpGpApCpCpGpGpCpTpApT-pGOH (G1)

(1) Synthesis of DMTrOTpoA$^{Bz}$poTpoG$^{iB}$po$^{Ace}$Upo-cellulose:

(i) Preparation of HOG$^{iB}$po$^{Ac}$Upo-cellulose:

To a suspension of DMTrOG$^{iB}$po$^{Ac}$Upo-cellulose (130.4 mg, 4.59 μmole*) (prepared by R. Crea's method$^{(1)}$) in MeOH/CHCl$_3$ (1:9 v/v, 5.0 ml). TCA/CHCl$_3$ (2:8 w/v, 5.0 ml) was added under ice cooling, and the mixture was stirred at 0° C. for 10 min. After being washed with CHCl$_3$ (2 ml) and MeOH (6.0 ml), successively, on the filter, the cellulose adduct (HOG$^{iB}$po$^{Ac}$Upo-cellulose) was dried, water being separated as the pyridine (2 ml) azeotrope.

*This value was calculated by monitoring the aborbance of a washing solution with CHCl$_3$ at 507 nm.
(1) R. Crea et al, Nucleic Acid Res. 8, 2331(1980).

(ii) Preparation of DMTrOTpoA$^{Bz}$poTpo$^-$:

DMTrOTpoA$^{Bz}$poTpo-CE (39.9 mg, 23.0 μmole) was treated with Et$_3$N-CH$_3$CN (1:1 v/v, 5 ml) at room temperature fo 1 hr. The phosphodiester trimer (DMTrOTpoA$^{Bz}$poTpo$^-$) so obtained was dried, water being separated as the pyridine azeotrope (0.5 ml, 2×1 ml).

(iii) Coupling:

The trimer (DMTrOTpoA$^{Bz}$poTpo$^-$) was mixed with the cellulose adduct (HOG$^{iB}$po$^{Ac}$Upo-cellulose) in a 10 ml round-bottom flask, The mixture was dried, water being separated as the pyridine azeotrope (2×1 ml) and finally resupended in anhydrous pyridine (1 ml). Mesitylen sulfonyl nitrotriazolide (MSNT) (68.0 mg, 230 μmole) was added to the suspension and the mixture was stirred at room temperature for 1 hr. And then pyridine was added to the reaction vessel and cellulose adduct was recovered boy centrifugation (3,000 rpm, 2 min).

(iv) Acetylation of unreacted 5'hydroxyl groups:

The cellulose adduct obtained as above was suspended in a solution of pyridine-acetic anhydride (10:1 v/v, 5.5 ml) and stirred at room temperature for 30 min. The cellulose-product (113.9 mg) was obtained by repeated centrifugation (3,000 rpm, 2 min) in pyridine (5 ml), washing with MeOH (15 ml) and drying in vacuo at room temperature for 30 minutes. The cellulose adduct (DMTrOTpoA$^{Bz}$poTpoG$^{iB}$po$^{Ac}$Upo-Cellulose) can use for the next coupling step.

(2) Synthesis of DMTrOG$^{iB}$poG$^{iB}$poC$^{Bz}$poTpoA$^{Bz}$poTpoG$^{iB}$po$^{Ac}$- Upo-cellulose:

DMTrOG$^{iB}$poG$^{iB}$poC$^{Bz}$poTpoA$^{Bz}$poTpoG$^{iB}$-po$^{Ac}$Upo-cellulose was synthesized from DMTrOTpoA$^{Bz}$poTpoG$^{iB}$po$^{Ac}$Upo-cellulose (113.9 mg) and DMTrOG$^{iB}$poG$^{iB}$poC$^{Bz}$po-CE (43.7 mg) according to similar conditions as above.

(3) Synthesis of DMTrOA$^{Bz}$poC$^{Bz}$poC$^{Bz}$poG$^{iB}$-poG$^{ib}$poC$^{Bz}$poTpo- A$^{Bz}$poTpoG$^{iB}$po$^{Ac}$Upo-Cellulose:

DNTrOA$^{Bz}$poC$^{Bz}$poC$^{Bz}$poG$^{iB}$poG$^{iB}$poC$^{Bz}$poT-poA$^{Bz}$poTpoG$^{iB}$-po$^{Ac}$Upo-cellulose (105.8 mg) was synthesized from DMTrOG$^{iB}$poG$^{iB}$poC$^{Bz}$poTpoA$^{Bz}$-poTpoG$^{iB}$po$^{Ac}$Upo-cellulose (109.5 mg) and DMTrOA$^{Bz}$poC$^{Bz}$poC$^{Bz}$po-CE (44.0 mg) according to similar conditions.

(4) Synthesis of DMTrOC$^{Bz}$poC$^{Bz}$poG$^{iB}$poA$^{Bz}$poC$^{B-}$zpoC$^{Bz}$po- G$^{iB}$po-G$^{iB}$poC$^{Bz}$poTpoA$^{Bz}$poTpoG$^{iB}$-po$^{Ac}$Upo-cellulose:

DMTrOC$^{Bz}$poC$^{Bz}$poG$^{iB}$poA$^{Bz}$poC$^{Bz}$poC$^{Bz}$poG$^{iB}$-poG$^{iB}$poC$^{Bz}$po-TpoA$^{Bz}$poTpoG$^{iB}$po$^{Ac}$Upo-cellulose (94.5 mg) was synthesized from DMTrOA$^{Bz}$poC$^{Bz}$poC$^{Bz}$poG$^{iB}$poG$^{iB}$poC$^{Bz}$poTpoA$^{Bz}$poTpoG$^{iB}$po-$^{Ac}$Upo-cellulose (105.8 mg) and DMTrOC$^{Bz}$poC$^{Bz}$poG$^{iB}$po-CE (43.5 mg) according to similar conditions.

(5) Synthesis of DMTrOA$^{Bz}$poA$^{Bz}$poA$^{Bz}$poC$^{Bz}$poC$^{Bz}$poG$^{iB}$po- A$^{Bz}$poC$^{Bz}$poC$^{Bz}$poG$^{iB}$poG$^{iB}$poC$^{Bz}$poTpoA$^{Bz}$poTpoG$^{iB}$po $^{Ac}$Upo-cellulose:

DMTrOA$^{Bz}$poA$^{Bz}$poA$^{Bz}$poC$^{Bz}$poC$^{Bz}$poG$^{iB}$poA$^{Bz}$poC$^{Bz}$poC$^{Bz}$po-G$^{iB}$poG$^{iB}$poC$^{Bz}$poTpoA$^{Bz}$poTpoG$^{iB}$po$^{Ac}$Upo-cellulose (90.4 mg) was sysnthesized from DMTrOC$^{Bz}$poC$^{Bz}$poG$^{iB}$poA$^{Bz}$poC$^{Bz}$po-C$^{Bz}$poG$^{iB}$-poG$^{iB}$poC$^{Bz}$poTpoA$^{Bz}$poTpoG$^{iB}$po$^{Ac}$Upo-Cellulose (94.5 mg) and DMTrOA$^{Bz}$poA$^{Bz}$poA$^{Bz}$po-CE (45.1 mg) under the similar conditions. At this final process, the unreacted 5'-hydroxy group was not necessary to protect with an acetyl group.

(6) Synthesis of HOApApApCpCpG-pApCpCpGpGpCpTpApTpGOH:

DMTrOA$^{Bz}$poA$^{Bz}$poA$^{Bz}$poA$^{Bz}$poC$^{Bz}$poC$^{Bz}$poG$^{iB}$poA$^{Bz}$-poC$^{Bz}$poC$^{bz}$po G$^{iB}$poG$^{iB}$poC$^{Bz}$poTpoA$^{Bz}$poTpoG$^{iB}$-po$^{Ac}$Upo-cellulose (90.4 mg ) was treated with 0.5M N,N,N',N'-tetramethylguanidinium pyridine 2-aldoximate (in dioxane-H$_2$O (1:1 v/v, 1 ml) at 20° C. for 20 hrs in a sealed tube. To the reaction mixture 28% (w/w) aqueous ammonia (12 ml) was added, and the mixute was heated at 60° C. for 2 hrs. The solid cellulose was removed by filtration and washed with water (10 ml). The filtrate and washed solution were evaporated to dryness, and the residue was treated with 80% aqueous acetic acid (25 ml) at room temperature for 15 mins. After removal of the solvents, the residue was dissolved in 0.1M triethylammonium carbonate buffer (pH 7.5, 25 ml) was washed with diethylether (3×25 ml). Aqueous layer was evaporated to dryness and the residue was dissolved in 0.1M triethylammonium carbonate buffer (pH 7.5, 2 mins) to yield crude HOApApApCpCpG-pApCpCpGpGpCpTpApTpGOH in the solution.

(7) Purification of HOApApApCpCpG-pApCpCpGpGpCpTpApTpGOH (i) First purification of the crude product was performed by column chromatography on Biogel P2 (24×2.6 cm ID). The fractions corresponding to the first eluted peak (50 mM NH$_4$OAc, 0.1 mM EDTA, 1 ml/min) were collected and freeze-dried to give the first puified product.

(ii) Second purification of the first purified product was performed by HPLC on CDR-10 (25 cm×4.6 mm ID) using a linear gradient of 1M NH$_4$OAc-10% (v/v) aqueous EtOH to 4.5M NH$_4$OAc-10% (v/v) aqueous EtOH (80 min, 1 ml/min, 60° C.) to give the second purified product. (formula 1)

(iii) Third purification of the second purified product was performed by reverse phase HPLC (Rp-18-5μ(×77), 15 cm ×4 mm ID) using a linear gradient of 0.1M NH$_4$OAc to 0.1 M NH$_4$OAc 15% (v/v) aqueous CH$_3$CN (40 min, 1.5 ml/min, room temperature) to give the final purified product (HOApApApCpCpG-pApCpCpGpGpCpTpApTpGOH). (formula 2)

(8) Analysis of oligonucleotide:
(HOApApApCpCpGpApCpCpGpGpCpTpApT-pGOH)

(i) Digestion by phosphodiesterase:
The mixture of HOApApApCpCpG-pApCpCpGpGpCpTpApTpGOH (5 μg, 61.7 μl), 0.2M MgCl$_2$ (10 μl), 0.2M Tris-HCl (pH 8.5) (10 μl) and 0.1 mM EDTA in an aqueous solution (13.3 μl) was treated with phosphodiesterase (5 unit, 5 μl) at 37° C. for 20 min, and then heated at 100° C. for 2 min.

(ii) Analysis by HPLC:
The oliqonucleotide in the reaction misture was analyzed by HPLC (CDR-10, 25 cm×4.6 mm ID) using a linear gradient of water to 2.0M NH$_4$OAc (pH 3.4) (40 min, 1.5 ml/min, 60° C.). From each peak area observed, its nucleotide composition was determined comparing with area of a standard sample.

Calcd: pC$_{OH}$ 5,000, pA$_{OH}$ 4,000, pT$_{OH}$ 2,000, pG$_{OH}$ 4,000.

Observed: pC$_{OH}$ 4,767, pA$_{OH}$ 4,127, pT$_{OH}$ 2,054, pG$_{OH}$ 4,052.

EXAMPLE 2

Synthesis of oligonucleotides (A1, A2, B1, B2, C1, C2, D1, D2, E1, E2, F1, F2, G2, H1, H2, I1, I2, J1, J2, K1, K2, L1, L2, M1, M2, N1, N2, O1 and O2):

The following oligonucleotides were prepared by a similar manner to that of G1 described in Example 1.

(1) HOApApTpTpCpApTpGpGpGpTOH (A1)
(2) HOTpTpTpCpApGpGpApCpCpApTpGOH (A2)
(3) HOCpCpTpGpApApApCpTpCpTpGpTpGOH (B1)
(4) HOCpApGpCpGpCpCpGpCpApCpApGpApGOH (B2)
(5) HOCpGpGpCpGpCpTpGpApApCpTpGpGpTOH (C1)
(6) HOApApGpApGpCpGpTpCpApApCpCpApGpTpTOH (C2)
(7) HOTpGpApCpGpCpTpCpTpGpCpApApTpTpTOH (D1)
(8) HOCpCpApCpApTpApCpApApApTpTpGpCOH (D2)
(9) HOGpTpApTpGpTpGpGpTpGpApTpCpGpTOH (E1)
(10) HOTpApGpApApApCpCpApCpGpApTpCpAOH (E2)
(11) HOGpGpTpTpTpCpTpApCpGpTpTpCpApACOH (F1)
(12) HOGpGpTpCpGpGpTpTpTpGpTpTpGpApApGOH (F2)
(13) HOGpCpTpGpGpApGpCpCpApTpApGpCpCOH (G2)
(14) HOGpCpTpCpCpApGpCpTpCpTpCpGpTpCOH (H1)
(15) HOCpGpGpTpGpCpGpCpGpApCpGpApGpAOH (H2)
(16) HOGpCpGpCpApCpCpGpCpApGpApCpTpGOH (I1)
(17) HOCpTpApCpGpApTpApCpCpApGpTpCpTpGOH (I2)
(18) HOGpTpApTpCpGpTpApGpApCpGpApApTpGOH (J1)
(19) HOGpApApApCpApGpCpApApTpTpCpGpTOH (J2)
(20) HOCpTpGpTpTpTpCpGpTpTpCpTpTpGOH (K1)
(21) HOGpGpApGpApTpCpGpCpApApGpApApCOH (K2)
(22) HOCpGpApTpCpTpCpCpGpCpCpGpTpCpTOH (L1)
(23) HOTpApApApCpTpTpCpCpApGpApCpGpGpCOH (L2')
(24) HOGpApApGpTpTpTpApCpTpGpTpGpCpTOH (M1')
(25) HOTpTpCpApGpTpGpGpApGpCpApCpApGOH (M2)
(27) HOCpApCpTpGpApApGpCpCpApGpCpAOH (N1)
(28) HOGpCpGpGpApTpTpTpTpGpCpTpGpGpCOH (N2)
(29) HOApApApTpCpCpGpCpGpTpGpApTpApGOH (O1)
(30) HOGpApTpCpCpTpApTpCpApCOH (O2)

EXAMPLE 3

Synthesis of oligonucleotides (a1, a2, a3, a4, a5, a6, b1, b2, b3, b4, b5, b6, c1, c2, c3, c4, c5, c6, d1, d2, d3, d4, d5, d6, e1, e2, e3, e4, e5, 11, 12 and 13):

The following oligonucleotides were prepared by a similar manner to that of G1 described in Example 1.

(1) HOApApTpTpCpApTpGpTpGpTpTOH (a1)
(2) HOApCpTpGpCpCpApGpGpApCpCpApTOH (a2)
(3) HOApTpGpTpApApApApGpApApGpCpApGOH (a3)
(4) HOTpGpGpCpApGpTpApApCpApCpApTpGOH (a4)
(5) HOTpTpTpApApCpApTpApTpGpGpGpTpCpCOH (a5)
(6) HOApApGpGpTpTpTpCpTpGpCpTpTpCpTOH (a6)
(7) HOApApApCpCpTpTpApApGpApApApTpAOH (b1)
(8) HOCpTpTpApApTpGpCpApGpGpTpCpAOH (b2)
(9) HOTpTpTpCpApGpApTpGpApCpGpCpGpAOH (b3)
(10) HOApTpTpApApApGpTpApTpTpTpCpTpTOH (b4)
(11) HOApTpCpTpGpApApTpGpApCpCpTpGpCOH (b5)
(12) HOTpTpCpCpApTpTpApTpCpCpGpCpTpApCOH (b6)
(13) HOTpApApTpGpGpApApCpCpTpTpTpTpCOH (c1)
(14) HOTpApGpCpApTpTpTpGpApApApGOH (c2)
(15) HOApApTpTpGpGpApApApApGpApGpApGOH (c3)

-continued

| | |
|---|---|
| (16) | HOTpGpCpCpTpApApGpApApApApGpApGOH (c4) |
| (17) | HOTpCpCpApApTpTpCpTpTpCpApApApAOH (c5) |
| (18) | HOCpTpGpTpCpApCpTpCpTpCpCpTpCpTpTOH (c6) |
| (19) | HOApGpTpGpApCpApGpApApApApApTpAOH (d1) |
| (20) | HOApTpGpCpApGpApGpCpCpApApApTpTOH (d2) |
| (21) | HOGpTpCpTpCpCpTpTpTpApCpTpTOH (d3) |
| (22) | HOCpTpCpTpGpCpApTpTpApTpTpTpTpTOH (d4) |
| (23) | HOApGpGpApGpApCpApApTpTpTpGpGOH (d5) |
| (24) | HOApApApGpCpTpTpGpApApGpTpApApAOH (d6) |
| (25) | HOCpApApGpCpTpTpTpCpApApApApAOH (e1) |
| (26) | HOCpTpTpTpApApGpGpApTpGpApCpCpAOH (e2) |
| (27) | HOGpApGpCpApTpCpCpApApApApGpApGOH (e3) |
| (28) | HOCpCpTpTpApApApGpTpTpTpTpTpGpAOH (e4) |
| (29) | HOGpGpApTpGpCpTpCpTpGpGpTpCpApTOH (e5) |
| (30) | HOTpGpTpGpTpApApTpGpApTpApGOH (11) |

| | |
|---|---|
| (1) | HOApApTpTpCpApTpGpGpCpTOH (SA) |
| (2) | HOGpGpTpTpGpTpApApGpApApCpTpTpCpTOH (SB) |
| (3) | HOTpTpTpGpGpApApGpApCpTpTpTOH (SC) |
| (4) | HOCpApCpTpTpCpGpTpGpTpTpGpApTpApGOH (SD) |
| (5) | HOTpTpApCpApApCpCpApGpCpCpApTpGOH (SE) |
| (6) | HOCpCpApApApApGpApApGpTpTpCOH (SF) |
| (7) | HOCpGpApApGpTpGpApApApGpTpCpTpTOH (SG) |
| (8) | HOGpApTpCpCpTpApTpCpApApCpAOH (SH) |

EXAMPLE 7

The following oligonucleotides (A' to N') were prepared by a similar manner to that of Example 1.

| | |
|---|---|
| (1) | HOGpApTpCpCpTpCpGpApGpApTpCpApAOH (A') |
| (2) | HOGpCpCpTpTpTpApApTpTpCpApTpCpTpCpGpApGOH (B') |
| (3) | HOTpTpApApApApGpGpCpTpCpCpTpTpTpTpGpGpAOH (C') |
| (4) | HOApApApApApGpGpCpTpCpCpApApApApGpGpAOH (D') |
| (5) | HOGpCpCpTpTpTpTpTpTpTpTpTpGOH (E') |
| (6) | HOTpCpGpApCpApApApApAOH (F') |
| (7) | HOGpApTpCpCpTpCpGpApGpGpCpTOH (G') |
| (8) | HOGpTpTpTpApApTpCpApGpCpTpCpGpApGOH (H') |
| (9) | HOGpApTpTpApApApCpCpGpApApTpCpApAOH (I') |
| (10) | HOGpCpCpTpTpTpApApTpTpGpApTpTpCpGOH (J') |
| (11) | HOGpCpCpTpTpTpTpTpTpTpTpTpTOH (K') |
| (12) | HOTpCpTpCpCpApApApApApAOH (L') |
| (13) | HOGpGpApGpApCpApApCpGOH (M') |
| (14) | HOTpCpGpApCpGpTpTpGOH (N') |

| | |
|---|---|
| (31) | HOTpApCpApCpApCpTpCpTpTpTpTOH (12) |
| (32) | HOGpApTpCpCpTpApTpCpApTOH (13) |

EXAMPLE 4

The following oligonucleotide (m1 and m2) were prepared by a simlar manner to that of Example 1.

(1) HOApGpCpTpTpGpApApGpTpApApApApCpApTpGOH (m1)

(2) HOApApTpTpCpApTpGpTpTpTpTpApCpTpTpCpAOH (m2)

EXAMPLE 5

Synthesis of oligonucleotides (A, B, C, D, E, F, G, H, I, J, K, L, M and N):

The following oligonucleotides were prepared by a similar manner to that of Example 1.

| | |
|---|---|
| (1) | HOApApTpTpGpCpCpGpApCpAOH (A) |
| (2) | HOCpGpTpTpApTpGpApTpGpTpCpGpGpCpAOH (B) |
| (3) | HOTpCpApTpApApCpGpGpTpTpCpTpGpGpCOH (C) |
| (4) | HOGpApApTpApTpTpTpGpCpCpApGpApApCOH (D) |
| (5) | HOApApApTpApTpTpCpTpGpApApApApTpGpAOH (E) |
| (6) | HOTpCpApCpApGpCpTpCpApTpTpTpCpAOH (F) |
| (7) | HOGpCpTpGpTpGpApCpApApTpTpApApTpTOH (G) |
| (8) | HOGpTpTpCpGpApTpGpApTpTpApApTpTpGOH (H) |
| (9) | HOCpApTpCpGpApApCpTpApGpTpTpApApCpOH (I) |
| (10) | HOGpCpGpTpApCpTpApGpTpTpApApCpTpGOH (J) |
| (11) | HOTpApGpTpApCpGpCpApApApGpTpTpCpApCOH (K) |
| (12) | HOCpTpTpTpTpApCpGpTpGpApApCpTpTOH (L) |
| (13) | HOGpTpApApApApApGpGpGpTpApTpCpGOH (M) |
| (14) | HOApApTpTpCpGpApTpApCpCOH (N) |

EXAMPLE 6

Synthesis of oligonucleotides (SA, AB, SC, SD, SE, SF, SG, and SH):

EXAMPLE 8

Preparation of $^{59}$Val-IGF-I gene

Ligation of chemically synthesized oligonucleotides:
Aliquots of each oligonucleotides (A1-O1) (0.4 nM) were phosphorylated with 4 units of T4 polynucleotide kinase (made by BRL) in 100 μl of a solution containing 74 mM Tris-HCl (pH 7.6), 10 mM DTT, 1.6 mM mercaptoethanol, 10 mM MgCl$_2$ and 0.5 mM ATP for 20 minutes at 37° C. After the reaction was completed, the enzyme in the reaction mixture was deactivated by incubation at 100° C. for 5 minutes. Ligation of the phosphorylated oligonucleotides was carried out as shown in formula 3 to give firstly fragments of ten blocks and ultimately the $^{59}$Val-IGF-I gene for cloning. Ligations were carried out with T4 DNA ligase (7 units) in a solutiono containing 100 mM ATP (0.5 μl) for 23 hours at 4° C. (standard condition). The ligation products of oligonucleotides in each step were identified by staining with ethidium bromide following electroelution on a 2-16% gradient PAGE in tris-EDTA buffer.

EXAMPLE 9

Modecular cloning of the $^{59}$Val-IGF-I gene

The plasmid pBR322 was digested with BamHI and EcoRI restriction endonucleases. Reaction was terminated by heating at 65° C. for 5 minutes and the fragments separted by electrophoresis on a 0.5% agarose gel. The 3985 bp large fragment from pBR322 was recovered and ligated with T4 DNA ligase for 18 hours at 12° C. to the 224 bp $^{59}$Val-IGF-I gene. The ligated mixture was transformed into E. coli HB101 by Kushner's method and ampicillin resistant transformants were selected on the plate containing tetracycline (25 μg/ml). Plasmid DNA isolated from one of five clones resistant to ampicillin and sensitive to tetracycline was digested with EcoRI and BamHI and compared with appropriate size markers. The expected 224 bp IGF-I fragment was genreated. This plasmid which was characterized by complete nucleotide sequencing of the $^{59}$Val-IGF-I gene was named pSdV2 and was used for the construction of expression vector.

EXAMPLE 10

Sequencing of $^{59}$Val-IGF-I gene in plasmid pSdV2

For the sequencing of $^{59}$Val-IGF-I gene, plasmid pSdV2 was digested with EcoRI and then treated with AMV reverse transcriptase (purchased from Seikagaku Kogyo Co., Ltd.) in the presence of α-$^{32}$P-ATP at 37° C. for 30 minutes. The linear plasmid labeled with $^{32}$P was digested with BamHI to give two fragments (224 bp, 4.1 kbp). The smaller fragment (224 bp) was recovered by preparative polyacrylamide gel electrophoresis and sequenced according to the manual of Maxam-Gilbert method. On the other hand, plasmid pSdV2 was digested with BamHI firstly and then labeled with $^{32}$P as described above. The linear plasmid was digested with EcoRI to give two fragments (226 bp, 4.0 kbp). The smaller fragments (224 bp) was analyzed by Maxam-Gilbert method as above. The results of sequencing from both side of $^{59}$Val-IGF-I gene were agreed with designed $^{59}$Val-IGF-I gene.

EXAMPLE 11

Prepartion of protein peptide LH gene

Ligation of chemically synthesized oligonucleotides: Aliquots of each oligonucleotides (a2–12) (0.4 nM) were phosphorylated with 2.5 units of T4 polynucleotide kinase in 40 μl of a solution containing 50 mM Tris-HCl (pH 7.6), 20 mM DTT, 50 μg/ml BSA, 1 mM spermidine, 10 mM MgCl$_2$ and 2 mM ATP for 3 hours at 37° C. After the reaction was completed, the enzyme in the reaction mixture was deactivated by incubation at 100° C. for 5 minutes. Ligation of the phosphorylated oligonucleotides and two oligonucleotides (a1 and 13) was carried out as shwo in formula 9 to give firstly fragment six blocks and ultimately protein peptide LH gene (236 bp) for cloning. Ligation was carried out with T4 DNA ligase (5 units) in a solution containing 50 mM ATP (1 μl) for 5 hours at 16° C. The ligation products of oligonucleotides in each step were identified by staining with ethidium bromide following electroelution on a 2–16% gradient PAGE in Tris-EDTA buffer.

EXAMPLE 12

Molecular cloning of protein peptide LH gene

The protein peptide LH gene (236 bp) which synthesized as above was inserted into pBR 322 by a similar manner to that of Example 9. The plasmid (pLH107) obtained from E. coli HB101 transformant was characterized by restriction enzyme analysis to have protein peptide LH (236bp).

EXAMPLE 13

Construction of the synthetic typtophan promoter gene I

Each oligonucleotides (B-M) of block I, II, III were phosphorylated with T4 polynucleotide kinase and then ligated wit T4 DNA ligase as described above. These blocks (I–III) and unphosphorylated oligonucleotides (A, N) were condensed successively. The last ligation product was purified by preparative 7.5% PAGE to five the 107 bp synthetic trp promoter I gene.

EXAMPLE 14

Molecular cloning of the synthetic trp promoter I gene

The plasmid pBR325 was digested with EcoRI and then linear pBR325 was ligated with the synthetic trp promoter I gene prepared above. The transformants of E. coli HB101 by the above ligation mixture were screened on the plates contained antibiotics to give four $^R$Amp $^S$Cm colonies. The plasmids obtained from four colonies were digested with HpaI, respectively. The fragments obtained from these plasmids by HindIII and EcoRI digestion were compared with the fragments of pBR325 by HindIII and EcoRI digestion. One of four plasmids has the correct directed promoter gene (synthetic tryp promoter I gene) and the other were inserted in reverse direction.

EXAMPLE 15

Construction of the tryptophan promoter II gene

Each oligonucleotides (B to SG) of block I', II', III' and IV' were phosphorylated with T4 polynucleotide kinase and then ligated with T4 DNA ligase as described above. These blocks (I' to IV') and unphosphorylated oligonucleotides (A and SH) were condensed successively. The last ligation product was pruified by preparative 7.5% PAGE to give the 163 bp synthetic trp promoter II gene.

EXAMPLE 16

Coning of the synthetic trp promoter II gene

The synthetic trp promoter II gene constructed in Example 15 was ligted with EcoRI, BamHI fragment of pBR322 and the E. coli HB101 was transformed with the ligation product. The plasmid obtained from the transformant of $^R$Amp and $^S$Tet was digested with HpaI to confirm a band (4.1 kbp), and then digested with BamHI to confirm a band of 90 bp on PAGE. Moreover, the fragment of 56 bp by EcoRI-BamHI digestion was confirmed by the comparison with size marker on PAGE. This plasmid was named pTrpEB7 and used construction of expression vector.

EXAMPLE 17

Construction of $^{59}$Val-IGF-I expression vector (pSdV2-322trp)

The synthetic trp promoter II vector (pTrpEB7) was digested with EcoRI and BamHI to give a large fragment (4.1 kbp) by PAGE. This fragment was ligated with the $^{59}$Val-IGF-I gene prepared from a plasmid pSdV2. The ligated mixture was transformed into E. coli HB101 and ampicillin resistant and tetracycline-sensitive transformants were selected. The obtained plasmid pSdV2-322trp was digested with EcoRI and BamHI to confirm the $^{59}$Val-IGF-I gene (224bp) on 7.5% PAGE.

EXAMPLE 18

Sequencing of $^{59}$Val-IGF-I gene and synthetic trp promoter I gene in plasmid pSdV2-322trp For the sequencing of $^{59}$Val-IGF-I gene and synthetic trp promoter I gene by Maxam-Gilbert method, plasmid pSdV2-322trp was digested with EcoRI and treated with bacteria alkaline phosphatase at 37° C. for 1 hour. After phenol extraction and ethanol precipitation the plasmid was phosphorylated with T4 polynucleotide kinase in the presence of γ-$^{32}$p-ATP at 37° C. for 1 hour, finally was digested with HinfI to afford two fragments (1100 bp, 480 bp). Each fragment was sequenced according to the manual of Maxam-Gilbert method. The resulted sequence of $^{59}$Val-IGF-I and synthetic trp promoter gene agreed with that designed.

EXAMPLE 19

Construction of protein peptide LH expression vector (pLHtrp)

The synthetic trp promoter II vector (pTrpEB7) prepared in Example 16 was digested with EcoRI and BamHI to give a large fragment (4.1 kbp) by preparative agarose gel electrophoresis. This fragments was ligated with protein peptide LH gene prepared from a plasmid pLH107 by EcoRI and BamHI digestion. The ligated mixture was transformed into E. coli HB101 to give ampicillin resistant and tetracycline sensitive transformants. The plasmid (pLHtrp) obtained from the transformant was digested with EcoRI and BamHI to confirm the protein peptide LH gene (226 bp) on 7.5% PAGE.

EXAMPLE 20

Construction of $^{59}$Val-IGF-I expression vector

Oligonucleotide (ml) prepared in Example 4 (1) was phosphorylated with T4 polynucleotide kinase as described in Example 8. The phosphorylated oligonucleotide, oligonucleotide m2 prepared in Example 4 (2) and $^{59}$Val-IGF-I gene (224 bp) which was prepared from plasmid pSdV2 prepared in Example 10 were mixed and treated with T4 ligase in a solution containing 100 mM ATP for 23 hours at 4° C. The ligation mixture was purified by preparative PAGE to give $^{59}$Val-IGF-I gene with linker (242 bp). The gene (242 bp) was ligated with the fragment obtained from pLHtrp by HindIII-BamHI digestion, and then the ligation mixture was transformed into E. coli HB101. The E. coli HB101 containing plasmid pLHSdVtrp was named E. coli F-5 and deposited with Fermentaiton Research Institute Agency of Industrial Science and Technology (1-3, Higashi 1 chome Yatabe-machi Tsukuba-gun Ibaraki-ken 305, Japan) under deposit number of FERM-P 7644 on May 18, 1984, and then converted to Budapest Treaty route of the same depository on Feb. 28, 1985 under the new deposit number of FERM BP-728. The plasmid (pLHSdVtrp) obtained from the transformant was digested with EcoRI and BamHI (198, 224 bp), EcoRI and PstI (198, 859 bp), HindIII and BamHI (242 bp), HpaI-BamHI (456 bp) to confirm the synthetic trp promoter I, protein peptide LH and IGF-I gene on 7.5% PAGE.

This process is shown in formula 14.

EXAMPLE 22

Expression of $^{59}$Val-IGF-I gene

An overnight culture of E. coli containing plasmid pSdV2-322trp in L broth containing 20 μg/ml ampicillin was diluted 1:25 in M9 medium containing 0.2% glucose, 0.5% casamino acid (acid-hydrolyzed casein) and 50 μg/ml vitamine B1. β-indole acrylic acid was added to a final concentration of 10 μg/ml when A$_{600}$ was 0.4. Then the cells were incubated for 3 hours and collected by centrifugation (6 krpm, 4° C., 5 minutes). Cell were opened by sonication and cleared of debris by centrifugation. The supernatants were fixed with 3M acetic acid. The precipitate was removed by centrifugation (20 krpm, 4° C., 10 minutes), the supernatants were freeze-dried. For assay the sample was suspended in 4 ml of medium (0.01M PBS, 0.025M EDTA, and 0.5% BSA) and adjusted at pH 7-8 with 0.1N NaOH. After removal of insoluble substance by centrifugation, the supernatants were stored at −20° C. until assay.

EXAMPLE 23

RIA of $^{59}$Val-IGF-I

The RIA of $^{59}$Val-IGF-I was followed the method established by N. Yanaihara. With 0.1 ml of the above sample or standard sample (IGF-I fragment (26–46)) sample buffer [0.5% BSA in 0.01M PBS, 0.025M EDTA (pH 7.4) (0.4 ml)], rabbit antiserum (0.1 ml) of IGF-I (26–46) and $^{125}$I-IGF-I (26–46) (0.1 ml) were mixed. The mixture was allowed to stand for 48 hours at 4° C., and then added with rabbit serum (0.1 ml), rabbit γ-globulin antiserum (0.1 ml) and 5% PEG6000 (0.9 ml). After standing for additional 2 hours at 4° C. the pellet was collected by centrifugation (3 krpm, 4° C., 30 minutes), and measured radio activity by γ-counter. The content of $^{59}$Val-IGF-I was calculated from this radio activity.

EXAMPLE 24

Expression of a gene coding for $^{59}$Val-IGF-I fused with protein peptide LH in E. coli F-5

An overnight culture of E. coli F-5 (which is E. coli HB101 containing plasmid pLHpSdVtrp) FERM BP-728 in L broth containing 50 μg/ml ampicillin was dilluted 1:20 in M9 medium containing 0.2% glucose, 0.5% casamino acid (acid-hydrolyzed casein), 50 μg/ml vitamin B1 and 25 μg/ml ampicillin. β-Indole acylic acid was added to a final concentration of 10 μg/ml when A$_{600}$ was 0.5. Then the cells were incubated for 2 hours and collected by centrifugation (5 krpm, 4° C., 5 minutes).

EXAMPLE 25

Molecular cloning of terminator S gene

Each oligonucleotide (B', C', D' and E') were phosphorylated with T4 polynucleotide kinase and then treated with T4 DNA ligase as described in Example 8. The ligation mixture and two oligonucleotides (A' and F') were mixed and treated with T4 DNA ligase. The ligation product was purified by preparative PAGE and mixed with the large fragment of pBR322 by BamHI-SalI digestion. Ligation of the mixture was carried out with T4 ligase under the standard condition. The ligation mixture was transformed into E. coli HB101 by Kushner's method and ampicillin resistant transformants were selected on the plate containing tetracycline. Plasmid DNA isolated from a clone resistant to ampocillin and sensitive to tetracycline was digested with AvaI to show 817 bp fragment and with BamHI-SalI to confirm terminator S gene (47 bp). The palsmid was named pTerS21 and used for the construction of expression vector.

EXAMPLE 26

Molecular cloning of teminator L gene

Each oligonucleotides (C', D', H', I', J', K', L' and M') were phosphorylated with T4 polynucleotide kinase and then treated with T4 DNA ligase as described in Example 8. The ligation mixture and two oligonucleotides (G' and N') were mixed and treated with T4 DNA ligase. The ligation product was purified by preparative PAGE and mixed with the large fragment (4087 bp) of pBR322 by BamHI-SalI digestion. Ligation of the mixture was carried out with T4 DNA ligase under the standard condition. The ligation mixture was transformed into E. coli HB101 by Kushner's method and ampicillin resistant transformants were selected on the plate containing tetracycline. Plasmid DNA isolated from a clone resistant to ampicillin and sensitive to tetracycline was digested with AvaI to show 3.32 kbp and 839 bp fragments on 0.8% agarose gel electrophoresis and 7.5% PAGE. The plasmid containing terminator L gene was named pTerL and used for the construction of expression vector.

EXAMPLE 27

Construction of $^{59}$Val-IGF-I expression vector containing terminator S gene pTerS21 containing terminator S gene was digested with PstI and BamHI to give a larger fragment (3005 bp) by preparative agarose gel electrophoresis. The gene (3005 bp) was ligated with the smaller fragment (1281 bp) obtained from pLHSdVtrp by BamHI-PstI digestion under the standard condition and then the ligation mixture was transformed into E. coli HB101. The plasmid (pLHSdVtrpS) obtained from the trans formant resistant to ampicillin was digested with PstI-SalI (1331, 2958 bp), and HindIII-SalI (289 bp) to confirm terminator S gene on 7.5% PAGE.

EXAMPLE 28

Construction of $^{59}$Val-IGF-I expression, vector containing terminator L gene Plasmid pTerL containing terminator L gene was digested with PstI and BamHI to give a larger fragment (3027 bp) by preparative agarose gel electrophoresis. The gene (3027 bp) was ligated with the smaller fragment (1281 bp) obtained from pLHSdVtrp by BamHI-PstI digestion under the standard condition and then the ligation mixture was transformed into E. coli HB101. The plasmid (pLHSdVtrpL) obtained from the trans formant resistant to ampicillin was digested with PstI-SalI (1353, 2958 bp) and HindIII-SalI (311 bp) to confirm terminator L gene on 7.5% PAGE.

EXAMPLE 29

Construction of expression vector of $^{59}$Val-IGF-I: fused with β-galactosidase gene (pSdV2-lac)

Charon 25 phage DNA (which was given by Dr. Imai) was digested with EcoRI to give four fragments (19.9, 10.7, 6.6 and 5.7 kbp). The fragment (6.6 kbp), which was contained lactose promoter, operator and most of Z gene, was recovered by preparative agarose gel electrophoresis. On the other hand, pSdV2 was digested with EcoRI and then treated with bacteria alkaline phosphatase (BAP). The lineared plasmid was ligated in amounts equimolar with the above promoter gene (6.6 kbp) in the presence of T4 ligase at 4° C. The transformant of E. coli HB101 with this ligated mixture were selected for resistance to ampicillin on 5-bromo-4-chloro-indolylgalactoside (Xgal) medium. On this indicator plate colonies constitutive for the synthesis of β-galactosidase by virtue of the increased number of lac operators titrating repressor are identified by their blue color. Approximately 13 percent of the colonies were blue and they were sensitive for tetracycline. The plasmids obtained from four colonies were digested with BamHI and HindIII, respectively. One of four plasmids has the correct directed promoter gene and the other were inserted in reverse direction. The obtained plasmid pSdV2-lac was digested with EcoRI and BamHI to confirm the $^{59}$Val-IGF-I gene (224 bp) by 7.5% PAGE and the E. coli containing the plasmid was named as E. coli F-1. This process is shown in formula 19.

EXAMPLE 30

Expression of $^{59}$Val-IGF-I fused with β-galactosidase gene (pSdV2-lac)

An overnight culture of E. coli HB101 containing plasmid pSdV2-lac in L broth (15 ml) containing 20 μg/ml ampicillin was diluted in L broth (300 ml), and then the cells were incubated at 37° C. When $A_{600}$ was 0.8, Isopropylthiogalactoside (IPTG) was added to a final concentration of 0.1 mM. After additional incubation for 2 hours, the cells were collected by centrifugation (5 krpm, 4° C., 5 minutes) and were suspended in 70% formic acid containing BrCN (10 mg/ml). The mixture was allowed to stand for 24 hours at room temperature and the solvent was evaporated in vauco. The residue was suspended in cold 3M acetic acid (9 ml). After removal of insoluble substance by centrifugation, the supernatants were stored at −20° C. until assay.

EXAMPLE 31

Construction of expression vector of $^{59}$Val-IGF-I fused with β-galactosidase (pSdV2-NT49)

pNT49, made by Dr. Imai (Institute of Virus Research, Kyoto University), is the plasmid containing pL promoter, tryptophan (trpA) and lactose structural genes. This plasmid pNT49 was digested with BamHI and then partially digested with EcoRI and followed by preparative agarose gel electrophoresis to recover the fragments of approximately 8 kbp. This fragments were ligated with $^{59}$Val-IGF-I gene (224 bp) obtained above and the ligated mixture was transformed into E. coliMM294 to give the ampicillin resistant transformants. The plasmid from one of these transformants was digested with EcoRI and BamHI to confirm the presence of $^{59}$Val-IGF-I gene (224 bp).

On the other hand the receipient cell E. coli HI2019/pNT204 was prepared as described below. E. coli HI2019 (F− CSH50* ara trpA(oc) recA, * see J. H. Miller Experiments in Molecular Genetics, Cold Spring Harber Laboratory (1972)) was transformed with plasmid pNT204 containing CI857 gene in pSC101 (this plasmid (pNT204 was given us by Dr. Imai) to give the transformant of resistance for tetracycline. The receipient cell E. coli HI2019/pNT204 was tranformed with plasmid pSdV2-NT49 obtained above to give the transformant of resistance for ampicillin and tetracycline. The plasmid obtained from this transformant was digested with EcoRI and BamHI to confirm the presence of $^{59}$Val-IGF-I gene (224 bp) by 7.5% PAGE. The E. coli HI2019/pNT204 containing pSdV2-NT49 was named as E. coli F-4. This process is shown in formula 20.

EXAMPLE 32

Expression of $^{59}$Val-IGF-I fused with β-galactosidase gene (pSdV2-NT49)

An overnight culture of E. coli HI2019 containing plasmid pSdV2-NT49 and pNT204 in L broth (5 ml) (ampicillin (25 μg/ml) and tetracycline (25 μg/ml) at 30° C. was diluted in LP broth (L broth+0.2M potassium phosphate buffer+1% glucose) (100 ml). The culture were grown at 30° C. to $A_{600}=0.5-0.6$ and then shifted to 42° C. After additional incubation for 3 hours at 42° C. the cells were collected and suspended with 70% formic acid containing BrCN (10 mg/ml) and allowed to stand for 24 hours at room temperature. The solvent was evaporated under reduced pressure and the residue was suspended in 3M acetic acid (3 ml). The mixture was permitted to stand overnight at room temperature and diluted three times with sterile water. After removal of insoluble substance by centrifugation, the supernatant was freeze-dried and stored at −20° C. until assay.

EXAMPLE 33

Isolation and purification of $^{59}$Val-IGF-I (1) Isolation and purification of fused $^{59}$Val-IGF-I Wet cell paste (60 g) was suspended in 150 ml of 10 mM PBS-EDTA (pH 8.0) and cells were lysed by sonication. The cells debis was pelleted by centrifugation at 18,000 rpm for 30 minutes. The pellet was dissolved in 50 ml of 0.1M Tris-HCl (pH 8.0)/8M urea and 0.1M dithiothreitol and centrifuged at 35,000 rpm for 30 minutes at 25° C. The supernatant was collected and applied to a Sephacryl S300 superfine column (5.0×86.6 cm; 1700 ml resin) equilibrated with 0.1M Tris-HCl (pH 8.0)/8M urea and 10 mM 2-mercaptoethanol. Elution was carried out at 4° C. with equilibration buffer, at a flow rate of 0.6 ml/min. Fractions of 17 ml were collected. Sephacryl S300 chromatography was conducted. Assays were performed immediately following fractionation for all chromatography steps. Active fraction were collected and the pooled fraction of 204 ml was dialyzed for 3 hours at room temperature against 8 liters of 1M acetic acid aqueous solution and then overnight against 8 liters of fresh 1M acetic acid aqueous solution. The fraction dialyzed was lyophilized to give fused $^{59}$Val-IGF-I of 240 mg which contains a desired component.

(2) Elimination of protein peptide LH from fused $^{59}$Val-IGF-I with cyanogen bromide:

The fused $^{59}$Val-IGF-I (240 mg) obtained by procedure (1) was dissolved in 12 ml of 80% formic acid. Cyanogen bromide (240 mg) was added and the mixture was allowed to react overnight below 25° C. with stirring. After addition of 108 ml of distilled water, formic acid and cyanogen bromide was removed by lyophilization. The residue was dissolved in 6 ml of 1M Tris-HCl (pH 8.0)/8M urea and 50 mM 2-mercaptoethanol. The resulting solution was stirred for 4 hours at 25° C. and dialyzed twice for 2 hours at room temperature against 150 ml of 0.01 ml of 0.01M ammonium acetate (pH 4.6)/8M urea and 50 mM 2-mercaptoethanol (Buffer A). The solution dialyzed was applied to a cationic ion exchange resin CM 52 column (1.6×15.0 cm; 30 ml resin) equilibrated with Buffer A. The column was washed with Buffer A (60 ml) at room temperature at a flow rate of 0.5 ml/min and eluted with a linear gradient from Buffer A (250 ml) to 0.2M ammonium acetate (pH 5.0)/8M urea and 50 mM 2-mercaptoethanol (250 ml). Fractions of 2.75 ml were collected. Cationic ion exchange chromatography was conducted. Active fractions were collected and the fraction pooled was dialyzed twice against 4 liters of 1M acetic acid aqueous solution/10 mM 2-mercaptoethanol at room temperature for 4 hours.

(3) High-performance liquid chromatography:

The dialyzed fraction containing radioimmune activity obtained by procedure (2) was applied:
Column: Beckman Ultropore RPSC (4.6×75 mm)
Flow rate: 1 ml/min
Elution: Linear gradient from 10% to 60% acetonitrile in 0.01M trifluoroacetic acid over 50 minutes The procedure was repeated 30 times and fractions containig reduced $^{59}$Val-IGF-I were collected and the main peak with a retention time of 28.118 minutes corresponds to reduced $^{59}$Val-IGF-I.

Thus pure reduced $^{59}$Val-IGF-I was obtained in 80% yield (about 7 mg) by the procedures described above.

The reduced $^{59}$Val-IGF-I was converted to oxidized $^{59}$Val-IGF-I by a usual manner of refolding.

EXAMPLE 34

Expression of a gene coding for $^{59}$Val-IGF-I fused with protein peptide LH using plasmid pLHSdVtrpS

*E. coli* HB101 containing plasmid PLHSdVtrpS was cultured under the condition of β-indoleacrylic acid induction according to a similar manner to that of Example 24. The collected cells were lysed and the fused $^{59}$Val-IGF-I was isolated as described in Example 33 (1). The fused $^{59}$Val-IGF-I was treated with cyanogen bromide and the crude $^{59}$Val-IGF-I was purified as described in Example 33 (2) to give pure $^{59}$Val-IGF-I.

EXAMPLE 35

Expression of a gene coding for $^{59}$Val-IGF-I fused with protein peptide LH using plasmid pLHSdVtrpL Expression of $^{59}$Val-IGF-I using plasmid pLHSdVtrpL was carried out according to a similar manner to that of Example 24.

EXAMPLE 36

Analysis of reduced $^{59}$Val-IGF-I (1) Amino acid composition:

Analysis was performed on the material prepared by Example 33 using a Walters amino acid analysis system, of which SH group was protected with carboxymethyl ($CH_2COOH$) function by the method described in the literature.

TABLE 1

| Amino acid compositions of reduced $^{59}$Val-IGF-I values are given in Mol %. | | |
|---|---|---|
| Amino acid | Residue per molecule | Nearest integer | Expected |
| CM-Cys | 5.6 | 6 | 6 |
| Asp | 5.2 | 5 | 5 |
| Thr | 2.6 | 3 | 3 |
| Ser | 4.9 | 5 | 5 |
| Glu | 5.9 | 6 | 6 |
| Pro | 5.4 | 5 | 5 |
| Gly | 7.4 | 7 | 7 |
| Ala | 5.6 | 6 | 6 |
| Val | 3.7 | 4 | 4 |
| Met | 0 | 0 | 0 |
| Ile | 0.5 | 1 | 1 |
| Leu | 5.1 | 5 | 6 |
| Tyr | 2.5 | 3 | 3 |
| Phe | 3.6 | 4 | 4 |
| Lys | 3.2 | 3 | 3 |
| Arg | 8.4 | 8 | 6 |
| Total | | 70 | 70 |

Calculation of amino acid residues was normalized to 70 on the basis of DNA sequence data presented in this specification.

(2) Amino acid sequence analysis of $^{59}$Val-IGF-I:

The amino acid sequence of the NH₂ terminus of the peptide was determined by the Edman procedure (DI-BITC method) [J. Y. Chang et al: Biochem. J., 153, 607(1976), Biochem. Biophys. Acta., 578, 188(1979)] with a Bechman sequencer model 890D. While, the amino acid sequence of the C terminus of the peptide was determined by the carboxypeptidase digestion method as shown in formula 21.

(3) Polyacrylamide gel electrophoresis:
Polyacrylamide gel electrophoresis (PAGE) was carried out according to Swank and Munkres.
The $^{59}$Val-IGF-I showed a single band at the position of about 5000 dalton on PAGE. [Natural IGF-I shows a band at the position of about 5000 dalton on PAGE in the literature [R. E. Humbel et al, Proc. Natl. Acad. Sci. USA 73, 2365–2369(1976)]].

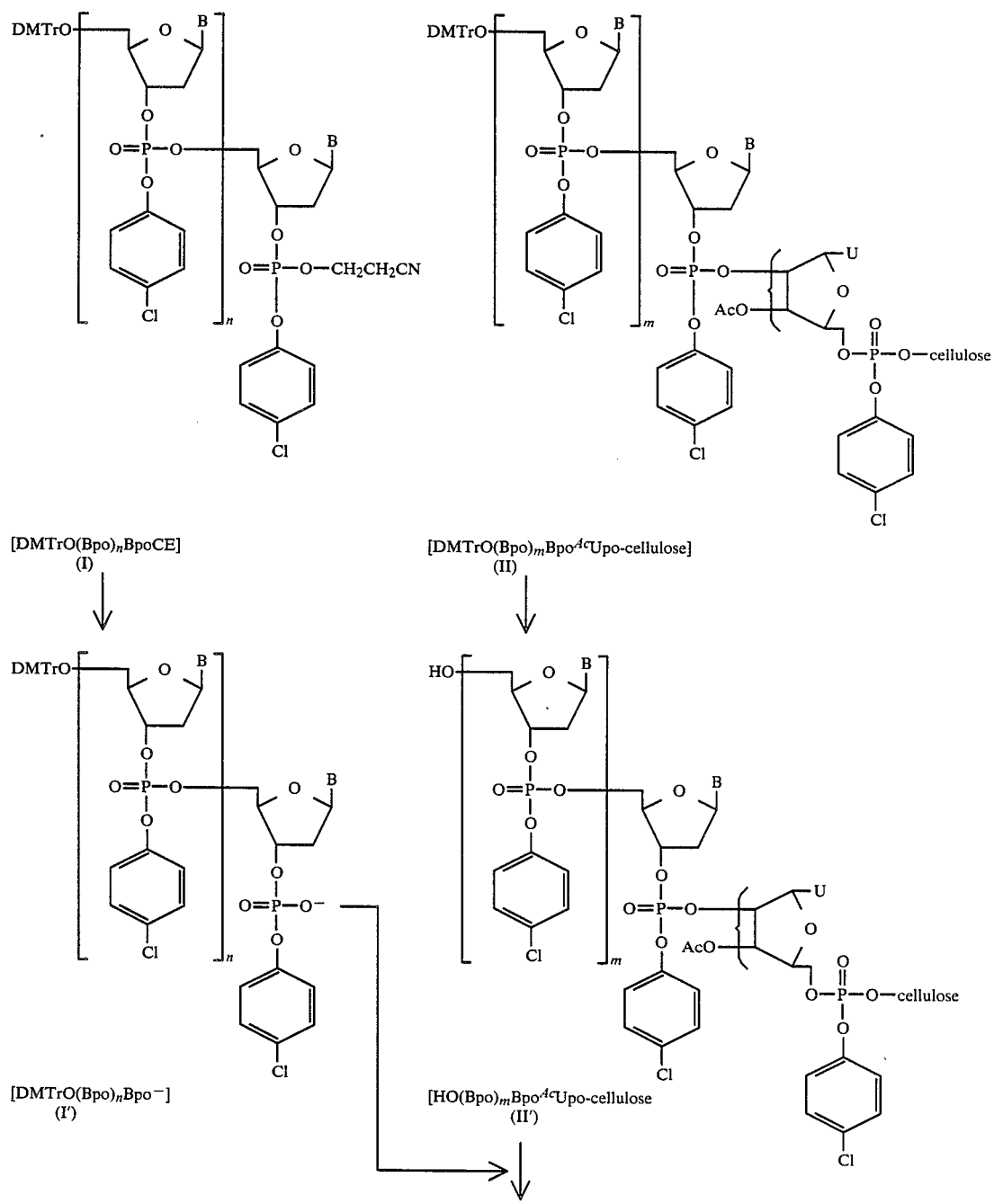

formula 1
Building up of oligonucleotides from smaller units by successive coupling reactions -continued
formula 1
Building up of oligonucleotides from smaller units by successive coupling reactions
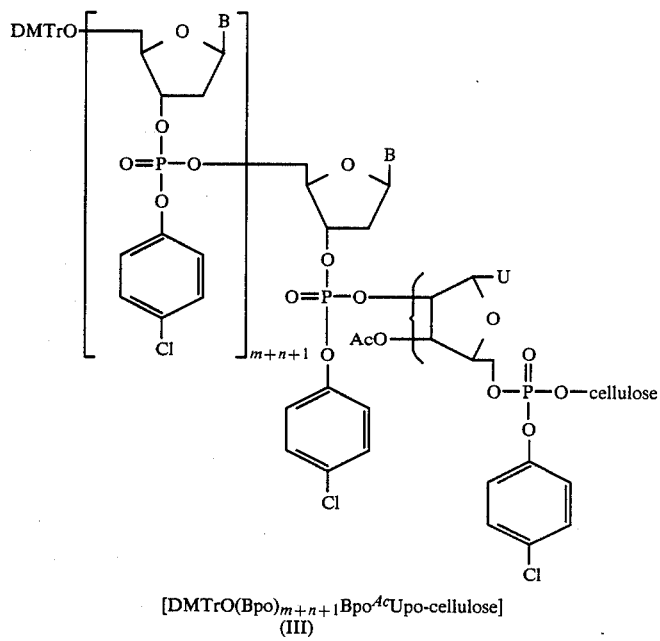
[DMTrO(Bpo)$_{m+n+1}$Bpo$^{Ac}$Upo-cellulose]
(III)
↓
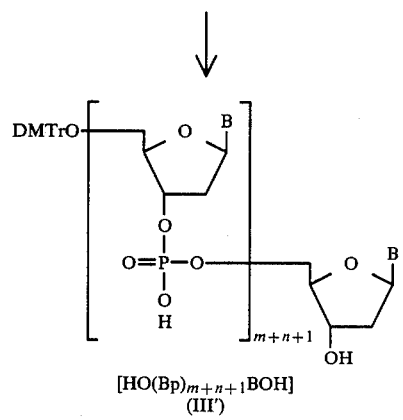
[HO(Bp)$_{m+n+1}$BOH]
(III')
Flow chart of the preparation of the hexadecanucleotide    formula 2
HOApApApCpCpGpApCpCpGpGpCpTpApTpGOH (G1)
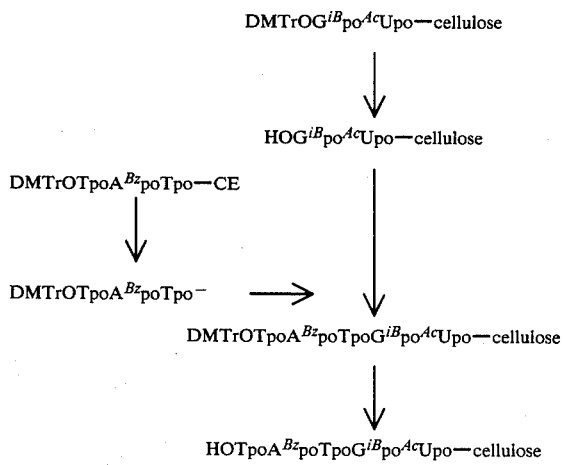

-continued
Flow chart of the preparation of the hexadecanucleotide
HOApApApCpCpGpApCpCpGpGpCpTpApTpGOH (G1)
formula 2
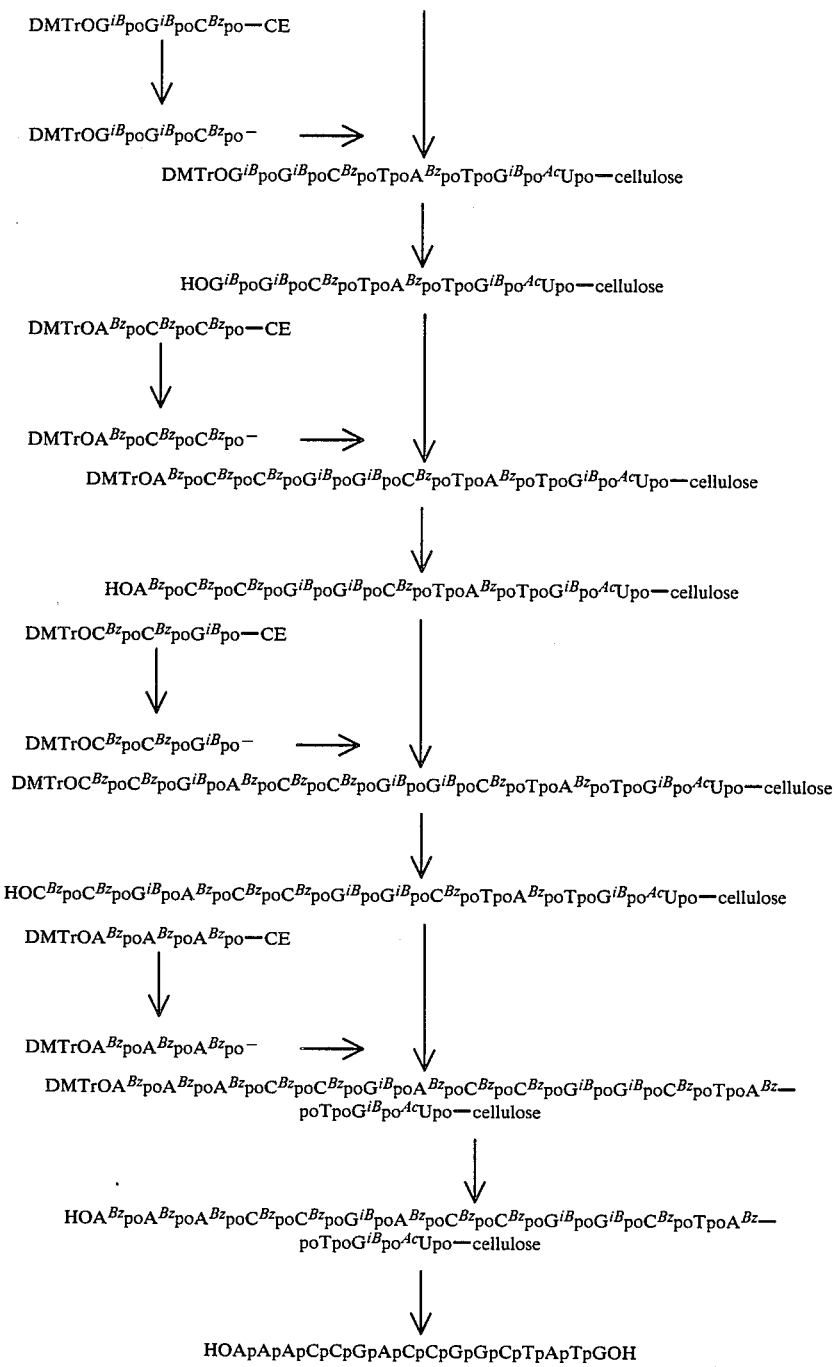
formula 3
Construction of synthetic $^{59}$Val—IGF—I gene
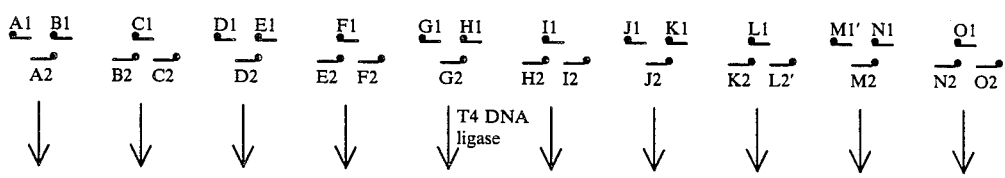

-continued
formula 3
Construction of synthetic $^{59}$Val—IGF—I gene
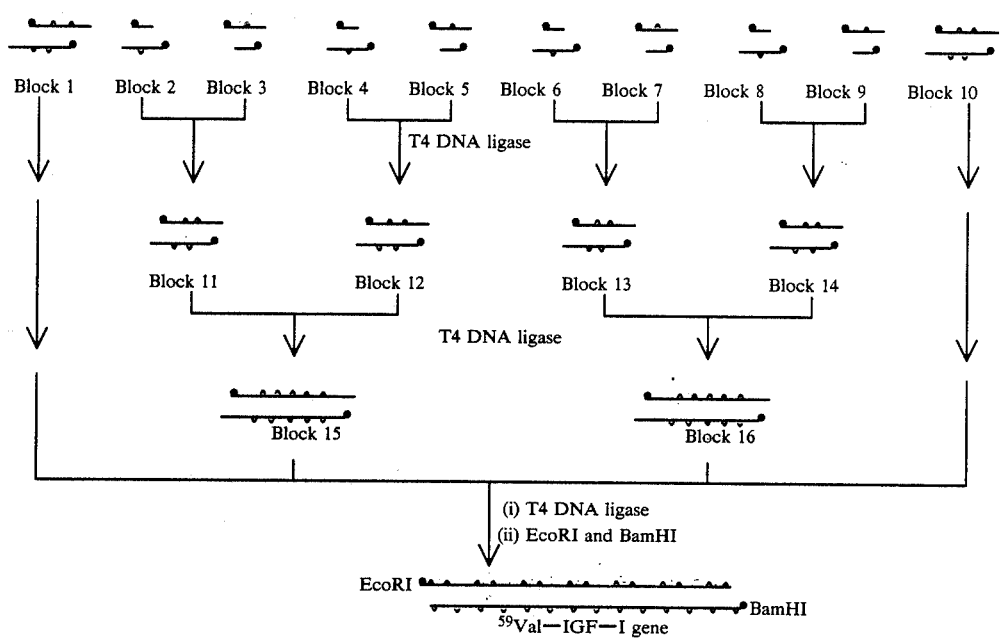
formula 1
Fig. 4    Molecular cloning of synthetic $^{59}$Val-IGF-I gene
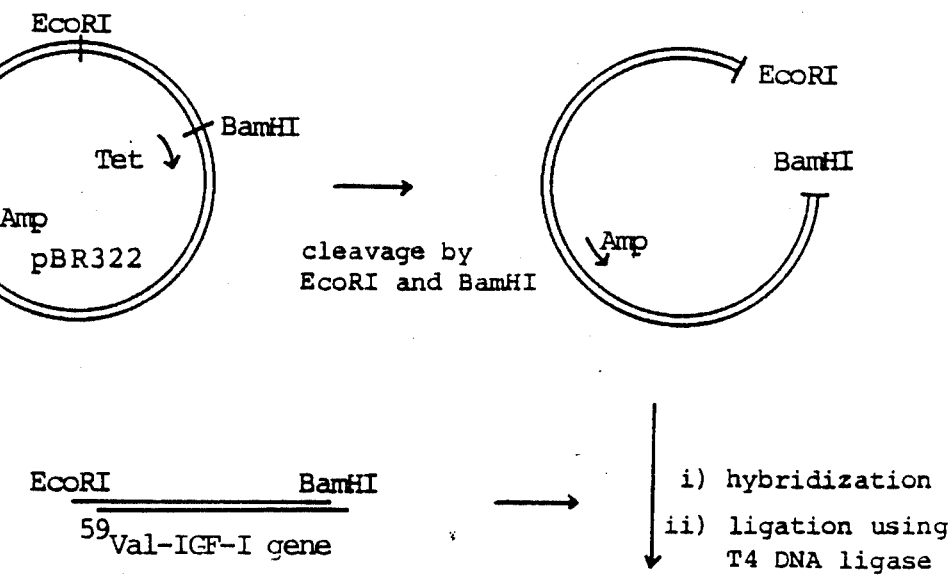

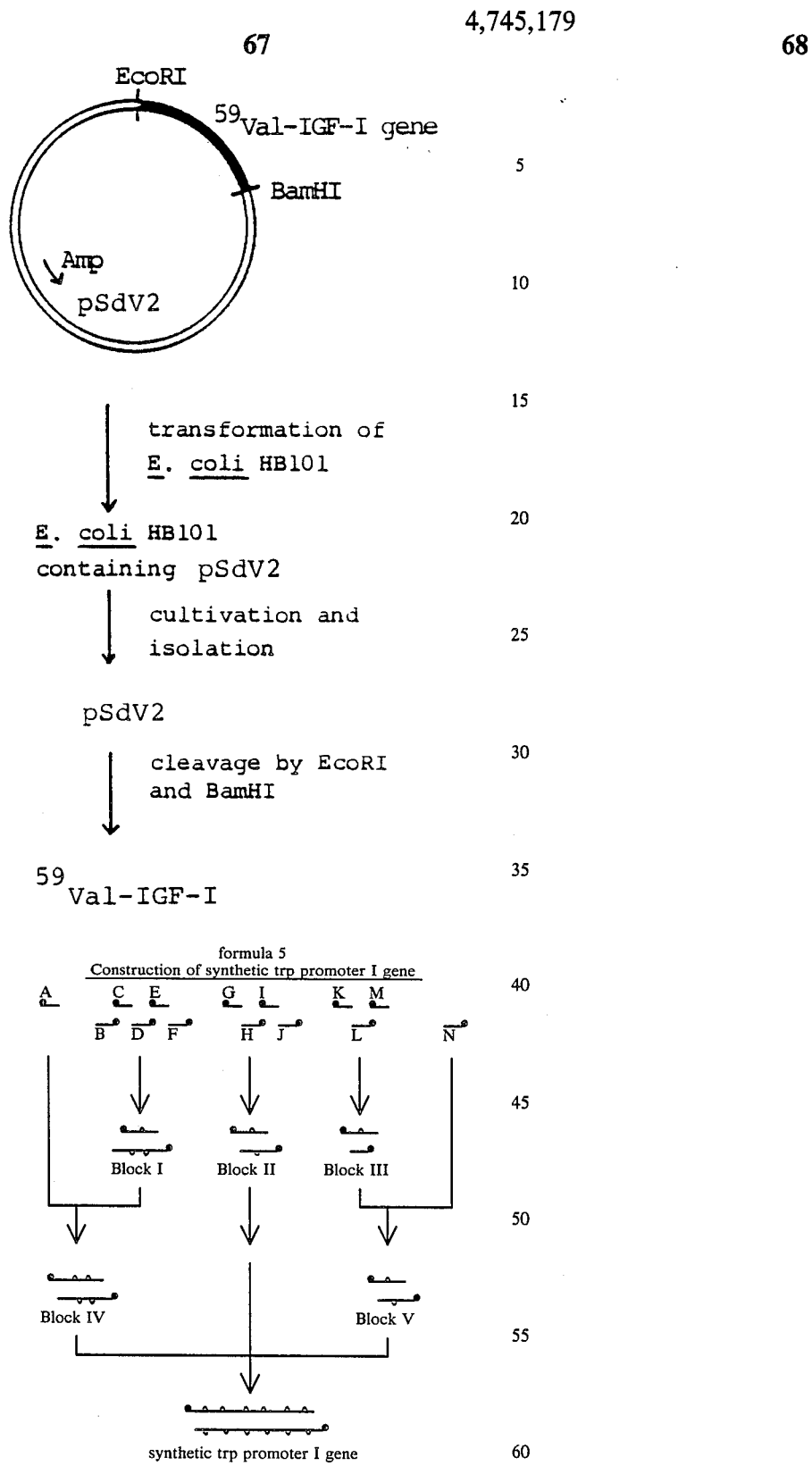

Fig. 6  Molecular cloning of synthetic trp promoter I gene
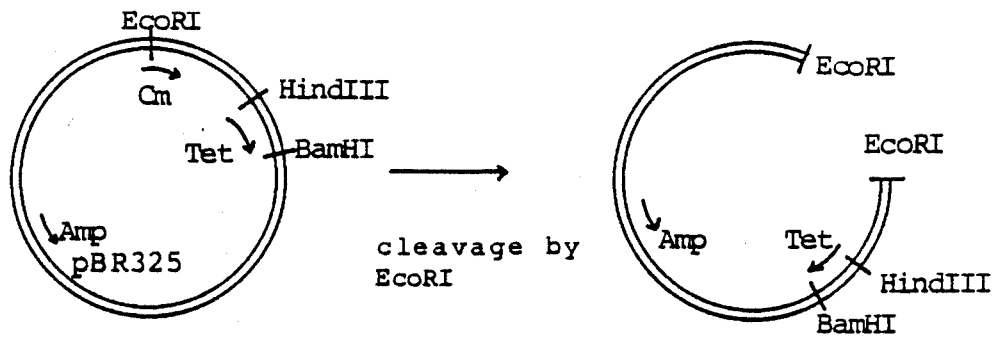
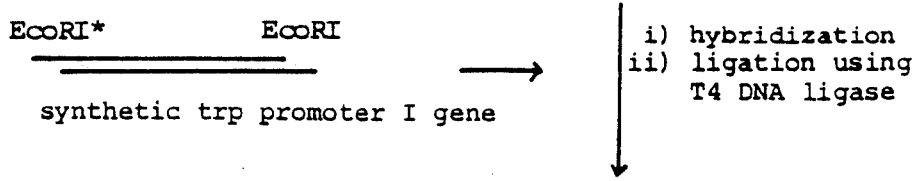
synthetic trp promoter I gene
i) hybridization
ii) ligation using T4 DNA ligase
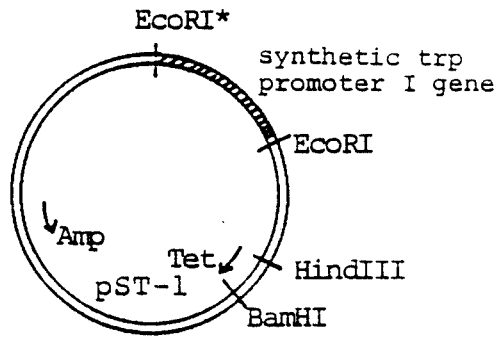
transformation of E. coli HB101
E. coli HB101 containing pST-1
cultivation and isolation
pST-1 formula 7
Construction of synthetic trp promoter II gene
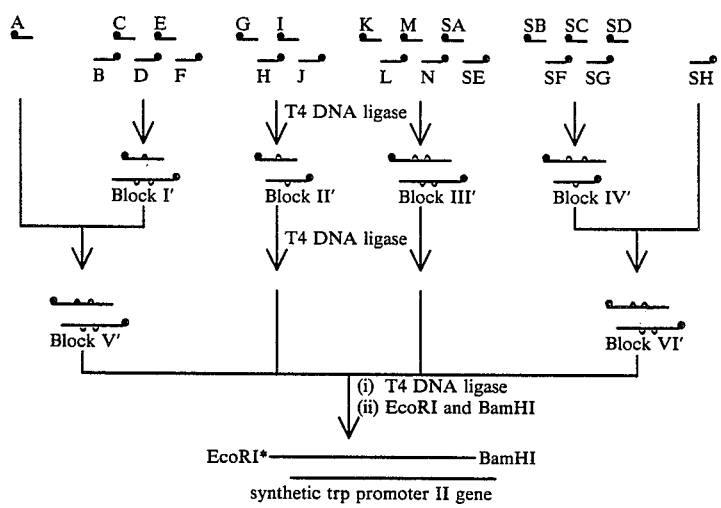
formula 8  Molecular cloning of synthetic trp promoter II gene
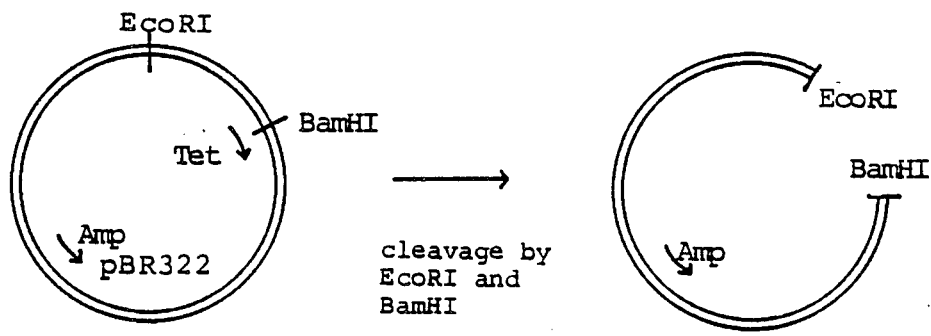
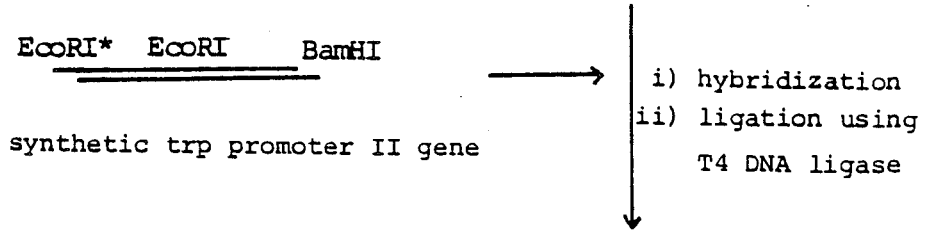
synthetic trp promoter II gene
i) hybridization
ii) ligation using T4 DNA ligase
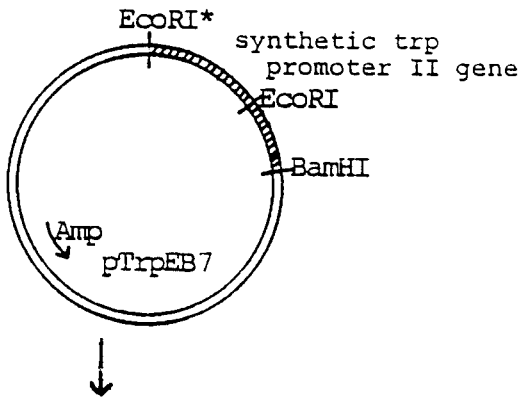

↓ transformation of
  E. coli HB101
E. coli HB101
containing pTrpEB7
↓ cultivation and
  isolation
pTrpEB7
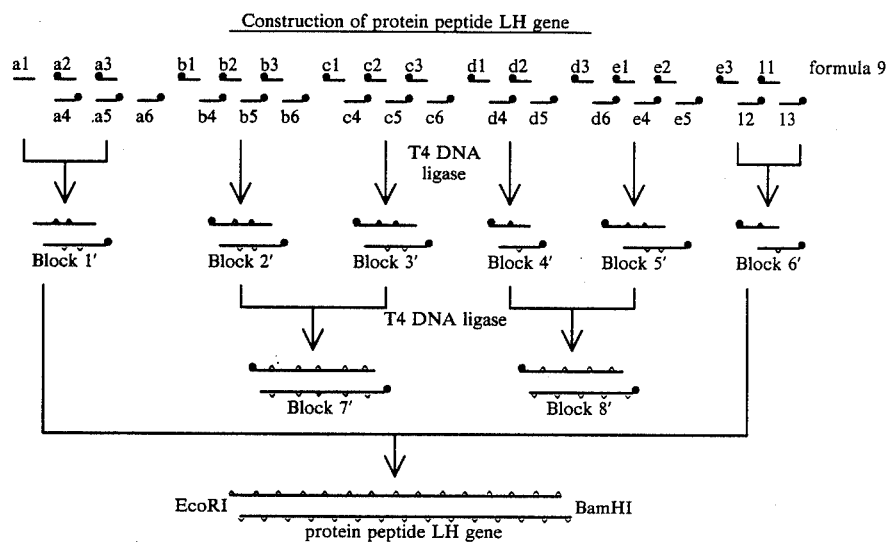

formula 1
Molecular cloning of protein peptide LH gene
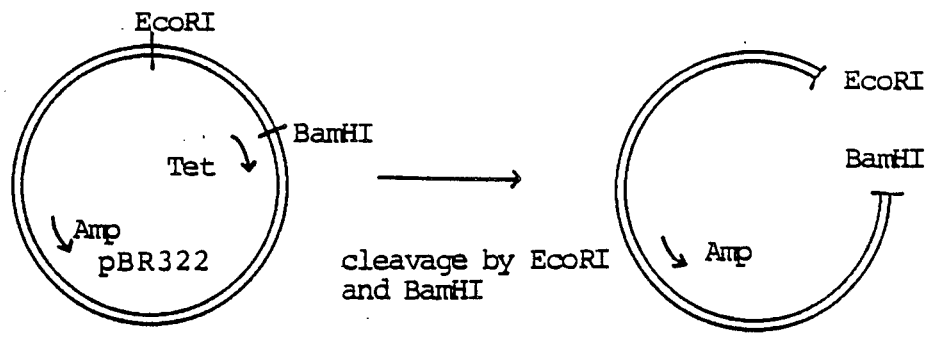
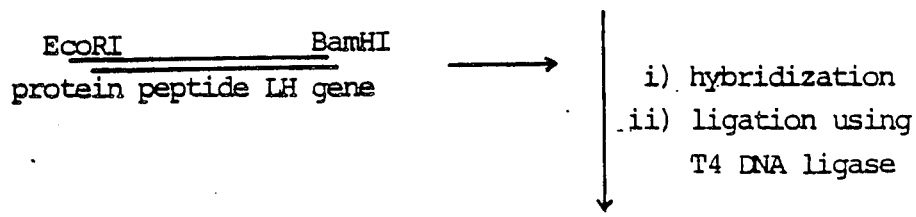
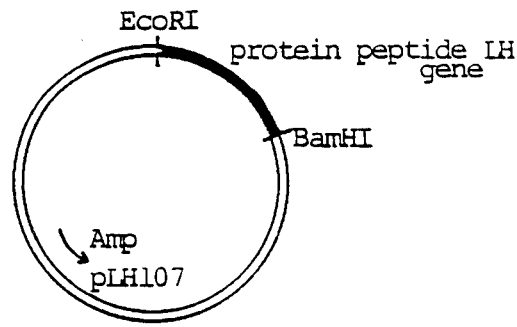
transformation of
E. coli HB101
E. coli HB101
containing pLH107
cultivation and
isolation
pLH107
cleavage by EcoRI
and BamHI
protein peptide
LH gene

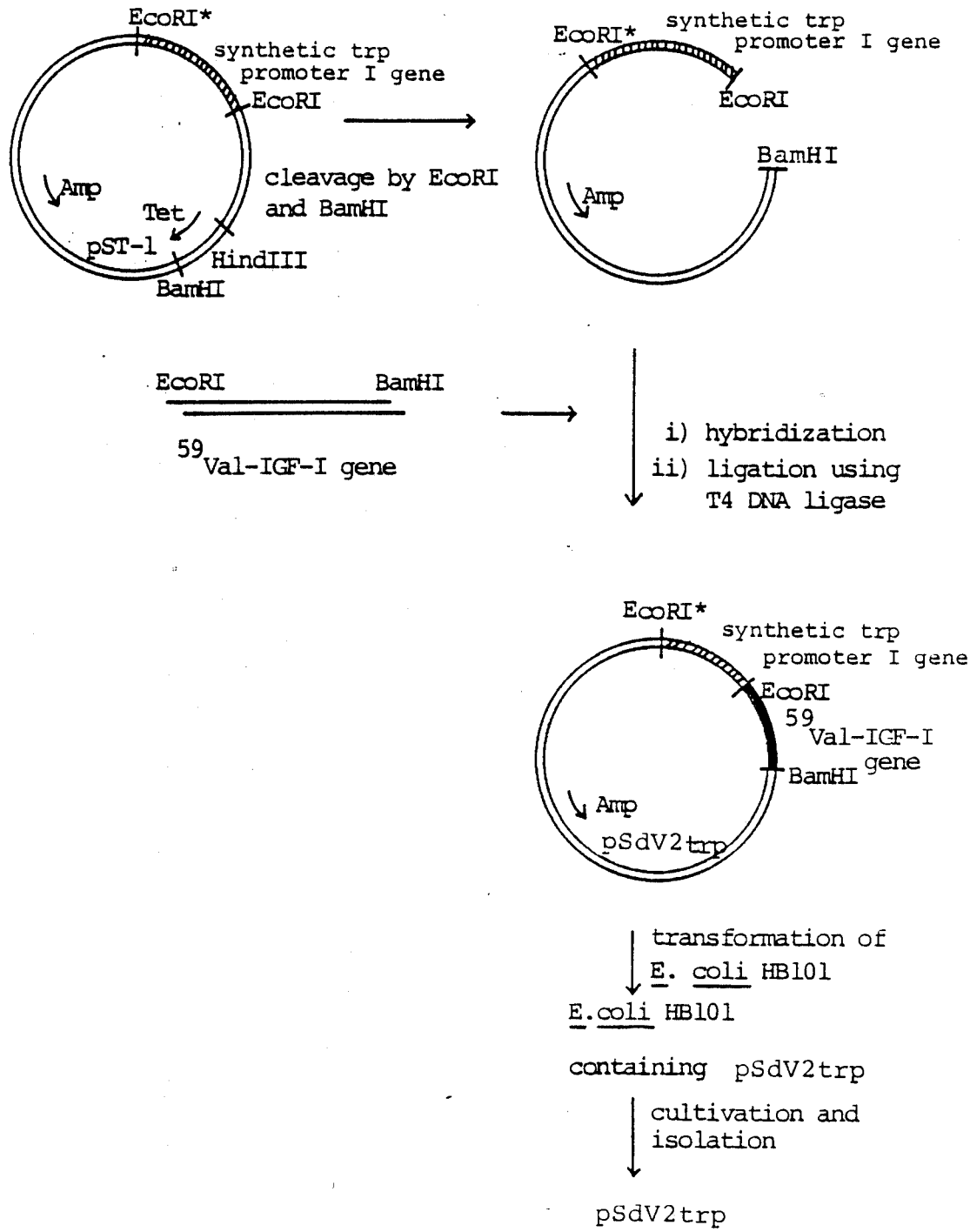
Fig. 11 Construction of recombinant plasmid pSdV2trp

Formula 12 Construction of recombinant plasmid pSdM1-322trp
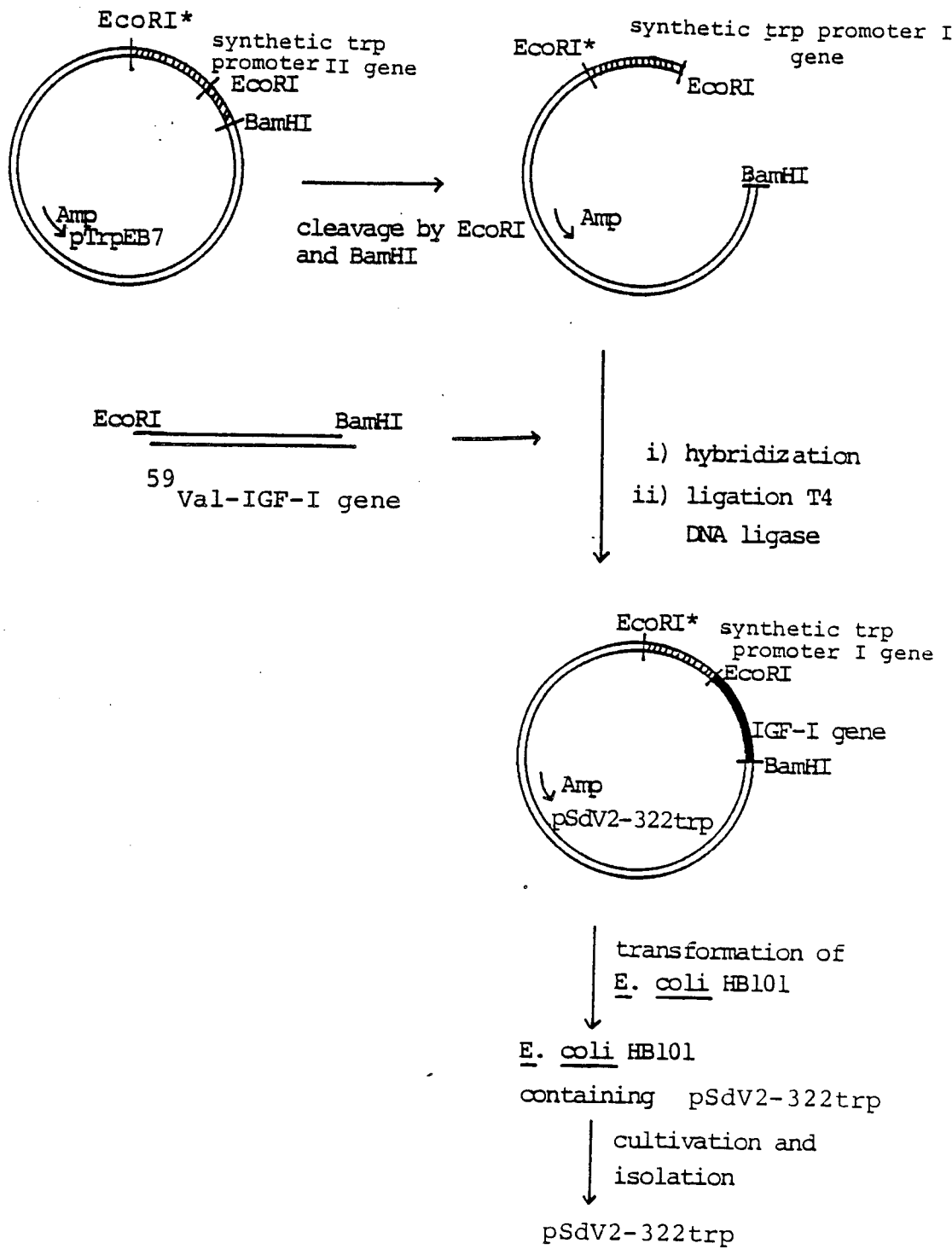

formula
Fig. 13 Construction of recombinant plasmid pLHtrp
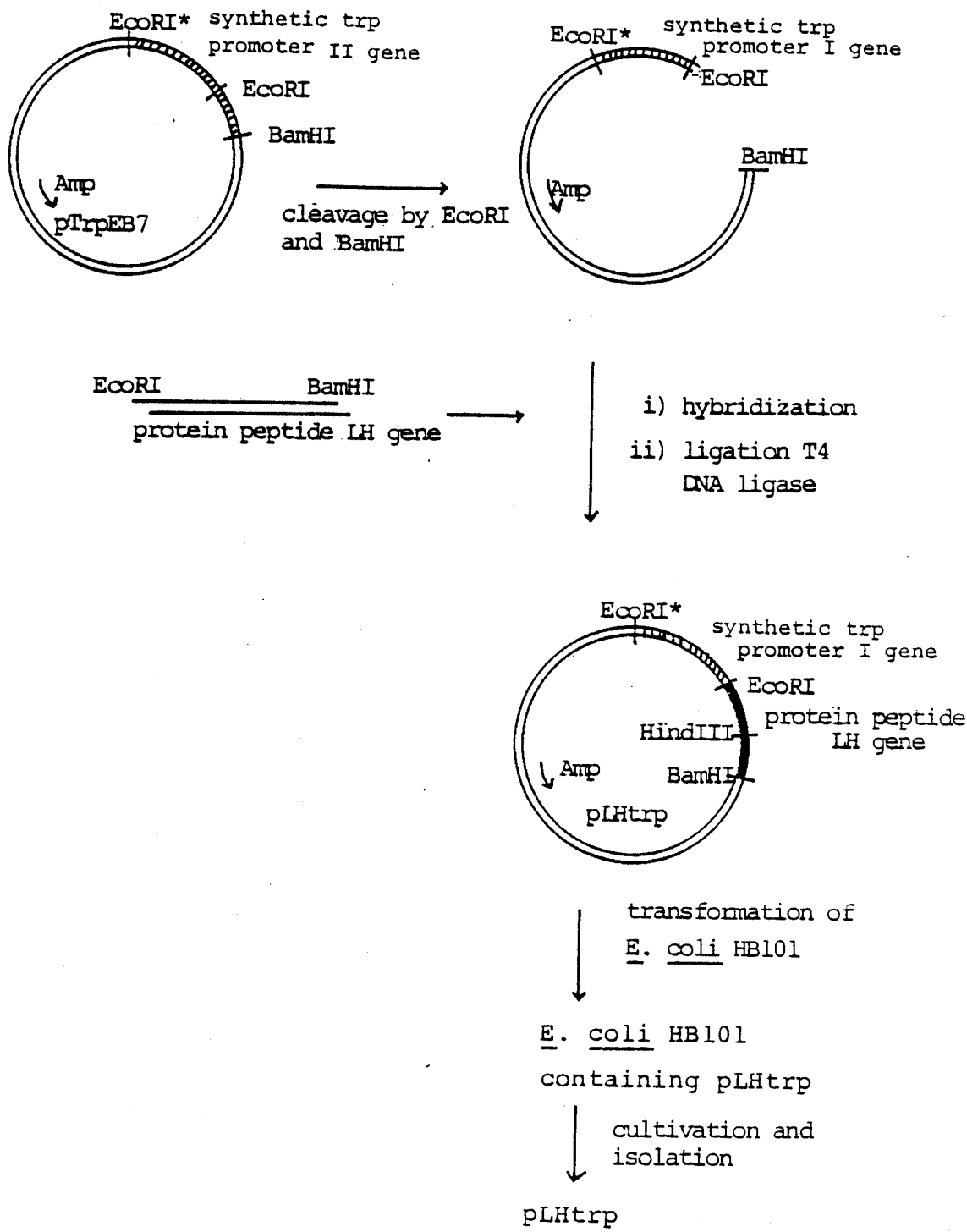

formula 1
Fig. 14 Construction of recombinant plasmid pLHSdVtrp
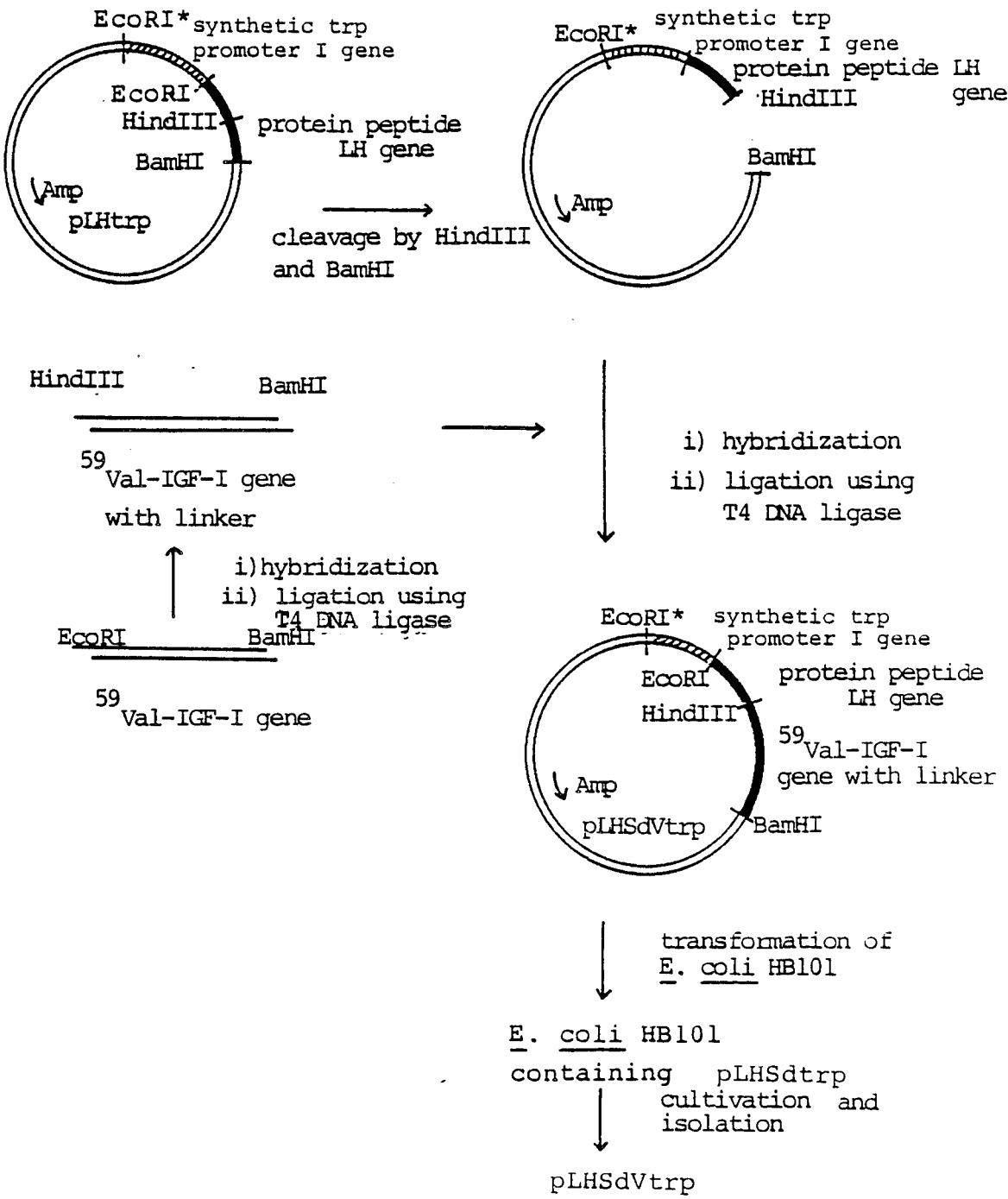

formula 15
Construction of terminator S gene
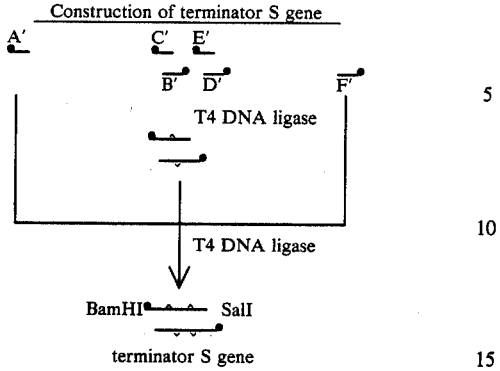
formula 16
Construction of terminator L gene
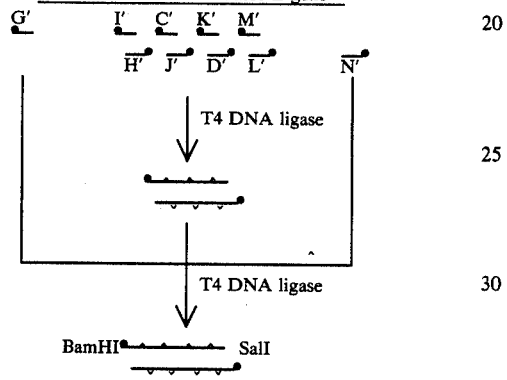
formula 17 Construction of recombinant plasmid PLHSdVtrpS
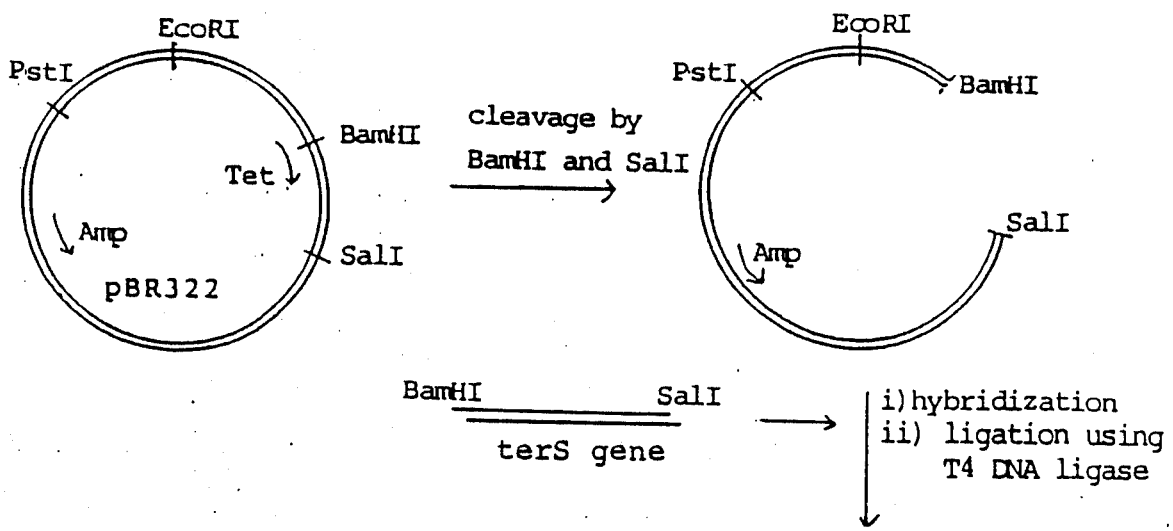

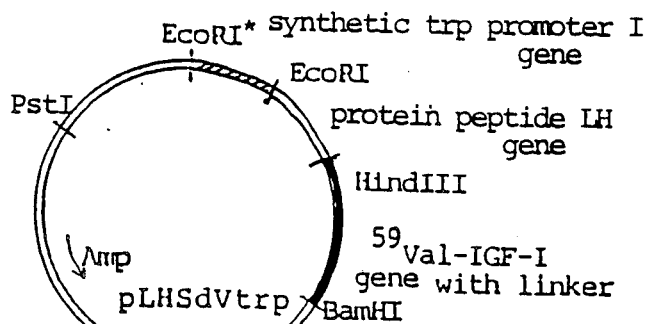
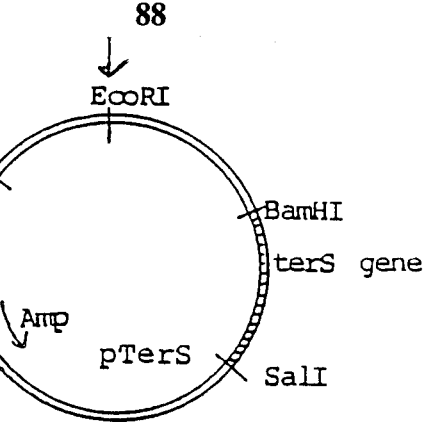
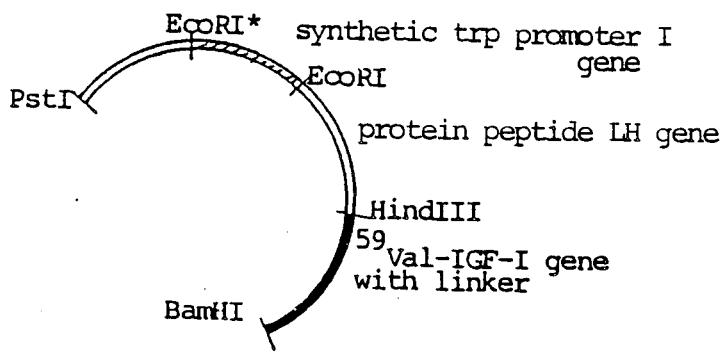
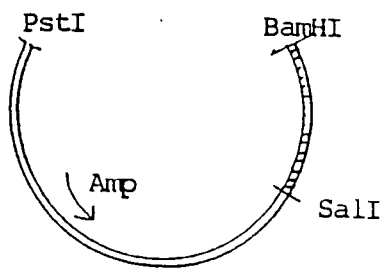
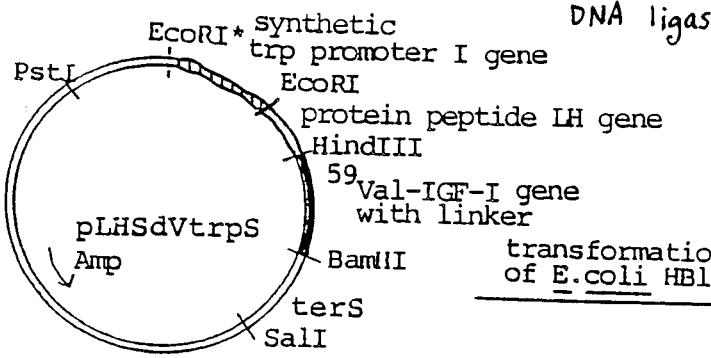

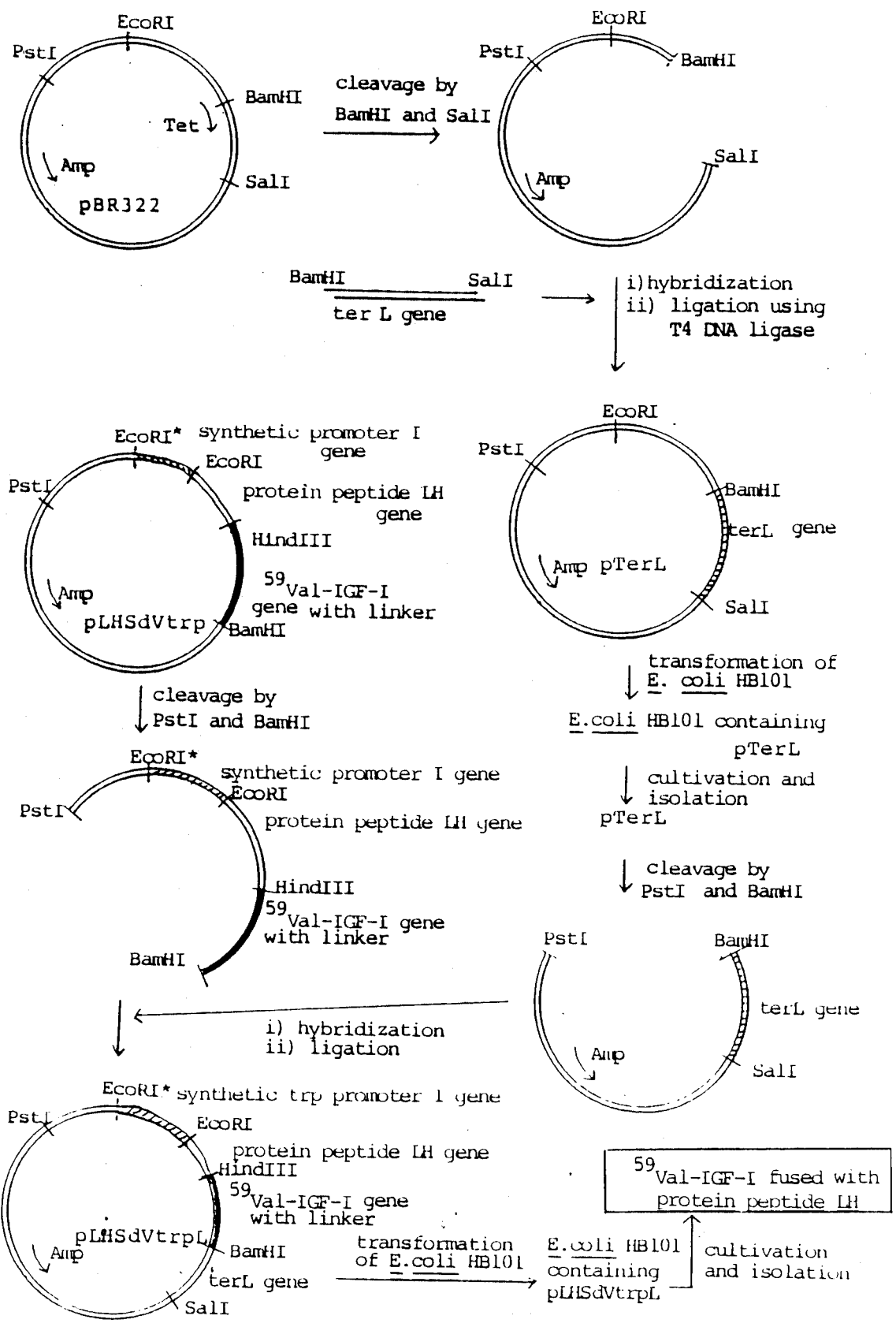
Fig. 18 Construction of recombinant plasmid pLHSdVtrpL

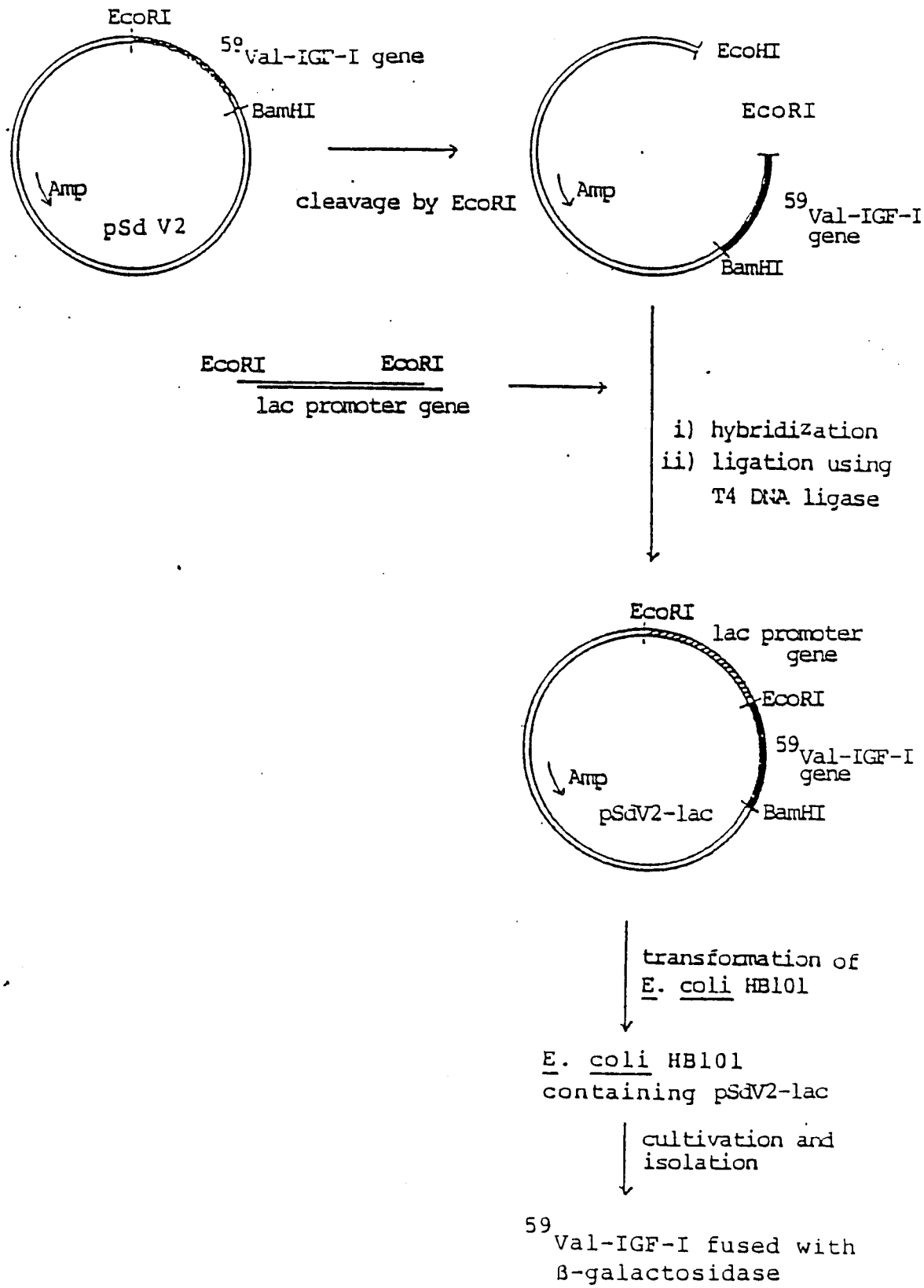
Fig. 19 Construction of recombinant plasmid pSdV2-lac

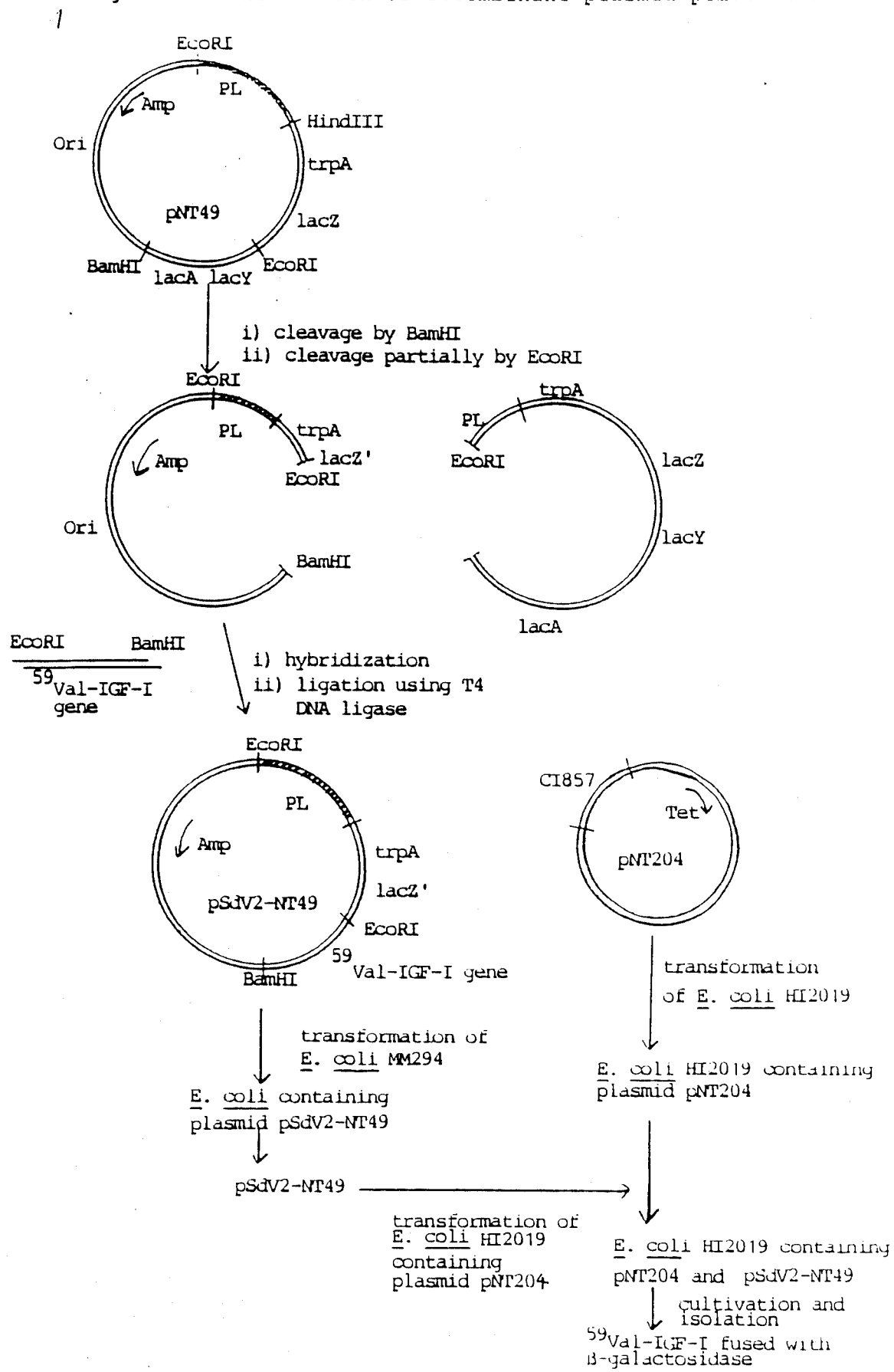
Fig. 20 Construction of recombinant plasmid psdV2-Nt49 formula 21. Amino acid sequence analysis of $^{59}$Val—IGF—I

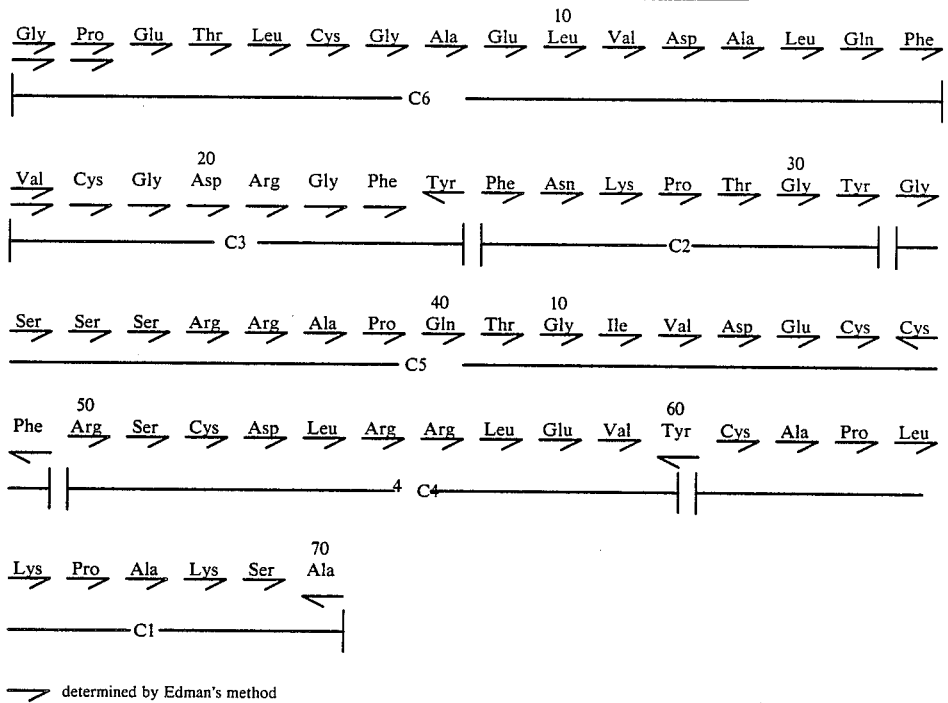

→ determined by Edman's method
← determined by carboxypeptidase method
C1 to C6 show the fragments digested with chymotrypsin

What we claim is:
1. A $^{59}$valine insulin-like growth factor I (hereinafter referred to as $^{59}$Val-IGF-I) fused to a protein peptide LH, wherein said $^{59}$Val-IGF-I has the following amino acid sequence:
Gly-Pro-Glu-Thr-Leu-Cys-Gly-Ala-Glu-Leu-Val-Asp-Ala-Leu-Gln-Phe-Val-Cys-Gly-Asp-Arg-Gly-Phe-Tyr-Phe-Asn-Lys-Pro-Thr-Gly-Tyr-Gly-Ser-Ser-Ser-Arg-Arg-Ala-Pro-Gln-Thr-Gly-Ile-Val-Asp-Glu-Cys-Cys-Phe-Arg-Ser-Cys-Asp-Leu-Arg-Arg-Leu-Glu-Val-Tyr-Cys-Ala-Pro- eu-Lys-Pro-Ala-Lys-Ser-Ala.

2. The $^{59}$Val-IGF-I fused with protein peptide LH of claim 1, having the following amino acid sequence:
Cys-Tyr-Cys-Gln-Asp-Pro-Tyr-Val-Lys-Glu-Ala-Glu-Asn-Leu-Lys-Lys-Tyr-Phe-Asn-Ala-Gly-His-Ser-Asp-Val-Ala-Asp-Asn-Gly-Thr-Leu-Phe-Leu-Gly-Ile-Leu-Lys-Asn-Trp-Lys-Glu-Glu-Ser-Asp-Arg-Lys-Ile-Met-Gln-Ser-Gln-Ile-Val-Ser-Phe-Tyr-Phe-Lys-Leu-Glu-Val-Lys-His Glu-Phe-Met-Gly-Pro-Glu-Thr-Leu-Cys-Gly-Ala-Glu-Leu-Val-Asp-Ala-Leu-Gln-Phe-Val-Cys-Gly-Asp-Arg-Gly-Phe-Tyr-Phe-Asn-Lys-Pro-Thr-Gly-Tyr-Gly-Ser-Ser-Ser-Arg-Arg-Ala-Pro-Gln-Thr-Gly-Ile-Val-Asp-Glu-Cys-Cys-Phe-Arg-Ser-Cys-Asp-Leu-Arg-Arg-Leu-Glu-Val-Ty -Cys-Ala-Pro-Leu-Lys-Pro-Ala-Lys-Ser-Ala.

3. The $^{59}$Val-IGF-I fused protein peptide LH of claim 1, wherein said protein peptide LH has the following amino acid sequence:
Cys-Tyr-Cys-Gln-Asp-Pro-Tyr-Val-Lys-Glu-Ala-Glu-Asn-Leu-Lys-Lys-Tyr-Phe-Asn-Ala-Gly-His-Ser-Asp-Val-Ala-Asp-Asn-Gly-Thr-Leu-Phe-Leu-Gly-Ile-Leu-Lys-Asn-Trp-Lys-Glu-Glu-Ser-Asp-Arg-Lys-Ile-Met-Gln-Ser-Gln-Ile-Val-Ser-Phe-Tyr-Phe-Lys-Leu-Glu-Val-Lys-His Glu-Phe-Met.

* * * * *